(12) United States Patent
Simala-Grant et al.

(10) Patent No.: US 7,326,770 B2
(45) Date of Patent: Feb. 5, 2008

(54) *H. PYLORI* FUCOSYLTRANSFERASES

(75) Inventors: Joanne Simala-Grant, Edmonton (CA); Diane Taylor, Edmonton (CA); Karl F. Johnson, Hatboro, PA (US); Daniel James Bezila, Philadelphia, PA (US)

(73) Assignees: Neose Technologies, Inc., Horsham, PA (US); Governors of the University of Alberta, Edmonton, Alberta (CA)

( * ) Notice: Subject to any disclaimer, the term of this patent is extended or adjusted under 35 U.S.C. 154(b) by 398 days.

(21) Appl. No.: 10/764,212

(22) Filed: Jan. 22, 2004

(65) Prior Publication Data

US 2005/0164338 A1 Jul. 28, 2005

(51) Int. Cl.
*C07K 1/00* (2006.01)
*C07K 14/00* (2006.01)
*C07K 17/00* (2006.01)

(52) U.S. Cl. ............... 530/350; 424/234.1; 435/41
(58) Field of Classification Search ............... None
See application file for complete search history.

(56) References Cited

U.S. PATENT DOCUMENTS

| | | | |
|---|---|---|---|
| 5,280,113 A | | 1/1994 | Rademacher et al. |
| 5,625,124 A * | | 4/1997 | falk ............... 800/2 |
| 6,399,337 B1 * | | 6/2002 | Taylor et al. ............ 435/97 |
| 6,410,719 B1 * | | 6/2002 | Boren et al. ............ 536/23.7 |
| 6,534,298 B2 * | | 3/2003 | Taylor et al. ............ 435/193 |
| 6,709,656 B1 * | | 3/2004 | Boren et al. ............ 424/190.1 |
| 6,962,806 B2 * | | 11/2005 | Taylor et al. ............ 435/193 |
| 7,029,891 B2 * | | 4/2006 | Taylor et al. ............ 435/193 |
| 2002/0058313 A1 * | | 5/2002 | Renkonen et al. ............ 435/105 |
| 2002/0068347 A1 * | | 6/2002 | Taylor et al. ............ 435/193 |
| 2002/0164749 A1 * | | 11/2002 | Taylor et al. ............ 435/193 |
| 2003/0166211 A1 | | 9/2003 | Taylor et al. |
| 2003/0166212 A1 * | | 9/2003 | Taylor et al. ............ 435/193 |
| 2003/0180835 A1 | | 9/2003 | Bayer |

FOREIGN PATENT DOCUMENTS

WO 9855630 * 12/1998

OTHER PUBLICATIONS

Wang Ge et al, Molecular Microbiology, 2000, vol. 36(6), pp. 1187-1196, Lewis antigens in *Helicboacter pylori*, biosynthesis and phase variation.*
Rasko, David A. e tal, J. Bio. Chem., vol. 275(7), pp. 4988-4994, Feb. 18, 2000.*
Rasko, David A. et al, Eur. J. Biochem, vol. 267, pp. 6059-6066, 2000.*
Martin, Stephen et al, J. Bio. Chem. vol. 272(34), pp. 21349-21356, Aug. 22, 1997, Lewis X Biosynthesis in *Helicobacter pylori*.*
Ma, Bing et al, J. Biological Chem., vol. 281(10), pp. 6385-6394, Mar. 10, 2006, Purification, Kinetic Characterization and Mapping of the Minimal Catalytic Domain and the Key Polar Groups of *Helicobacter pylori* alpha (1,3/1,4) -Fucosyltransferases.*

(Continued)

*Primary Examiner*—Mark Navarro
*Assistant Examiner*—Ginny Allen Portner
(74) *Attorney, Agent, or Firm*—Townsend and Townsend and Crew LLP

(57) ABSTRACT

This invention provides nucleic acid and amino acid sequences of fucosyltransferases from *Helicobactor pylori*. The invention also provides methods to use the fucosyltransferases to synthesize oligosaccharides, glycoproteins, and glycolipids.

26 Claims, 27 Drawing Sheets

Strain 1111FutB fucosyltransferase nucleotide coding sequence (SEQ ID NO:15)

```
ggatcccGAGCGACCAATCATTACAGGGATTTATTGCATTTAGATGCGGCTTTCAGTAACACGCTGATCGT
GGAAAATAACGCCTTAAACGGCTTGGTTACCGGGCATATGATGTTTTCACATTCTAAAGGCGAAATGCTCC
TCGCCTTTGCAACGCTCGTTTGAATATCAGTAAAGATCGCACTTTTAGTCGTGGGCGATCGGGGGAATGATTTG
AGCATGTTCAAACATGCCCATATTAAAATCGCTTTCAACGCTAAAGAGGTTTTAAAACAGCACGCCACGCA
TTGCATCAATGAGCCTAATCTAGCCCTAATCAAGCCTTTGATTTACAAAAATTTTTTTGTAAAATTCCCT
TTAAAAGGATAGCCatgttccaacccctattagacgcttatgtagaaagcgcttccattgaaaaatggcc
tctaaatctccccccccctaaaaatcgctgtggcgaattggtgggagatgaagaattaaagaatttaa
aaagagcgctctttatttctattctttagccaacgctacacaatcgccctccaccaaaaccccaatgaatttt
cagatctagtctttagcaatcctcttggatcagctagaaaaatcttatcgtatcaaaacgctaaaagagtg
ttttacaccggtgaaaatgaagtccctaacttcaaactcctttgattacgccataggctttgatgaatgga
ttttagagatcgttatttgaggatgcctttatattatgatagctacaccataaagccgagagcgtgaatcg
acaccacttcgccctacaaactcaaagacaacagcctttatactttaaaaaaaaccctccaccatcaattaa
gaaaaccaccctaatttagcgcagtcgtgaatgatgagagcgatccttgaaaagagagggttgtgagcttt
gtagcgagcaagctaagcgtcctatgagaaacgccttttatgacgcttaaatctcatgagccagttac
tggggggagcgtgaaaacactttagcctataacgtcaaaacaagaacgcagtcttaacgcaataca
agttcaaacctgtgctttgaaaactcacaagcctatggctatgtaaccgagaagatccttgacgcttacttt
agccacaccattcctatttattggggggagtcctagcgtggcgaaagatttaaccccaagagtttgtgaa
tgtccatgattcaacaactttgatgaaggcgatagattatatcaaatactttgcacacgcaccaaagcctt
atttagacatgctcatgaaaaccctttaaacgcccttgatgggaaagcttactttaccgagattgagt
tttaaaaaaatcctagctttttttaaacgatttagaaaacgatacgattcatacaaatcctcaacatc
ttctcatgtggagtgcgaactcagtgagcgttagcgtctattgatgattgagggttaattatgatgattt
gagggttaattatgatgatttgagggttaattatgatgattgagggttaattatgatgatctgagggtta
attatgatgatttgagggttaattatagcgcctttcaaaacgcttcaccttattggaattatcccaaa
acacctctttaaaatctatcgcaaagcctatcaaagcctatcaaaaatcctaccccttattgcgggcat
aaGGAGATGGGTTAAAAGTAAGGTGTCTTTTAAGACTGGTTGAGAAATTGAAGCGCTATTTTAAAATGCG
CTAAGGCTTCTTTTTGAGCGTGGGGTTTTGAGCATGTCCTCTAAAGCATGGGCGCTTAAAAAATGTTTG
GATTTTAAAGACACGATGCGCCCAAAGGATTCTTCTTTAGAAAGGTTTAAAAGGCGTTTGGGCAAAATCTC
GCCAAATACGATAATGACTTTTGAAGCGCTGTTGTCTAATTGCCAGGTCGgaattc
```

Strain 1111FutB fucosyltransferase amino acid sequence (SEQ ID NO:16)

```
MFQPLLDAYVESASIEKMASKSPPPLKIAVANWWGDEEIKEFKKSVLYPIPSQRYTIALHQNPNEFSDLVF
SNPLSRARRILSYQNAKRVTYTGHNEVPNFNLPDYAIGFDELDPRDRYLRMPLYYDRLHHKAKSVNDTTSP
YKLKGNSLYTLKPFSHQFKNNPNLCAVVWDESDPLKRGVVSFVASNANAPMRNAFYDALNSIEPVTGGGS
VKNTLQXYNVKNKSEFLSQYKFNLCPENSQQYGYVTEKILDAYFSHTIPIYWGSPSVARDFNPKEFVNVHDF
NNFDEAIDYIKYLHTHPNAYLDMLYEMPLNALDGKAYFYQDLSFKKILAFFKTILENDTIYHKSSTSYMWS
CDLDBPLASIDDLRVNYDDLRVNYDDLRVNYDDLRVNYDDLRVNYERLLQNASPLLELSQNTSP
KIYRKAVQKPIKMPYPYCAP
```

OTHER PUBLICATIONS

Wang et al (2000) reference of record.*
Rasko et al (2000, The Journal of Biological Chemistry), reference of record.*
Rasko et al (Oct. 2000) reference of record.*
Alm, R., et al., "Genomic-sequence comparison of two unrelated isolates of the human gastric pathogen *Helicobacter pylori*," *Nature*, Jan. 14, 1999, pp. 176-180, vol. 397, 1 page correction, Feb. 25, 1999.
Ge, Z., et al., "Cloning and Heterologous Expression of a α1,3-Fucosyltransferase Gene from the Gastric Pathogen *Helicobacter pylori*," *The Journal of Biological Chemistry*, 1997, pp. 21357-21363, vol. 272, No. 34, U.S.A.
Rasko, D., et al., "Synthesis of mono- and di-fucosylated type I Lewis blood group antigens by *Helicobacter pylori*," *Eur. J. Biochem.*, 2000, pp. 6059-6066, vol. 267.
Rasko, D., et al., "Cloning and Characterization of the α(1,3/4) Fucosyltransferase of *Helicobacter pylori*" *The Journal of Biological Chemistry*, 2000, pp. 4988-4994, vol. 275, No. 7, U.S.A.
Wang, G., et al., "Molecular genetic basis for the variable expression of Lewis Y antigen *Helicobacter pylori*: analysis of the α(1,2) fucosyltransferase gene," *Molecular Microbiology*, 1999, pp. 1265-1274, vol. 31, No. 4.
NCBI Database Online; Accession No. NP_223719; Authors: Alm, R.A., et al.,; Title: "Genomic-sequence comparison of two unrelated isolates of the human gastric pathogen *Helicobacter pylori*," Definition: alpha-(1,3) -fucosyltransferase [*Helicobacter pylori* J99]; 2 pages.

NCBI Database Online; Accession No. NP_223314; Authors: Alm, R.A., et al.,; Title: " Genomic-sequence comparison of two unrelated isolates of the human gastric pathogen *Helicobacter pylori*," Definition: alpha-(1,3) -fucosyltransferase [*Helicobacter pylori* J99]l 2 pages.
NCBI Database Online; Accession No. AAB81031; Authors: GE, Z., et al.,; Submitted: Jun.. 16, 1997; Definition: alpha 1,3-fucosyltransferase [*Helicobacter pylori*]: 2 pages.
NCBI Database Online; Accession No. AAB93985; Authors: Martin, S.L., et al., Submitted: May 29, 1997; Definition: alpha-(1,3)-fucosyltransferase [*Helicobacter pylori*]; 2 pages.
NCBI Database Online; Accession No. AAR88243; Authors: Rabbani, S., et al., Submitted: Oct. 27, 2003; Definition: alpha-1,4-fucosyltransferase [*Helicobacter pylori*]; 2 pages.
NCBI Database Online; Accession No. AAF35291; Authors: Rasko, D.A., et al., Submitted: Oct. 13, 1999; Definition: alpha-1,3/4-fucosyltransferase [*Helicobacter pylori*]; 2 pages.
NCBI Database Online; Accession No. NP_207445; Authors: Tomb, J-F., et al., Title: "The complete genome sequence of the gastric pathogen *Helicobacter pylori*," Definition: fucosyltransferase [*Helicobacter pylori* 26695]; 1997, 2 pages.
NCBI Database Online; Accession No. NP_207177; Authors: Tomb, J-F., et al., Title: "The complete genome sequence of the gastric pathogen *Helicobacter pylori*," Definition: fucosyltransferase [*Helicobacter pylori* 26695]; 1997, 2 pages.

* cited by examiner

FIGURE 1

Fucosyltransferase nucleotide sequence from strain 1182 FutB (SEQ ID NO:1)

atgttccaaccccctattagacgcttatatagaaagcgcttccattgaaaaaattacctctaaatctcccccccccctaaaaatcgctg
tggcgaattggtggggagatgaagaggttgaagaatttaaaaagaacattctttattttattctcagtcagcattacacaatcaccct
ccaccaaaaccccaacgaaccctccgatctcgtctttggcagtcctattggatcagccagaaaaatcttatcctatcaaaacgcaa
aaagagtgttttacaccggtgaaaacgaatcgcctaatttcaacctctttgattacgccataggctttgatgaattggattttagagat
cgttatttaagaatgcctttatattatgatagactacaccataaagccgagagcgtgaatgacaccacttcgccttacaaactcaaac
ctgacagcctttatgctttaaaaaaaccctcccatcattttaaagaaaaccaccccaatttatgcgcagtagtgaacaatgagagcg
atcctttgaaaagagggtttgcgagttttgtagcgagcaacccctaacgctcctaaaaggaatgctttctatgacgttttaaattctata
gagccagttattgggggagggagcgtgaaaaacactttaggctataacattaaaaacaagagcgagtttttaagccaatacaaat
tcaatctgtgttttgaaaactcacaaggctatggctatgtaactgaaaaaatcattgacgcttactttagccataccattcctatttattg
ggggagtcctagcgtggcacaagattttaacccctaagagttttgtgaatgtttgtgattttaaagattttgatgaagcgattgatcatgt
gcgatacttgcacacgcacccaaacgcttatttagacatgctttatgaaaaccctttaaacacccttgatgggaaagcttacttttac
caaaatttgagttttaaaaaaaatcctagatttttttaaaacgattttagaaaacgacacgatttatcacgataaccctttattttttatcgt
gatttgaatgagccgttaatatctattgatgatgatttgagggttaattatgatgatttgagggttaattatgatgatttgagggttaatta
tgatgatttgagggttaattatgatgatttgagggttaattatgatgatttgagggttaattatgatgatttgagggttaattatgatgattt
gagggttaattatgatgatttgagggttaattatgatgatttgagggttaattatgatgatttgagggttaattatgagcggctcttaca
aaacgcctcgcctttattagaactctctcaaaacaccacttttaaaatctatcgcaaagcttatcaaaaatccttacctttgttgcgtgc
ggcgagaaagttgattaaaaaattgggtttgtaa Protein sequence from strain 1182 FutB (SEQ ID NO:2)

mfqplldayiesasiekitskspppplkiavanwwgdeeveefkknilyfilsqhytitlhqnpnepsdlvfgspigsarkilsy
qnakrvfytgenespnfnlfdyaigfdeldfrdrylrmplyydrlhhkaesvndttspyklkpdslyalkkpshhfkenhpnl
cavvnnesdplkrgfasfvasnpnapkrnafydvlnsiepvigggsvkntlgyniknkseflsqykfnlcfensqgygyvte
kiidayfshtipiywgspsvaqdfnpksfvnvcdfkdfdeaidhvrylhthpnayldmlyenplntldgkayfyqnlsfkki
ldffktilendtiyhdnpfifyrdlneplisidddlrvnyddlrvnyddlrvnyddlrvnyddlrvnyddlrvnyddlrvnydd
lrvnyddlrvnyddlrvnyddlrvnyerllqnaspllelsqnttfkiyrkayqkslpllraarklikklgl*

FIGURE 2

Fucosyltransferase from strain 1111 FutA

Nucleotide coding sequence (SEQ ID NO:3)

atgttccaaccccctattagatgcctttatagaaagcgctccattgaaaaaatggcctctaaatctccccccccctaaaaatcgctgtgg
cgaattggtggggagatgaagaaattaaaaaatttaaaaagagcgttctttattttatcctaagccagcattacacaatcactttaca
ccgaaaccctgataaacctgcggacatcgtctttggtaaccccccttggatcagccagaaaaatcttatcctatcaaaacgcaaaaa
gggtgttttacaccggtgaaaatgaagtccctaacttcaacctctttgattacgccataggctttgatgaattggactttagagatcgt
tatttgagaatgcctttgtattatgcctatttgcattataaagccgagcttgttaatgacaccacttcgccttataaactccaacctgaca
gcctttatgctttaaaaaaacccctcccatcattttaaagaaaaccaccccaatttgtgcgcagtagtgaataatgagagtgatcctttg
aaaagagggtttgcgagctttgtcgcaagcaaccctaacgctcctagaaggaacgcttttatgaggctttaaacgctattgagcc
agttgctgggggagggagcgtgaaaaacactttaggctataatgtcaaaaacaagagcgagtttttaagccaatacaaattcaat
ctgtgttttgaaaacactcaaggctatggctatgtaactgaaaagatcattgacgcttatttcagccataccattcctatttattgggggg
agtcccagcgtggcgaaagattttaaccctaagagttttgtgaatgtccatgatttcaacaactttgatgaagcgattgactatatca
gatacttgcacacgcacccaaacgcttatttagacatgcactatgaaaacccctttaaacactattgatgggaaagcttacttttacca
aaatttgagttttaaaaaaatcctagattttttaaaacgattttagaaaacgacacgatctatcacgataacccttcattttctatcgtg
atttgaatgagccttcagtatctattgatggtttgagggttaattatgatgatttgagggttaattatgatgatttgagggttaattatgat
gatttgagggttaattatgagcgccttttacaaaacgcctcgcctttattagaactctctcaaaacaccacttttaaaatctatcgcaaa
gcttatcaaaaatccttgcctttgttgcgtgccataaggagatgggttaaaaagtaa

Protein sequence (SEQ ID NO:4)

mfqplldafiesaplkkwplnlpplkiavanwwgdeeikkfkksvlyfilsqhytitlhrnpdkpadivfgnplgsarkilsy
qnakrvfytgenevpnfnlfdyaigfdeldfrdrylrmplyyaylhykaelvndttspyklqpdslyalkkpshhfkenhpn
lcavvnnesdplkrgfasfvasnpnaprmafyealnaiepvagggsvkntlgynvknkseflsqykfnlcfentqgygyvt
ekiidayfshtipiywgspsvakdfnpksfvnvhdfnnfdeaidyirylhthpnayldmhyenplntidgkayfyqnlsfk
kildffktilendtiyhdnpfifyrdlnepsvsidglrvnyddlrvnyddlrvnyddlrvnyerllqnaspllelsqnttfkiyrka
yqkslpllrairrwvkk*

FIGURE 3

Strain 1218 FutB nucleotide sequence (SEQ ID NO:5)

atgttccaaccccctattagacgcttatatagaaagcgcttccattgaaaaaattacctctaaatctccccccccctaaaaatcgctg
tggcgaattggtggggagatgaagaggttgaagaatttaaaaagaacattctttattttattctcagtcagcattacacaatcaccct
ccaccaaaaccccaacgaaccctccgatctcgtctttggcagtcctattggatcagccagaaaaatcttatcctatcaaaacgcaa
aaagagtgttttacaccggtgaaaacgaatcgcctaatttcaacctctttgattacgccataggctttgatgaattggattttagagat
cgttatttaagaatgcctttatattatgatagactacaccataaagccgagagcgtgaatgacaccacttcgccttacaaactcaaac
ctgacagcctttatgctttaaaaaaaccctcccatcattttaaagaaaaccaccccaatttatgcgcagtagtgaacaatgagagcg
atcctttgaaaagagggtttgcgagttttgtagcgagcaaccctaacgctcctaaaaggaatgctttctatgacgctttaaattctata
gagccagttattgggggagggagcgtgaaaaacactttaggctataacattaaaaacaagagcgagttttttaagccaatacaaat
tcaatctgtgttttgaaaactcacaaggctatggctatgtaactgaaaaaatcattgacgcttactttagccataccattcctatttattg
ggggagtcctagcgtggcacaagatttaaccctaagagttttgtgaatgtttgtgatttttaaagattttgatgaagcgattgatcatgt
gcgatacttgcacacgcacccaaacgcttatttagacatgcttatgaaaacccttaaacacccttgatgggaaagcttacttttac
caaaatttgagttttaaaaaaaatcctagattttttttaaaacgatcttagaaaacgacacgatttatcacgataaacccttttattttttatcgt
gatttgaatgagccgttaatatctattgatgatttgagggttaattatgatgatttgagggttaattatgatgatttgagggttaattatga
tgatttgagggttaattatgatgatttgagggttaattatgatgatttgagggttaattatgatgatttgagggttaattatgatgatttga
gggttaattatgatgatttgagggttaattgtgatgatttgagggttaattatgatgatttgagggttaattatgagcggctcttacaaa
acgcctcgcctttattagaactctctcaaaacaccacttttaaaatctatcgcaaagcttatcaaaaatccttacctttgttgcgtgcgg
cgagaaagttgattaaaaaattgggtttgtaa Predicted protein strain 1218 FutB (SEQ ID NO:6)

mfqplldayiesasiekitsksppplkiavanwwgdeeveefkkniliyfilsqhytitlhqnpnepsdlvfgspigsarkilsy
qnakrvfytgenespnfnlfdyaigfdeldfrdrylrmplyydrlhhkaesvndttspyklkpdslyalkkpshhfkenhpnl
cavvnnesdplkrgfasfvasnpnapkrnafydalnsiepvigggsvkntlgyniknkseflsqykfnlcfensqgygyvte
kiidayfshtipiywgspsvaqdfnpksfvnvcdfkdfdeaidhvrylhthpnayldmlyenplntldgkayfyqnlsfkki
ldffktilendtiyhdnpfifyrdlneplisiddlrvnyddlrvnyddlrvnyddlrvnyddlrvnyddlrvnyddlrvnyddlr
vnyddlrvncddlrvnyddlrvnyerllqnaspllelsqnttfkiyrkayqkslpllraarklikklgl*

FIGURE 4

Fucosyltransferase strain 19C2 FutB nucleotide sequence (SEQ ID NO:7)

atgttccaaccccctattagacgcttatatagacagcacccgtttagatgaaaccgattataagcccccattaaatatagccctagcg
aattggtggcctttggataaaagagaaagcaaagggtttagaaaaaaatttatcttacatttcattttaagtcagcattacacaatcgc
tctccaccgaaaccctgataaacctgcggacatcgttttggtaaccccttggatcagccagaaaaatcctatcctatcaaaacg
ctaaaagggtgttttacaccggtgaaaacgaagtccctaatttcaacctctttgattacgccataggctttgatgaattggactttaga
gatcgttatttgagaatgcctttatattatgatagactacaccataaagccgagagcgtgaatgacaccaccgcaccttacaagatt
aaatctgacagcctttatgctttaaaaaagccctcccatcattttaaagaaaaccacccacatttatgcgcgctaatcaataatgaga
tcgatcctttgaaaagagggtttgcgagctttgtcgcaagcaaccctaacgcccctataaggaacgctttctatgaggctttaaattc
tattgagccagttactgggggagggagcgtgagaaacactttaggctataacgtcaaaaacaaaaacgaattttttgagccaatac
aagttcaatctgtgctttgaaaacactcaaggctatggctatgttactgaaaaaatcattgacgcttacttcagccacaccattcctat
ttattgggggggagtccctagcgtggcgaaagattttaacccc Strain 19C2 FutB protein sequence (SEQ ID NO:8)

mfqplldayidstrldetdykpplnialanwwpldkreskgfrkkfilhfilsqhytialhrnpdkpadivfgnplgsarkilsy
qnakrvfytgenevpnfnlfdyaigfdeldfrdrylrmplyydrlhhkaesvndttapykiksdslyalkkpshhfkenhph
lcalinneidplkrgfasfvasnpnapirnafyealnsiepvtgggsvrntlgynvknkneflsqykfnlcfentqgygyvtek
iidayfshtipiywggvpsvakdfnp

FIGURE 5

Strain 915 FutA fucosyltransferase nucleotide coding sequence (SEQ ID NO:9)

atggcctctaaatctccccccctaaaaatcgctgtggcgaattggtggggagatgaagaaattaaaaaatttaaaaagagcgttct
ttattttatcctaagccagcattacacaatcactttacaccgaaaccctgataaacctgcggacatcgtctttggtaaccccttggat
cagccagaaaaatcttatcctatcaaaacgcaaaaagggtgttttacaccggtgaaaatgaagtccctaacttcaacctctttgatta
cgccataggcttt Protein sequence from Strain 915 FutA (SEQ ID NO:10)

masksppIkiavanwwgdeeikkfkksvlyfilsqhytitlhrnpdkpadivfgnplgsarkilsyqnakrvfytgenevpn
fnlfdyaigf

FIGURE 6

Strain 26695 FutA fucosyltransferase nucleotide coding sequence (SEQ ID NO:11)

atgttccaaccccctattagacgcctttatagaaagcgcttccattgaaaaaatggcctctaaatctccccccccccccctaaaaatc
gctgtggcgaattggtggggagatgaagaaattaaagaatttaaaaagagcgttctttatttatcctaagccaacgctacgcaatc
accctccaccaaaacccccaatgaattttcagatctagttttagcaatcctcttggagcggctagaaagattttatcttatcaaaacac
taaacgagtgttttacaccggtgaaaacgaatcacctaatttcaacctctttgattacgccataggctttgatgaattggatttaatga
tcgttatttgagaatgcctttgtattatgcccatttgcactataaagccgagcttgttaatgacaccactgcgccctacaaactcaaag
acaacagcctttatgctttaaaaaaaccctctcatcattttaaagaaaaccaccctaatttgtgcgcagtagtgaatgatgagagcg
atcttttaaaaagagggtttgccagttttgtagcgagcaacgctaacgctcctatgaggaacgctttttatgacgctctaaattccata
gagccagttactgggggaggaagtgtgagaaacactttaggctataaggttggaaacaaaagcgagttttaagccaatacaagt
tcaatctctgttttgaaaactcgcaaggttatggctatgtaaccgaaaaaatccttgatgcgtattttagccataccattcctatttattg
ggggagtcccagcgtggcgaaagattttaaccctaaaagttttgtgaatgtgcatgatttcaacaactttgatgaagcgattgattat
atcaaatacctgcacacgcacccaaacgcttatttagacatgctctatgaaaaccctttaaacacccttgatgggaaagcttactttt
accaagatttgagttttaaaaaaatcctagattttttttaaaacgattttagaaaacgatacgatttatcacaaattctcaacatctttcatg
tgggagtacgatctgcataagccgttagtatccattgatgatttgagggttaattatgatgatttgagggttaattatgaccggcttta
caaaacgcttcgcctttattagaactctctcaaaacaccacttttaaaatctatcgcaaagcttatcaaaaatccttgcctttgttgcgc
gcggtgagaaagttggttaaaaaattgggtttgtaa

Protein coding sequence Strain 26695 FutA (SEQ ID NO:12)

mfqplldafiesasiekmaskspppplkiavanwwgdecikefkksvlyfilsqryaitlhqnpnefsdlvfsnplgaarkil
syqntkrvfytgenespnfnlfdyaigfdeldfndrylrmplyyahlhykaelvndttapyklkdnslyalkkpshhfkenh
pnlcavvndesdllkrgfasfvasnanapmrnafydalnsiepvtgggsvrntlgykvgnkseflsqykfnlcfensqgygy
vtekildayfshtipiywgspsvakdfnpksfvnvhdfnnfdeaidyikylhthpnayldmlyenplntldgkayfyqdlsf
kkildffktilendtiyhkfstsfmweydlhkplvsiddlrvnyddlrvnydrllqnaspllelsqnttfkiyrkayqkslpllrav
rklvkklgl*

FIGURE 7

19C2A fucosyltransferase nucleotide sequence (SEQ ID NO:13)

atgttccaacccttactagacgcctttatagaaagtgctccaatt

19C2A predicted protein sequence (SEQ ID NO:14)

mfqplldafiesapi

FIGURE 8

Protein sequence from strain 1182 FutB aligned with pfam00852, Glyco_transf_10, Glycosyltransferase family 10

```
Query:   23  PPPLKIAVANWWGDEEVEEFKKNILYFILSQHYTITLHQNPNEPSDLVFGS-PIGSARKI  81
Sbjct:   11  TVPLLLAIYTWWSLIEYKEWKKSPIYFIGSQAPQPPLR---ILLWTWPFNGNPLALSDCP  67

Query:   82  LSYQNAKRVFYTGEN---ESPNFNLF---DYAIGFDELDFRDRYLRMPLYYDRLHHKAES 135
Sbjct:   68  LSYQNTARCRLTANRSPLESADAVLFHHRDLSKGFPDLPPSPRPPGQPWVWASMESPSNS 127

Query:  136  -VNDTTSPYKLKPDSLYALKKPSHHFKENHPNLCAVVNNESDPLKRGFASFVASNPN-AP 193
Sbjct:  128  GLNDLRDGYFNWTLSYRADSDAFHPYGYLEPRLSQVVNAPLLSAKRKGAAWVVSNCNTRS 187

Query:  194  KRNAFYDVLNSIEPVIGGGSVKNTLGYNIKNKSEFLSQYKFNLCFENSQGYGYVTEKIID 253
Sbjct:  188  KRERFYKQLNKHLQVDVGGRVANPLPLKVGCLVETLSQYKFYLAFENSQHYDYVTEKLWK 247

Query:  254  -AYFSHTIPIYWGSPSVAQDFNP-KSFVNVCDFKDFDEAIDHVRYLHTHPNAYL    305
Sbjct:  248  NALQAGTIPVVLGPRAVYEDFVPPKSFIHVDDFKSPKELADYLLYLDTNPTAYS    301
```

FIGURE 9

Fucosyltransferase from strain 1111 FutA aligned with pfam00852, Glyco_transf_10, Glycosyltransferase family 10

```
Query:  27   IAVANWWGDEEIKKFKKSVLYFILSQHYTITLHRNPDKPADIVFG-NPLGSARKILSYQN   85
Sbjct:  16   LAIYTWWSLIEYKEWKKSPIYFIGSQAPQPPLR---ILLWTWPFNGNPLALSDCPLSYQN   72

Query:  86   AKRVFYTGEN---EVPNFNLF---DYAIGFDELDFRDRYLRMPLYYAYLHYKAEL-VNDT  138
Sbjct:  73   TARCRLTANRSPLESADAVLFHHRDLSKGFPDLPPSPRPPGQPWVWASMESPSNSGLNDL  132

Query: 139   TSPYKLQPDSLYALKKPSHHFKENHPNLCAVVNNESDPLKRGFASFVASNPN-APRRNAF  197
Sbjct: 133   RDGYFNWTLSYRADSDAFHPYGYLEPRLSQVVNAPLLSAKRKGAAWVVSNCNTRSKRERF  192

Query: 198   YEALNAIEPVAGGGSVKNTLGYNVKNKSEFLSQYKFNLCFENTQGYGYVTEKIID-AYFS  256
Sbjct: 193   YKQLNKHLQVDVGGRVANPLPLKVGCLVETLSQYKFYLAFENSQHYDYVTEKLWKNALQA  252

Query: 257   HTIPIYWGSPSVAKDFNP-KSFVNVHDFNNFDEAIDYIRYLHTHPNAYLDMHYENPLNTI  315
Sbjct: 253   GTIPVVLGPRAVYEDFVPPKSFIHVDDFKSPKELADYLLYLDTNPTAYS----------  301

Query: 316   DGKAYFYQNLSFKKILDFFKTILENDTIYHDNPFIFYRDLNEPSVSIDGLRVNYDDLRVN  375
Sbjct: 302   ---------------------------EYFEWRYDLRVRLFSWDALR---------   321

Query: 376   YDDLRVNYDDLRVNYERLLQNASPLLELSQNTTFKIYRKAYQ  417
Sbjct: 322   -------YDEGFCRVCRLLQNAPD-----RYKTYPNIAKWFQ  351
```

FIGURE 10

Protein sequence from strain 1218 FutB aligned with pfam00852, Glyco_transf_10, Glycosyltransferase family 10

```
Query:   23   PPPLKIAVANWWGDEEVEEFKKNILYFILSQHYTITLHQNPNEPSDLVFGS-PIGSARKI   81
Sbjct:   11   TVPLLLAIYTWWSLIEYKEWKKSPIYFIGSQAPQPPLR---ILLWTWPFNGNPLALSDCP   67

Query:   82   LSYQNAKRVFYTGEN---ESPNFNLF---DYAIGFDELDFRDRYLRMPLYYDRLHHKAES  135
Sbjct:   68   LSYQNTARCRLTANRSPLESADAVLFHHRDLSKGFPDLPPSPRPPGQPWVWASMESPSNS  127

Query:  136   -VNDTTSPYKLKPDSLYALKKPSHHFKENHPNLCAVVNNESDPLKRGFASFVASNPN-AP  193
Sbjct:  128   GLNDLRDGYFNWTLSYRADSDAFHPYGYLEPRLSQVVNAPLLSAKRKGAAWVVSNCNTRS  187

Query:  194   KRNAFYDALNSIEPVIGGGSVKNTLGYNIKNKSEFLSQYKFNLCFENSQGYGYVTEKIID  253
Sbjct:  188   KRERFYKQLNKHLQVDVGGRVANPLPLKVGCLVETLSQYKFYLAFENSQHYDYVTEKLWK  247

Query:  254   -AYFSHTIPIYWGSPSVAQDFNP-KSFVNVCDFKDFDEAIDHVRYLHTHPNAYLDMLYEN  311
Sbjct:  248   NALQAGTIPVVLGPRAVYEDFVPPKSFIHVDDFKSPKELADYLLYLDTNPTAYS------  301

Query:  312   PLNTLDGKAYFYQNLSFKKILDFFKTILENDTIYHDNPFIFYRDLNEPLISIDDLRVNYD  371
Sbjct:  302   --------------------------------EYFEWRYDLRVRLFSWDALR--YD    323

Query:  372   DLRVNYDDLRVNYDDLRVNYDDLRVNYD  399
Sbjct:  324   EGFCRVCRLLQNAPDRYKTYPNIAKWFQ  351
```

FIGURE 11

Protein sequence from strain 19C2 FutB aligned with pfam00852, Glyco_transf_10, Glycosyltransferase family 10

```
Query:   22  PPLNIALANWWPLDKRESKGFRKKFILHFILSQHYTIALHRNPDKPADIVFG-NPLGSAR   80
Sbjct:   12  VPLLLAIYTWWSL--IEYKEW-KKSPIYFIGSQAPQPPLR---ILLWTWPFNGNPLALSD   65

Query:   81  KILSYQNAKRVFYTGEN---EVPNFNLF---DYAIGFDELDFRDRYLRMPLYYDRLHHKA  134
Sbjct:   66  CPLSYQNTARCRLTANRSPLESADAVLFHHRDLSKGFPDLPPSPRPPGQPWVWASMESPS  125

Query:  135  ES-VNDTTAPYKIKSDSLYALKKPSHHFKENHPHLCALINNEIDPLKRGFASFVASNPN-  192
Sbjct:  126  NSGLNDLRDGYFNWTLSYRADSDAFHPYGYLEPRLSQVVNAPLLSAKRKGAAWVVSNCNT  185

Query:  193  APIRNAFYEALNSIEPVTGGGSVRNTLGYNVKNKNEFLSQYKFNLCFENTQGYGYVTEKI  252
Sbjct:  186  RSKRERFYKQLNKHLQVDVGGRVANPLPLKVGCLVETLSQYKFYLAFENSQHYDYVTEKL  245

Query:  253  ID-AYFSHTIPIYWGGVPSVAKDFNP  277
Sbjct:  246  WKNALQAGTIPVVLGP-RAVYEDFVP  270
```

FIGURE 12

```
                      1                                                 50
1111FutA.pep    (1)   MFQPLLDAFIESAPIKKWPLN--LPPLKIAVANWWGDEEIKK---FKKSV
   19C2A.pep    (1)   MFQPLLDAFIESAPI-----------------------------------
915A.pepneose   (1)   ----------------MASK-SPPLKIAVANWWGDEEIKK---FKKSV
  26695A.pep    (1)   MFQPLLDAFIESASIEKMASKSPPPPLKIAVANWWGDEEIKE---FKKSV
   1182B.pep    (1)   MFQPLLDAFIESASIEKITSKS-PPPLKIAVANWWGDEEVEE---FKKNI
   1218B.pep    (1)   MFQPLLDAFIESASIEKITSKS-PPPLKIAVANWWGDEEVEE---FKKNI
ORF19C2B.pep    (1)   MFQPLLDAVIDSTRLDETDYK---PPLNIAFANWWPLDKRESKGFRKKFI
   Consensus    (1)   MFQPLLDAFIESA IEK  SK   PPLKIAVANWWGDEEI    FKK I 51                                                100
1111FutA.pep   (46)   LYFILSQHYTITLHRNPDKPADIVFGNPLGSARKILSYQNAKRVFYTGEN
   19C2A.pep   (16)   --------------------------------------------------
915A.pepneose  (29)   LYFILSQHYTITLHRNPDKPADIVFGNPLGSARKILSYQNAKRVFYTGEN
  26695A.pep   (48)   LYFILSQRYAITLHQNPNEFEDIVFSNPLGAARKILSYQNTKRVFYTGEN
   1182B.pep   (47)   LYFILSQHYTITLHQNPNEPADIVFGSPIGSARKILSYQNAKRVFYTGEN
   1218B.pep   (47)   LYFILSQHYTITLHQNPNEPADIVFGSPIGSARKILSYQNAKRVFYTGEN
ORF19C2B.pep   (48)   LHFILSQHYTIALHRNPDKPADIVFGNPLGSARKILSYQNAKRVFYTGEN
   Consensus   (51)   LYFILSQHYTITLH NP  PADIVFGNPLGSARKILSYQNAKRVFYTGEN 101                                               150
1111FutA.pep   (96)   EVPNFNLFDYAIGFDELDFRDRYLRMPLYYAYLHYKAELVNDTTSPYKLQ
   19C2A.pep   (16)   --------------------------------------------------
915A.pepneose  (79)   EVPNFNLFDYAIGF------------------------------------
  26695A.pep   (98)   ESPNFNLFDYAIGFDELDFNDRYLRMPLYYAHLHYKAELVNDTTSPYKLK
   1182B.pep   (97)   ESPNFNLFDYAIGFDELDFRDRYLRMPLYYDRLHHKAESVNDTTSPYKLK
   1218B.pep   (97)   ESPNFNLFDYAIGFDELDFRDRYLRMPLYYDRLHHKAESVNDTTSPYKLK
ORF19C2B.pep   (98)   EVPNFNLFDYAIGFDELDFRDRYLRMPLYYDRLHHKAESVNDTTSPYKLK
   Consensus  (101)   E PNFNLFDYAIGFDELDFRDRYLRMPLYY  LHHKAE VNDTTSPYKLK 151                                               200
1111FutA.pep  (146)   PDSLYALKKPSHHFKENHPNLCAVVNNESDPLKRGFASFVASNPNAPRRN
   19C2A.pep   (16)   --------------------------------------------------
915A.pepneose  (93)   --------------------------------------------------
  26695A.pep  (148)   DNSLYALKKPSHHFKENHPNLCAVVNDESDLLKRGFASFVASNANAPMRN
   1182B.pep  (147)   PDSLYALKKPSHHFKENHPNLCAVVNNESDPLKRGFASFVASNPNAPKRN
   1218B.pep  (147)   PDSLYALKKPSHHFKENHPNLCAVVNNESDPLKRGFASFVASNPNAPKRN
ORF19C2B.pep  (148)   SDSLYALKKPSHHFKENHPHLCAVVNNEIDPLKRGFASFVASNPNAPIRN
   Consensus  (151)    DSLYALKKPSHHFKENHPNLCAVVNNESDPLKRGFASFVASNPNAP RN 201                                               250
1111FutA.pep  (196)   AFYDALNAIEPVAGGGSVKNTLGYNVKNKSEFLSQYKFNLCFENSQGYGY
   19C2A.pep   (16)   --------------------------------------------------
915A.pepneose  (93)   --------------------------------------------------
  26695A.pep  (198)   AFYDALNSIEPVTGGGSVKNTLGYKVGNKSEFLSQYKFNLCFENSQGYGY
   1182B.pep  (197)   AFYDVLNSIEPVIGGGSVKNTLGYNVKNKSEFLSQYKFNLCFENSQGYGY
   1218B.pep  (197)   AFYDALNSIEPVIGGGSVKNTLGYNVKNKSEFLSQYKFNLCFENSQGYGY
ORF19C2B.pep  (198)   AFYDALNSIEPVTGGGSVKNTLGYNVKNKNEFLSQYKFNLCFENSQGYGY
   Consensus  (201)   AFYDALNSIEPV GGGSVKNTLGYNVKNKSEFLSQYKFNLCFENSQGYGY
```

```
                          1                                                50
     1111FutA      (1)    ATGTTCCAACCCCTATTAGATGCCTTTATAGAAAGCGCT-CCATTGAAAA
  915A.cod(MWG)    (1)    ATGTTCCAACCCCTATTAGATGCCTTTATAGAAAGCGCTTCCATTGAAAA
   19C2FutA.cod    (1)    ATGTTCCAACCCTTACTAGACGCCTTTATAGAAAGTGCTCCAATT-----
     26695A.cod    (1)    ATGTTCCAACCCCTATTAGACGCCTTTATAGAAAGCGCTTCCATTGAAAA
          1182B    (1)    ATGTTCCAACCCCTATTAGACGCTTATATAGAAAGCGCTTCCATTGAAAA
       1218B.nuc   (1)    ATGTTCCAACCCCTATTAGACGCTTATATAGAAAGCGCTTCCATTGAAAA
        ORF19C2B   (1)    ATGTTCCAACCCCTATTAGACGCTTATATAGACAGCACCCGTTTAGATGA
       Consensus   (1)    ATGTTCCAACCCCTATTAGACGCCTTTATAGAAAGCGCTTCCATTGAAAA 51                                               100
     1111FutA     (50)    AATGGCCTCTAAATCTCCCCCCCC-----TAAAAATCGCTGTGGCGAATT
  915A.cod(MWG)   (51)    AATGGCCTCTAAATCTCCCCCCC------TAAAAATCGCTGTGGCGAATT
   19C2FutA.cod   (46)    --------------------------------------------------
     26695A.cod   (51)    AATGGCCTCTAAATCTCCCCCCCCCCCCCTAAAAATCGCTGTGGCGAATT
          1182B   (51)    AATTACCTCTAAATCTCCCCCCCCCC---TAAAAATCGCTGTGGCGAATT
       1218B.nuc  (51)    AATTACCTCTAAATCTCCCCCCCCCC---TAAAAATCGCTGTGGCGAATT
        ORF19C2B  (51)    AACCGATTATAA------GCCCCCAT---TAAATATAGCCCTAGCGAATT
       Consensus  (51)    AAT GCCTCTAAATCTCCCCCCCC     TAAAAATCGCTGTGGCGAATT 101                                              150
     1111FutA     (95)    GGTGG-----GGAGATGA-AGAAATTAAAAAATTTAAAAAGAGCGTTCTT
  915A.cod(MWG)   (95)    GGTGG-----GGAGATGA-AGAAATTAAAAAATTTAAAAAGAGCGTTCTT
   19C2FutA.cod   (46)    --------------------------------------------------
     26695A.cod  (101)    GGTGG-----GGAGATGA-AGAAATTAAAGAATTTAAAAAGAGCGTTCTT
          1182B   (98)    GGTGG-----GGAGATGA-AGAGGTTGAAGAATTTAAAAAGAACATTCTT
       1218B.nuc  (98)    GGTGG-----GGAGATGA-AGAGGTTGAAGAATTTAAAAAGAACATTCTT
        ORF19C2B  (92)    GGTGGCCTTTGGATAAAAGAGAAAGCAAAGGGTTTAGAAAAAATTTATC
       Consensus (101)    GGTGG     GGAGATGA AGAAATTAAAGAATTTAAAAAGA C TTCTT 151                                              200
     1111FutA    (139)    T---ATTTTATCCTAAGCCAGCATTACACAATCACTTTACACCGAAACCC
  915A.cod(MWG) (139)    T---ATTTTATCCTAAGCCAGCATTACACAATCACTTTACACCGAAACCC
   19C2FutA.cod  (46)    --------------------------------------------------
     26695A.cod (145)    T---ATTTTATCCTAAGCCAACGCTACGCAATCACCCTCCACCAAAACCC
          1182B  (142)    T---ATTTTATTCTCAGTCAGCATTACACAATCACCCTCCACCAAAACCC
       1218B.nuc (142)    T---ATTTTATTCTCAGTCAGCATTACACAATCACCCTCCACCAAAACCC
        ORF19C2B (142)    TTACATTTCATTTTAAGTCAGCATTACACAATCGCTCTCCACCGAAACCC
       Consensus (151)    T   ATTTTAT CTAAG CAGCATTACACAATCAC CTCCACC AAACCC 201                                              250
     1111FutA    (186)    TGATAAACCTGCGGACATCGTCTTTGGTAACCCCCTTGGATCAGCCAGAA
  915A.cod(MWG) (186)    TGATAAACCTGCGGACATCGTCTTTGGTAACCCCCTTGGATCAGCCAGAA
   19C2FutA.cod  (46)    --------------------------------------------------
     26695A.cod (192)    CAATGAATTTTCAGATCTAGTTTTTAGCAATCCTCTTGGAGCGGCTAGAA
          1182B  (189)    CAACGAACCCTCCGATCTCGTCTTTGGCAGTCCTATTGGATCAGCCAGAA
       1218B.nuc (189)    CAACGAACCCTCCGATCTCGTCTTTGGCAGTCCTATTGGATCAGCCAGAA
        ORF19C2B (192)    TGATAAACCTGCGGACATCGTTTTTGGTAACCCCCTTGGATCAGCCAGAA
       Consensus (201)       AT AACCT C GA TCGTCTTTGG AA CC CTTGGATCAGCCAGAA
```

FIG. 13 (1/6)

```
                        251                                              300
   1111FutA     (236)   AAATCTTATCCTATCAAAACGCAAAAAGGGTGTTTTACACCGGTGAAAAT
915A.cod(MWG)   (236)   AAATCTTATCCTATCAAAACGCAAAAAGGGTGTTTTACACCGGTGAAAAT
 19C2FutA.cod    (46)   --------------------------------------------------
   26695A.cod   (242)   AGATTTTATCTTATCAAAACACTAAACGAGTGTTTTACACCGGTGAAAAC
        1182B   (239)   AAATCTTATCCTATCAAAACGCAAAAAGAGTGTTTTACACCGGTGAAAAC
     1218B.nuc  (239)   AAATCTTATCCTATCAAAACGCAAAAAGAGTGTTTTACACCGGTGAAAAC
      ORF19C2B  (242)   AAATCCTATCCTATCAAAACGCTAAAAGGGTGTTTTACACCGGTGAAAAC
      Consensus (251)   AAATCTTATCCTATCAAAACGCAAAAG GTGTTTTACACCGGTGAAAAC 301                                              350
   1111FutA     (286)   GAAGTCCCTAACTTCAACCTCTTTGATTACGCCATAGGCTTT-GATGAAT
915A.cod(MWG)   (286)   GAAGTCCCTAACTTCAACCTCTTTGATTACGCCATAGGCTTTTGATGA--
 19C2FutA.cod    (46)   --------------------------------------------------
   26695A.cod   (292)   GAATCACCTAATTTCAACCTCTTTGATTACGCCATAGGCTTT-GATGAAT
        1182B   (289)   GAATCGCCTAATTTCAACCTCTTTGATTACGCCATAGGCTTT-GATGAAT
     1218B.nuc  (289)   GAATCGCCTAATTTCAACCTCTTTGATTACGCCATAGGCTTT-GATGAAT
      ORF19C2B  (292)   GAAGTCCCTAATTTCAACCTCTTTGATTACGCCATAGGCTTT-GATGAAT
      Consensus (301)   GAA   CCTAATTTCAACCTCTTTGATTACGCCATAGGCTTT GATGAAT 351                                              400
   1111FutA     (335)   TGGACTTTAGAGATCGTTATTTGAGAATGCCTTTGTATTATGCCTATTTG
915A.cod(MWG)   (334)   --------------------------------------------------
 19C2FutA.cod    (46)   --------------------------------------------------
   26695A.cod   (341)   TGGATTTTAATGATCGTTATTTGAGAATGCCTTTGTATTATGCCCATTTG
        1182B   (338)   TGGATTTTAGAGATCGTTATTTAAGAATGCCTTTATATTATGATAGACTA
     1218B.nuc  (338)   TGGATTTTAGAGATCGTTATTTAAGAATGCCTTTATATTATGATAGACTA
      ORF19C2B  (341)   TGGACTTTAGAGATCGTTATTTGAGAATGCCTTTATATTATGATAGACTA
      Consensus (351)   TGGA TTTAGAGATCGTTATTT AGAATGCCTTT TATTATG        T 401                                              450
   1111FutA     (385)   CATTATAAAGCCGAGCTTGTTAATGACACCACTTCGCCTTATAAACTCCA
915A.cod(MWG)   (334)   --------------------------------------------------
 19C2FutA.cod    (46)   --------------------------------------------------
   26695A.cod   (391)   CACTATAAAGCCGAGCTTGTTAATGACACCACTGCGCCCTACAAACTGAA
        1182B   (388)   CACCATAAAGCCGAGAGCGTGAATGACACCACTTCGCCTTACAAACTCAA
     1218B.nuc  (388)   CACCATAAAGCCGAGAGCGTGAATGACACCACTTCGCCTTACAAACTCAA
      ORF19C2B  (391)   CACCATAAAGCCGAGAGCGTGAATGACACCACCGCGCTTACAAGATTAA
      Consensus (401)   CAC ATAAAGCCGAG   GT AATGACACCACT CGCCTTACAAACTCAA 451                                              500
   1111FutA     (435)   ACCTGACAGCCTTTATGCTTTAAAAAAAGCCCTCCCATCATTTTAAAGAAA
915A.cod(MWG)   (334)   --------------------------------------------------
 19C2FutA.cod    (46)   --------------------------------------------------
   26695A.cod   (441)   AGACAACAGCCTTTATGCTTTAAAAAAAGCCCTCTCATCATTTTAAAGAAA
        1182B   (438)   ACCTGACAGCCTTTATGCTTTAAAAAAACCCTCCCATCATTTTAAAGAAA
     1218B.nuc  (438)   ACCTGACAGCCTTTATGCTTTAAAAAAACCCTCCCATCATTTTAAAGAAA
      ORF19C2B  (441)   ATCTGACAGCCTTTATGCTTTAAAAAAGCCCTCCCATCATTTTAAAGAAA
      Consensus (451)   A CTGACAGCCTTTATGCTTTAAAAAAACCCTCCCATCATTTTAAAGAAA
```

FIG. 13 (2/6)

```
                        501                                             550
   1111FutA     (485)   ACCACCCCAATTTGTGCGCAGTAGTGAATAATGAGAGTGATCCTTTGAAA
915A.cod(MWG)   (334)   --------------------------------------------------
 19C2FutA.cod    (46)   --------------------------------------------------
   26695A.cod   (491)   ACCACCCTAATTTGTGCGCAGTAGTGAATGATGAGAGCGATCTTTTAAAA
        1182B   (488)   ACCACCCCAATTTATGCGCAGTAGTGAACAATGAGAGCGATCCTTTGAAA
     1218B.nuc  (488)   ACCACCCCAATTTATGCGCAGTAGTGAACAATGAGAGCGATCCTTTGAAA
      ORF19C2B  (491)   ACCACCCACATTTATGCGCGCTAATCAATAATGAGATCGATCCTTTGAAA
     Consensus  (501)   ACCACCC AATTT TGCGCAGTAGTGAA AATGAGAGCGATCCTTTGAAA 551                                             600
   1111FutA     (535)   AGAGGGTTTGCGAGCTTTGTCGCAAGCAACCCTAACGCTCCTAGAAGGAA
915A.cod(MWG)   (334)   --------------------------------------------------
 19C2FutA.cod    (46)   --------------------------------------------------
   26695A.cod   (541)   AGAGGGTTTGCCAGTTTTGTAGCGAGCAACGCTAACGCTCCTATGAGGAA
        1182B   (538)   AGAGGGTTTGCGAGTTTTGTAGCGAGCAACCCTAACGCTCCTAAAAGGAA
     1218B.nuc  (538)   AGAGGGTTTGCGAGTTTTGTAGCGAGCAACCCTAACGCTCCTAAAAGGAA
      ORF19C2B  (541)   AGAGGGTTTGCGAGCTTTGTCGCAAGCAACCCTAACGCCCTATAAGGAA
     Consensus  (551)   AGAGGGTTTGCGAG TTTGT GC AGCAACCCTAACGCTCCTA AAGGAA 601                                             650
   1111FutA     (585)   CGCTTTTTATGAGGCTTTAAACGCTATTGAGCCAGTTGCTGGGGGAGGGA
915A.cod(MWG)   (334)   --------------------------------------------------
 19C2FutA.cod    (46)   --------------------------------------------------
   26695A.cod   (591)   CGCTTTTTATGACGCTCTAAAATTCCATAGAGCCAGTTACTGGGGGAGGAA
        1182B   (588)   TGCTTTCTATGACGTTTTAAATTCTATAGAGCCAGTTATTGGGGGAGGGA
     1218B.nuc  (588)   TGCTTTCTATGACGCTTTAAATTCTATAGAGCCAGTTATTGGGGGAGGGA
      ORF19C2B  (591)   CGCTTTCTATGAGGCTTTAAATTCTATTGAGCCAGTTACTGGGGGAGGGA
     Consensus  (601)      GCTTT TATGA GCTTTAAATTCTAT GAGCCAGTTA TGGGGGAGGGA 651                                             700
   1111FutA     (635)   GCGTGAAAAACACTTTAGGCTATAATGTCAAAAACAAGAGCGAGTTTTTA
915A.cod(MWG)   (334)   --------------------------------------------------
 19C2FutA.cod    (46)   --------------------------------------------------
   26695A.cod   (641)   GTGTGAGAAACACTTTAGGCTATAAGGTTGGAAACAAAAGCGAGTTTTTA
        1182B   (638)   GCGTGAAAAACACTTTAGGCTATAACATTAAAAACAAGAGCGAGTTTTTA
     1218B.nuc  (638)   GCGTGAAAAACACTTTAGGCTATAACATTAAAAACAAGAGCGAGTTTTTA
      ORF19C2B  (641)   GCGTGAGAAACACTTTAGGCTATAACGTCAAAAACAAAAACGAATTTTTG
     Consensus  (651)   GCGTGA AAACACTTTAGGCTATAA  T AAAAACAA AGCGAGTTTTTA 701                                             750
   1111FutA     (685)   AGCCAATACAAATTCAATCTGTGTTTTGAAAACACTCAAGGCTATGGCTA
915A.cod(MWG)   (334)   --------------------------------------------------
 19C2FutA.cod    (46)   --------------------------------------------------
   26695A.cod   (691)   AGCCAATACAAGTTCAATCTCTGTTTTGAAAACTCGCAAGGTTATGGCTA
        1182B   (688)   AGCCAATACAAATTCAATCTGTGTTTTGAAAACTCACAAGGCTATGGCTA
     1218B.nuc  (688)   AGCCAATACAAATTCAATCTGTGTTTTGAAAACTCACAAGGCTATGGCTA
      ORF19C2B  (691)   AGCCAATACAAGTTCAATCTGTGCTTTGAAAACACTCAAGGCTATGGCTA
     Consensus  (701)   AGCCAATACAA TTCAATCTGTGTTTTGAAAAC C CAAGGCTATGGCTA
```

FIG. 13 (3/6)

```
                         751                                              800
1111FutA       (735) TGTAACTGAAAAGATCATTGACGCTTATTTCAGCCATACCATTCCTATTT
915A.cod(MWG)  (334) --------------------------------------------------
19C2FutA.cod    (46) --------------------------------------------------
26695A.cod     (741) TGTAACCGAAAAAATCCTTGATGCGTATTTTAGCCATACCATTCCTATTT
1182B          (738) TGTAACTGAAAAAATCATTGACGCTTACTTTAGCCATACCATTCCTATTT
1218B.nuc      (738) TGTAACTGAAAAAATCATTGACGCTTACTTTAGCCATACCATTCCTATTT
ORF19C2B       (741) TGTTACTGAAAAAATCATTGACGCTTACTTCAGCCACACCATTCCTATTT
Consensus      (751) TGTAACTGAAAAAATCATTGACGCTTA TT AGCCATACCATTCCTATTT 801                                              850
1111FutA       (785) ATTGGGGG--AGTCC-CAGCGTGGCGAAAGATTTTAACCCTAAGAGTTTT
915A.cod(MWG)  (334) --------------------------------------------------
19C2FutA.cod    (46) --------------------------------------------------
26695A.cod     (791) ATTGGGGG--AGTCC-CAGCGTGGCGAAAGATTTTAACCCTAAAAGTTTT
1182B          (788) ATTGGGGG--AGTCC-TAGCGTGGCACAAGATTTTAACCCTAAGAGTTTT
1218B.nuc      (788) ATTGGGGG--AGTCC-TAGCGTGGCACAAGATTTTAACCCTAAGAGTTTT
ORF19C2B       (791) ATTGGGGGGGAGTCCCTAGCGTGGCGAAAGATTTTAACCCC---------
Consensus      (801) ATTGGGGG  AGTCC AGCGTGGC AAGATTTTAACCCTAA AGTTTT 851                                              900
1111FutA       (832) GTGAATGTCCATGATTTCAACAACTTTGATGAAGCGATTGACTATATCAG
915A.cod(MWG)  (334) --------------------------------------------------
19C2FutA.cod    (46) --------------------------------------------------
26695A.cod     (838) GTGAATGTGCATGATTTCAACAACTTTGATGAAGCGATTGATTATATCAA
1182B          (835) GTGAATGTTTGTGATTTTAAAGATTTTGATGAAGCGATTGATCATGTGCG
1218B.nuc      (835) GTGAATGTTTGTGATTTTAAAGATTTTGATGAAGCGATTGATCATGTGCG
ORF19C2B       (832) --------------------------------------------------
Consensus      (851) GTGAATGT   TGATTT AA  A TTTGATGAAGCGATTGA  AT T 901                                              950
1111FutA       (882) ATACTTGCACACGCACCCAAACGCTTATTTAGACATGCACTATGAAAACC
915A.cod(MWG)  (334) --------------------------------------------------
19C2FutA.cod    (46) --------------------------------------------------
26695A.cod     (888) ATACCTGCACACGCACCCAAACGCTTATTTAGACATGGTCTATGAAAACC
1182B          (885) ATACTTGCACACGCACCCAAACGCTTATTTAGACATGGTTTATGAAAACC
1218B.nuc      (885) ATACTTGCACACGCACCCAAACGCTTATTTAGACATGGTTTATGAAAACC
ORF19C2B       (832) --------------------------------------------------
Consensus      (901) ATAC TGCACACGCACCCAAACGCTTATTTAGACATGC  TATGAAAACC 951                                             1000
1111FutA       (932) CTTTAAACACTATTGATGGGAAAGCTTACTTTTACCAAAATTTGAGTTTT
915A.cod(MWG)  (334) --------------------------------------------------
19C2FutA.cod    (46) --------------------------------------------------
26695A.cod     (938) CTTTAAACACCCTTGATGGGAAAGCTTACTTTTACCAAGATTTGAGTTTT
1182B          (935) CTTTAAACACCCTTGATGGGAAAGCTTACTTTTACCAAAATTTGAGTTTT
1218B.nuc      (935) CTTTAAACACCCTTGATGGGAAAGCTTACTTTTACCAAAATTTGAGTTTT
ORF19C2B       (832) --------------------------------------------------
Consensus      (951) CTTTAAACAC  TTGATGGGAAAGCTTACTTTTACCAA ATTTGAGTTTT
```

FIG. 13 (4/6)

```
                        1001                                              1050
    1111FutA    (982)   AAAAAAATCCTAGATTTTTTTAAAACGATTTTAGAAAACGACACGATCTA
915A.cod(MWG)   (334)   --------------------------------------------------
  19C2FutA.cod   (46)   --------------------------------------------------
    26695A.cod  (988)   AAAAAAATCCTAGATTTTTTTAAAACGATTTTAGAAAACGATACGATTTA
          1182B (985)   AAAAAAATCCTAGATTTTTTTAAAACGATTTTAGAAAACGACACGATTTA
      1218B.nuc (985)   AAAAAAATCCTAGATTTTTTTAAAACGATCTTAGAAAACGACACGATTTA
        ORF19C2B (832)  --------------------------------------------------
        Consensus (1001) AAAAAAATCCTAGATTTTTTTAAAACGAT TTAGAAAACGA ACGAT TA 1051                                              1100
    1111FutA   (1032)   TCACGATAACCC------TTTCATTTTCTATCGTGATTTGAATGAGCCTT
915A.cod(MWG)   (334)   --------------------------------------------------
  19C2FutA.cod   (46)   --------------------------------------------------
    26695A.cod (1038)   TCACAAATTCTCAACATCTTTCATGTGGGAGTACGATCTGCATAAGCCGT
          1182B (1035)  TCACGATAACCC------TTTTATTTTTTATCGTGATTTGAATGAGCCGT
      1218B.nuc (1035)  TCACGATAACCC------TTTTATTTTTTATCGTGATTTGAATGAGCCGT
        ORF19C2B (832)  --------------------------------------------------
        Consensus (1051) TCAC  A   C C       TTT AT T    A    GAT TG AT AGCC T 1101                                              1150
    1111FutA   (1076)   CAGTATCTATTGATGGT---TTGAGGGTTAATTATGATGATTTGAGGGTT
915A.cod(MWG)   (334)   --------------------------------------------------
  19C2FutA.cod   (46)   --------------------------------------------------
    26695A.cod (1088)   TAGTATCCATTGATGAT---TTGAGGGTTAATTATGATGATTTGAGGGTT
          1182B (1079)  TAATATCTATTGATGATGATTTGAGGGTTAATTATGATGATTTGAGGGTT
      1218B.nuc (1079)  TAATATCTATTGATGAT---TTGAGGGTTAATTATGATGATTTGAGGGTT
        ORF19C2B (832)  --------------------------------------------------
        Consensus (1101)  A TATC ATTGATG T   TTGAGGGTTAATTATGATGATTTGAGGGTT 1151                                              1200
    1111FutA   (1123)   AATTATGATGATTTGAGGGTTAATTATGATGATTTGAGGGTTAATTATGA
915A.cod(MWG)   (334)   --------------------------------------------------
  19C2FutA.cod   (46)   --------------------------------------------------
    26695A.cod (1135)   AATTATGACCGGCTTTTACAAAACGCTTCGCCTTTATTAGAACTCTCTCA
          1182B (1129)  AATTATGATGATTTGAGGGTTAATTATGATGATTTGAGGGTTAATTATGA
      1218B.nuc (1126)  AATTATGATGATTTGAGGGTTAATTATGATGATTTGAGGGTTAATTATGA
        ORF19C2B (832)  --------------------------------------------------
        Consensus (1151) AATTATGA    T       AA  T      TTT       G     T T A 1201                                              1250
    1111FutA   (1173)   GCGCCTTTTACAAAACGCCTCGCCTTTATTAGAACTCTCTCAAAACACCA
915A.cod(MWG)   (334)   --------------------------------------------------
  19C2FutA.cod   (46)   --------------------------------------------------
    26695A.cod (1185)   AAACACCACTTTTAAAATCTATCGCAAAGCTTATCAAAAATCCTTGCCTT
          1182B (1179)  TGATTTGAGGGTTAATTATGATGATTTGAGGGTTAATTATGATGATTTGA
      1218B.nuc (1176)  TGATTTGAGGGTTAATTATGATGATTTGAGGGTTAATTATGATGATTTGA
        ORF19C2B (832)  --------------------------------------------------
        Consensus (1201)                      AA
```

FIG. 13 (5/6)

```
                           1251                                          1300
    1111FutA     (1223) CTTTTAAAATCTATCGCAAAGCTTATCAAAAATCCTTGCCTTTGTTGCGT
 915A.cod(MWG)   (334)  --------------------------------------------------
  19C2FutA.cod   (46)   --------------------------------------------------
    26695A.cod   (1235) TGTTGCGCGCGGTGAGAAAGTTGGTTAAAAAATTGGGTTTGTAA------
         1182B   (1229) GGGTTAATTATGATGATTTGAGGGTTAATTATGATGATTTGAGGGTTAAT
     1218B.nuc   (1226) GGGTTAATTATGATGATTTGAGGGTTAATTATGATGATTTGAGGGTTAAT
       ORF19C2B  (832)  --------------------------------------------------
     Consensus   (1251)       T              T A   A 1301                                          1350
    1111FutA     (1273) GCCATAAGGAGATGGGTTAAAAAGTAA-----------------------
 915A.cod(MWG)   (334)  --------------------------------------------------
  19C2FutA.cod   (46)   --------------------------------------------------
    26695A.cod   (1279) --------------------------------------------------
         1182B   (1279) TATGATGATTTGAGGGTTAATTATGATGATTTGAGGGTTAATTATGAGCG
     1218B.nuc   (1276) TGTGATGATTTGAGGGTTAATTATGATGATTTGAGGGTTAATTATGAGCG
       ORF19C2B  (832)  --------------------------------------------------
     Consensus   (1301)

1351                                          1400
    1111FutA     (1300) --------------------------------------------------
 915A.cod(MWG)   (334)  --------------------------------------------------
  19C2FutA.cod   (46)   --------------------------------------------------
    26695A.cod   (1279) --------------------------------------------------
         1182B   (1329) GCTCTTACAAAACGCCTCGCCTTTATTAGAACTCTCTCAAAACACCACTT
     1218B.nuc   (1326) GCTCTTACAAAACGCCTCGCCTTTATTAGAACTCTCTCAAAACACCACTT
       ORF19C2B  (832)  --------------------------------------------------
     Consensus   (1351)

1401                                          1450
    1111FutA     (1300) --------------------------------------------------
 915A.cod(MWG)   (334)  --------------------------------------------------
  19C2FutA.cod   (46)   --------------------------------------------------
    26695A.cod   (1279) --------------------------------------------------
         1182B   (1379) TTAAAATCTATCGCAAAGCTTATCAAAAATCCTTACCTTTGTTGCGTGCG
     1218B.nuc   (1376) TTAAAATCTATCGCAAAGCTTATCAAAAATCCTTACCTTTGTTGCGTGCG
       ORF19C2B  (832)  --------------------------------------------------
     Consensus   (1401)

1451           1483
    1111FutA     (1300) ---------------------------------
 915A.cod(MWG)   (334)  ---------------------------------
  19C2FutA.cod   (46)   ---------------------------------
    26695A.cod   (1279) ---------------------------------
         1182B   (1429) GCGAGAAAGTTGATTAAAAAATTGGGTTTGTAA
     1218B.nuc   (1426) GCGAGAAAGTTGATTAAAAAATTGGGTTTGTAA
       ORF19C2B  (832)  ---------------------------------
     Consensus   (1451)
```

FIG. 13 (6/6)

Oligo Structures

Lacto-N-neo-Tetraose (LNnT)

Galβ1-4GlcNAcβ1-3Galβ1-4Glc

Lacto-N-Fucopentaose III (LNFP III)

Galβ1-4GlcNAcβ1-3Galβ1-4Glc
              |
              3
              |
           1αFucose

FIG. 14

Linkage Analysis by GC/MS

The samples were methylated, hydrolyzed, reduced with sodium borodeuteride, acetylated and analyzed by GC/MS along with samples of LNnT and LNF3.

↑ A Glc vs. Glc-NAc value close to 1 favors fucosylation of Glc-NAc.
↑ A Glc vs. Glc-NAc value close to 0 favors fucosylation of Glc

| *H. Pylori* Strain | Glc vs. Glc-NAc |
|---|---|
| 915A2 | 0.982 |
| 19C2A5 | 0.040 |
| 1111A2 | 0.975 |
| 19C2B1 | 0.991 |
| 1182B3 | 0.983 |

FIG. 15

1 Liter LNFIII Synthesis

| Batch Number | Resin Type | Total Yield | Actual Percent Recovery |
|---|---|---|---|
| 1-02 | MR3 $NH_4HCO_3$ column (1ml resin/1ml synthesis) | 1.567 g | 61% |
| 2-02 | MR3 $NH_4HCO_3$ column (1ml resin/1ml synthesis) | 1.760 g | 68% |
| 3-02 | Dowex1/Dowex 50 (2ml resin/1ml synthesis) | 1.221 g | 47% |

FIG. 16

FIG. 17
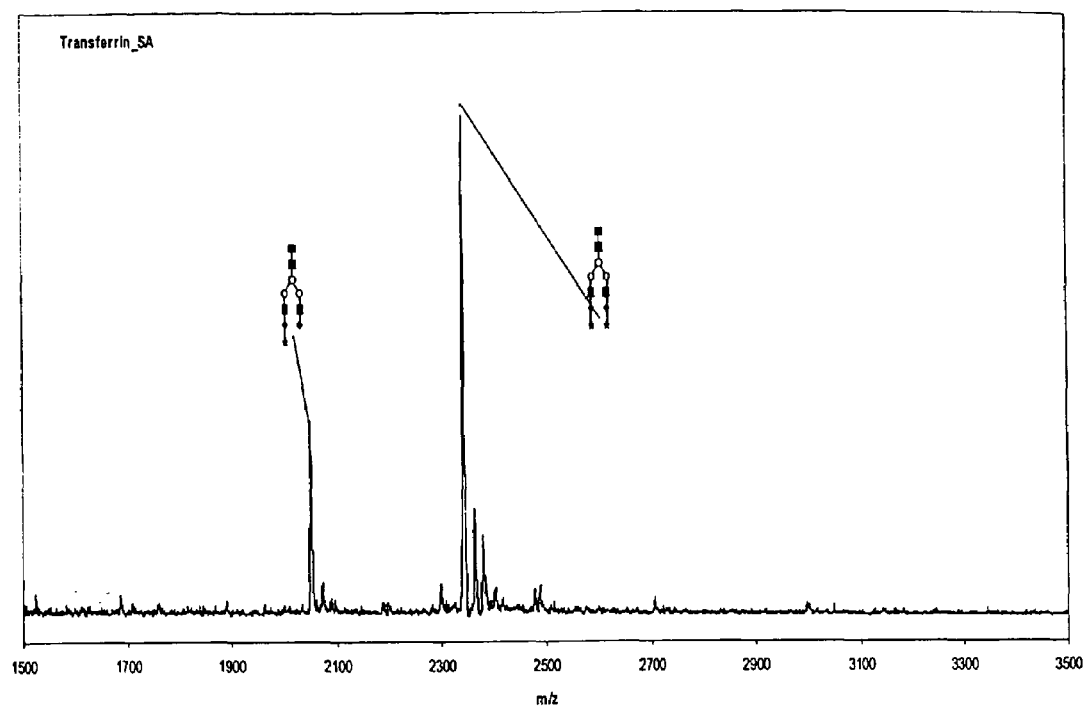
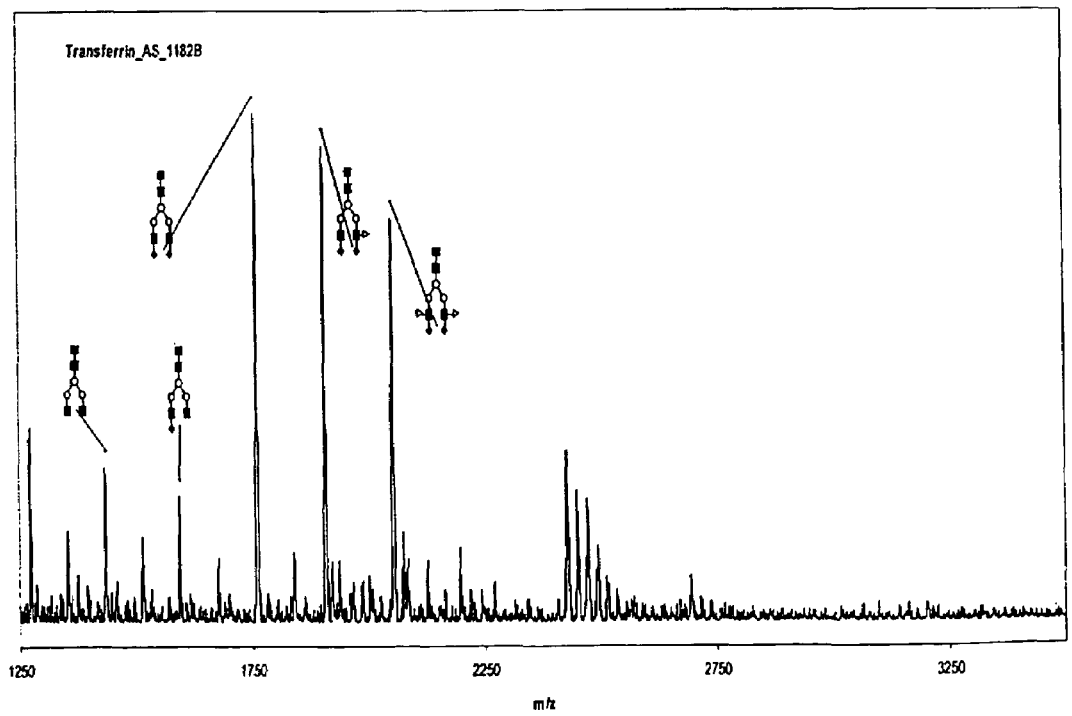

FIGURE 18

Strain 1111FutB fucosyltransferase nucleotide coding sequence (SEQ ID NO:15)

```
ggatccCGAGCGACCAATCATTACAGGGATTTATTGCATTTAGATGCGGCTTTCAGTAACACGCTGATCGT
GGAAAATAACGCCTTAAACGGCTTGGTTACCGGGCATATGATGTTTTCACATTCTAAAGGCGAAATGCTCC
TCGCTTTGCAACGCTCGTTGAATATCAGTAAAGATCGCACTTTAGTCGTGGGCGATGGGGCGAATGATTTG
AGCATGTTCAAACATGCCCATATTAAAATCGCTTTCAACGCTAAAGAGGTTTTAAAACAGCACGCCACGCA
TTGCATCAATGAGCCTAATCTAGCCCTAATCAAGCCTTTGATTTACAAAAATTTTTTTTGTAAAATTCCCT
TTAAAAGGATAGCCatgttccaaccccctattagacgcttatgtagaaagcgcttccattgaaaaaatggcc
tctaaatctcccccccccctaaaaatcgctgtggcgaattggtggggagatgaagaaattaaagaatttaa
aaagagcgttctttattttatctttagccaacgctacacaatcgccctccaccaaaacccaatgaatttt
cagatctagtctttagcaatcctcttggatcagctagaaaaatcttatcgtatcaaaacgctaaaagagtg
ttttacaccggtgaaaatgaagtccctaacttcaacctctttgattacgccataggctttgatgaattgga
ttttagagatcgttatttgaggatgcctttatattatgataggctacaccataaagccgagagcgtgaatg
acaccacttcgccctacaaactcaaagacaacagcctttatactttaaaaaaaccctcccatcaatttaaa
gaaaaccaccctaatttagcgcagtcgtgaatgatgagagcgatcctttgaaaagaggggttgtgagcttt
gtagcgagcaacgctaacgctcctatgagaaacgccttttatgacgctttaaattctattgagccagttac
tgggggagggagcgtgaaaaacactttaggctataacgtcaaaaacaagagcgagttttaagccaataca
agttcaacctgtgttttgaaaactcacaaggctatggctatgtaaccgagaagatccttgacgcttactt
agccacaccattcctatttattgggggagtcctagcgtggcgaaagattttaaccctaaagagtttgtgaa
tgtccatgatttcaacaactttgatgaagcgatagattatatcaaatacttgcacacgcacccaaacgctt
atttagacatgctctatgaaaacccttaaacgcccttgatgggaaagcttacttttaccaggatttgagt
tttaaaaaaatcctagcttttttaaaacgattttagaaaacgatacgatttatcacaaatcctcaacatc
tttcatgtggagtgcgatctcgatgagccgttagcgtctattgatgatttgagggttaattatgatgattt
gagggttaattatgatgatttgagggttaattatgatgatttgagggttaattatgatgatttgagggtta
attatgatgatttgagggttaattatagcgcctttgcaaaacgcttcacctttattggaattatcccaaa
acacctcttttaaaatctatcgcaaagcctatcaaagcctatcaaaaatccttacccttattgcgcgccat
aaGGAGATGGGTTAAAAAGTAAGGTGTCTTTTAAGACTGGTTGAGAAATTGAAGCGCTATTTTAAAATGCG
CTAACGCTTCTTTTTTGAGCGTGGGGTTTTTGAGCATGTCCTCTAAAGCATGGGCGCTTAAAAAATGTTTG
GATTTTAAAGACACGATGCGCCCAAAGGATTCTTCTTTAGAAAGGTTTAAAAGGCGTTTGGGCAAAATCTC
GCCAAATACGATAATGACTTTTGAAGCGCTGTTGTCTAATTGCCAGGTCGgaattc
```

Strain 1111FutB fucosyltransferase amino acid sequence (SEQ ID NO:16)

```
MFQPLLDAYVESASIEKMASKSPPPLKIAVANWWGDEEIKEFKKSVLYFIFSQRYTIALHQNPNEFSDLVF
SNPLGSARKILSYQNAKRVFYTGENEVPNFNLFDYAIGFDELDFRDRYLRMPLYYDRLHHKAESVNDTTSP
YKLKDNSLYTLKKPSHQFKENHPNLCAVVNDESDPLKRGVVSFVASNANAPMRNAFYDALNSIEPVTGGGS
VKNTLGYNVKNKSEFLSQYKFNLCFENSQGYGYVTEKILDAYFSHTIPIYWGSPSVAKDFNPKEFVNVHDF
NNFDEAIDYIKYLHTHPNAYLDMLYENPLNALDGKAYFYQDLSFKKILAFFKTILENDTIYHKSSTSFMWE
CDLDEPLASIDDLRVNYDDLRVNYDDLRVNYDDLRVNYDDLRVNYERLLQNASPLLELSQNTSF
KIYRKAYQKPIKNPYPYCAP
```

FIGURE 19

Strain 802FutA fucosyltransferase nucleotide coding sequence (SEQ ID NO:17)

```
ggatccCGGCGTGAATTACTACCTTTCTGGCTTGCACAGCTATGCCGCAGGCGATCCCTTGCCTATCCCTA
CTTTCTTATACTTTTTGGTAGCGATACCTTTTGCTCTCGTGATTTTGGCTTATTTCAAACGCCATTTGAGT
TTGCCTAAATTGGTTTAAAGGATAGCCatgTTCCAGCCCTTACTAGACGCCTTTATAGAAAGTGCTTCAAT
TAAAAAAATGCCTCTGAGTTACCCCCCCCTAAAAAATCGCTGTGGCGAATTGGTGGGGAGGCGCTGAAGAAT
TTAAAAAGAGCGCTATGTATTTCATCCTAAGCCAACGCTACACAATCACCCTCCACCAAAACCCCAACGAA
CCCTCCGATCTCGTCTTTGGCAGTCCTATTGGAGCAGCCAGAAAAATCCTATCCTACCAAAACACTAAAAG
AGTGTTTTACGCCGGTGAAAATGAAGTCCCTAATTTCAACCTCTTTGATTACGCCATAGGCTTTGATGAAT
TGGATTTTAGAGATCGTTATTTGAGAATGCCTTTATATTATGATAGACTACACCATAAAGCCGAGAGCGTG
AATGACACCACCGCGCCTTACAAGATTAAACCTGACAGCCTTTATACTTTAAAAAAACCCTCCCATCATTT
TAAAGAAAAACACCCCCATTTATGCGCAGTAGTGAATGATGAGAGCGATCCTTTGAAAAGAGGGTTTGCGA
GTTTTGTCGCAAGCAACCCTAACGCTCCTAAAAGGAACGCCTTCTATGACGCTTTAAATTCTATTGAGCCA
GTTACTGGGGAGGGAGCGTGAAAAACACTTTAGGCTATAAAGTTGGAAACAAAAACGAGTTTTTAAGCCA
ATACAAATTCAATCTGTGTTTTGAAAACTCTCAAGGCTATGGCTATGTAACCGAAAAAATCATTGACGCTT
ACTTTAGCCATACCATTCCTATTTATTGGGGAGTCCTAGCGTGGCGAAAGATTTTAACCCTAAGAGTTTT
GTGAATGTGCATGATTTTAAAAACTTTGATGAAGCGATTGATTACGTGAGATACTTGCACACGCACCCAAA
CGCTTATTTAGACATGCTCTATGAAAACCCTTTAAACACCCTTGATGGGAAAGCTTACTTTTACCAAGATT
TGAGTTTTAAAAAAATCCTAGATTTTTTTAAAACGATTTTAGAAAACGATACGATCTATCACAATAACCCT
TTTGTTTTCTATCGTGATTTGAATGAGCCGTTAGTATCTATTGATGATTTGAGAGCCGATTATAATAATTT
GAGAGCCGATTATAATAATTTGAGAGCCGATTATAATAATTTGAGAGCCGATTATAATAATTTGAGAGCCG
ATTACGATCGCCTGTTACAAAACCGTTCGCCTTTGTTGGAACTCTCTCAAAACACCACTTTTAAAATCTAT
CACAAAGCTTATCACAAATCCTTACCTTTGTTGCGTGCCATAAGGAGATGGGTTAAAAAATTGGGTTTGta
aAATTGGGGGTAATCAAACCCCTTGCGCTATCATCGCAGACGCCACTTTTCTAAAACCAGCGATATTAGCC
CCTAAAACAAAATTAGTAGGGTCTTTAAACTCTTTAGCGGTTTGAGAGACATTTTTATAAATCTCTTTCAT
GATGTGGTGTAATTTCGCATCCACCACTTCAAAACTCCAAGGGTGCATGCTCGCGTTTTGCGCCATTTCCA
AGCCGCTCACGCTCACCCCCCCAGCATTAGCCGCCTTGCCTATACCATAAGAAATCTTAGCCTGTAAAAAC
AATTCAATCGCTTCATTGCTTGAGGGCATGTTCGCCCCTTCAGCCACGCATTTGCACCCATTAGAAAGGAG
GGTTTTGCGgaattc
```

Strain 802FutA fucosyltransferase amino acid sequence (SEQ ID NO:18)

```
MFQPLLDAFIESASIKKMPLSYPPLKIAVANWWGGAEEFKKSAMYFILSQRYTITLHQNPNEPSDLVFGSP
IGAARKILSYQNTKRVFYAGENEVPNFNLFDYAIGFDELDLRDRYLRMPLYYDRLHHKAESVNDTTAPYKI
KPDSLYTLKKPSHHFKEKHPHLCAVVNDESDPLKRGFASFVASNPNAPKRNAFYDALNSIEPVTGGGSVKN
TLGYKVGNKNEFLSQYKFNLCFENSQGYGYVTEKIIDAYFSHTIPIYWGSPSVAKDFNPKSFVNVHDFKNF
DEAIDYVRYLHTHPNAYLDMLYENPLNTLDGKAYFYQDLSFKKILDFFKTILENDTIYHNNPFVFYRDLNE
PLVSIDDLRADYNNLRADYNNLRADYNNLRADYDRLLQNRSPLLELSQNTTFKIYHKAYHKSLP
LLRAIRRWVKKLGL
```

FIGURE 20

Strain 948FutA fucosyltransferase nucleotide coding sequence (SEQ ID NO:19)

ggatccCGGCGTGAATTACTACCTTTCTGGCTTGCACAGCTATGCCGCAGGCGATCCCTTGCCCATCCCCA
CTTTCTTATACTTTTTAATAGCGATACCTTTTGCTCTCGTGATCTTGGCGTATTTCAAACGCCATTTGAGT
TTGCCTAAATTGGTTTAAAGGATAAAAatgttccagcccttactagacgctttcatagacagcacccattt
agatgaaacaacccataagcccccattaaatgtagccctagccaattggtggcccttaaaaaatagcgaaa
aaaaaggattcagagacttcattttgcatttcatcctaaaacaacgctataaaatcattctgcacagcaac
cctaatgaaccctcagatctagtctttggcaatcctttggaacaagccagaaaaatcttatcttatcaaaa
cactaaacgagtgttttacaccggcgaaaatgaagtgcctaatttcaatctctttgattacgccataggct
ttgatgaattggattttaacgatcgctatttgagaatgcctttgtattacgcctatttgcattataaagcc
atgcttgttaatgacaccacttcgccctataaactcaaagccctttatactttaaaaaaaccttcccataa
atttaaagaaaaccaccccaatttatgtgcgctaatccataacgagagcgatccttggaaaagagggtttg
ccagttttgtcgcaagcaatcctaacgctcccatcagaaacgctttctatgacgctttaaatgctattgag
ccagtggctagtggagggagtgtgaaaaacactctaggctataaggtcaaaaacaaaaacgaatttttaag
ccaatacaagttcaacctctgttttgaaaactcacaaggctatggctatgtaaccgaaaaaatccttgatg
cgtatttcagccacactatccctatttattgggggagtcccagcgtggcgaaagatttaaccctaaaagt
tttgtgaatgtgcatgatttcaacaactttgatgaagcgattgattatatcagatatttacacgcgcacca
aaacgcttatttagacatgctttatgaaaaccccttaaacaccattgatgggaaagcgggttttaccaag
atttgagttttgaaaagatcttagatttttttcaaaaacattcttgaaaacgatacgatttatcattgcaat
gatgcccattattctgctcttcatcgtgatttgaatgagccgttagtgtctgttgatgatttgagaagaga
tcatgatgatttgagggttaattatgatgatttgagagttaattatgatgatttgagagttaattatgatg
atttgagagttaattatgatgatttgagagttaattatgatgatttgagaagagatcatgatgatttgaga
agagatcatgaacgcctcttatcaaaggctacccctttattggagctatcccaaaacacctcttttaaaat
ctatcgcaaagcttatcaaaagtccttaccctgttgcgtgccataaAAACAATTCAATCGCTTCATTGCT
TGAGGGCATGTTCGCCCCTTCAGCCACGCATTTGCACCCATTAGAAAGGAGGGTTTTGCGGAATTCCTGCA
GCCCGGGGGATCCCCCGGGCTGCAGgaattc

Strain 948FutA fucosyltransferase amino acid sequence (SEQ ID NO:20)

MFQPLLDAFIDSTHLDETTHKPPLNVALANWWPLKNSEKKGFRDFILHFILKQRYKIILHSNPNEPSDLVF
GNPLEQARKILSYQNTKRVFYTGENEVPNFNLFDYAIGFDELDFNDRYLRMPLYYAYLHYKAMLVNDTTSP
YKLKALYTLKKPSHKFKENHPNLCALIHNESDPWKRGFASFVASNPNAPIRNAFYDALNAIEPVASGGSVK
NTLGYKVKNKNEFLSQYKFNLCFENSQGYGYVTEKILDAYFSHTIPIYWGSPSVAKDFNPKSFVNVHDFNN
FDEAIDYIRYLHAHQNAYLDMLYENPLNTIDGKAGFYQDLSFEKILDFFKNILENDTIYHCNDAHYSALHR
DLNEPLVSVDDLRRDHDDLRVNYDDLRVNYDDLRVNYDDLRVNYDDLRVNYDDLRRDHDDLRRDHERLLSK
ATPLLELSQNTSFKIYRKAYQKSLPLLRAI

FIGURE 21

Strain 955FutA fucosyltransferase nucleotide coding sequence (SEQ ID NO:21)

```
ggatccCGAGCGACCAATCATTACAGGGATTTATTAAATTTAGATGTGGCTTTCAGTAACACGCTGATAGT
GGAAAATGGTGCCTTAAACGGCTTGGTTACGGGGCATATGATGTTTTCACACTCTAAAGGCGAAATGCTTC
TCGCCCTACAACGCTTGCTAAATATCAGTGAAACGAGCACTTTAGTTGTGGGCGATGGAGCGAATGACTTG
AGCatgTTCAAACATGCCCATATTAAAATCGCTTTCAACGCTAAAGAGGTTTTAAAACAACACGCCACGCA
TTGCATCAATGAGCCTGATTTAGCCCTAATCAAGCCTTTGATTTAAAAAATTTTTTTTGTAAAATACTCCT
TTAAAGGATAAAGATGTTCCAGCCCCTATTAGATGCCTTCATAGAAAGCGCTTCAATTAAAAAAAAATTGC
CTCTAAATCTCCCCCCCCCTAAAAATCGCTGTGGCGAATTGGTTTAACGGCACTAAAGAATTTAAAGCGAG
CGTTCTTTATTTCATCCTAAAACAACGCTATAAAATCATTCTGCACAGCAACCCTAATGAACCCTCAGATC
TAGTCTTTGGCAATCCTTTGGAACAAGCCAGAAAAATCTTATCTTATCAAACACTAAACGAGTGTTTTAC
ACCGGCGAAAATGAAGTGCCTAATTTCAATCTCTTTGATTACGCCATAGGCTTTGATGAATTGGATTTTAA
CGATCGCTATTTGAGAATGCCTTTGTATTACGCCTATTTGCATTATAAAGCCATGCTTGTTAATGACACCA
CTTCGCCCTATAAACTCAAAGCCCTTTATACTTTAAAAAAACCTTCCCATAAATTTAAAGAAAACCACCCC
AATTTATGTGCGCTAATCCATAACGAGAGCGATCCTTGGAAAAGAGGGTTTGCCAGTTTTGTCGCAAGCAA
TCCTAACGCTCCCATCAGAAACGCTTTCTATGACGCTTTAAATGCTATTGAGCCAGTGGCTAGTGGAGGGA
GTGTGAAAAACACTCTAGGCTATAAGGTCAAAAACAAAAACGAATTTTTAAGCCAATACAAGTTCAACCTC
TGTTTTGAAAACTCACAAGGCTATGGCTATGTAACCGAAAAAATTCCTTGATGCGTATTTCAGCCACACTA
TCCCTATTTATTGGGGGAGTCCCAGCGTGGCGAAAGATTTTAACCCTAAAAGTTTTGTGAATGTGCATGAT
TTCAACAACTTTGATGAAGCGATTGATTATATCAGATATTTACACGCGCACCAAAACGCTTATTTAGACAT
GCTTTATGAAAACCCCTTAAACACCATTGATGGGAAAGCGGGTTTTTACCAAGATTTGAGTTTTGAAAAGA
TCTTAGATTTTTTCAAAAACATTCTTGAAAACGATACGATTTATCATTGCAATGATGCCCATTATTCTGCT
CTTCATCGTGATTTGAATGAGCCGTTAGTGTCTGTTGATGATTTGAGAAGAGATCATGATGATTTGAGGGT
TAATTATGATGATTTGAGAAGAGATCATGAACGCCTCTTATCAAAGGCTACCCCTCTTTTGGAGCTATCCC
AAAACACCTCTTTTAAAATCTATCGCAAAGCTTATCAAAAGTCCTTACCCTTGTTGCGTGCCATAAGGAAG
TGGGTTAAAAAATAAGGCGTATTTTAAGACTGATGAAGAAATTGAAGCGCTATTTTAAAATGCGCTAACGC
TTCTTTTTTGAGCGTGGGGTTTTTGAGCATGTCCTCTAAAGCATGGGTGCTTAAAAAATGTTTTGTTTTTA
AAGACACGATGCGTCCAAAGGATTCTTCTTTAGAAAGGTTTAAAAGGCGTTTGGGCAAAATCTCGCCAAAT
ACCACAATGACTTTTGAAGCGCTGTTGTCTAATTGCCAGGTCGgaattc
```

Strain 955FutA fucosyltransferase amino acid sequence (SEQ ID NO:22)

```
MFKHAHIKIAFNAKEVLKQHATHCINEPDLALIKPLIFKIFFVKYSFKG.RCSSPY.MPS.KALQLKKNCL
.ISPPLKIAVANWFNGTKEFKASVLYFILKQRYKIILHSNPNEPSDLVFGNPLEQARKILSYQNTKRVFYT
GENEVPNFNLFDYAIGFDELDFNDRYLRMPLYYAYLHYKAMLVNDTTSPYKLKALYTLKKPSHKFKENHPN
LCALIHNESDPWKRGFASFVASNPNAPIRNAFYDALNAIEPVASGGSVKNTLGYKVKNKNEFLSQYKFNLC
FENSQGYGYVTEKIP.CVFQPHYPYLLGESQRGERF.P.KFCECA.FQQL..SD.LYQIFTRAPKRLFRHA
L.KPLKHH.WESGFLPRFEF.KDLRFFQKHS.KRYDLSLQ.CPLFCSSS.FE.AVSVC..FEKRS..FEG.
L..FEKRS.TPLIKGYPSFGAIPKHLF.NLSQSLSKVLTLVACHKEVG.KIRRILRLMKKLKRYFKMR.RF
FFERGVFEHVL.SMGA.KMFCF.RHDASKGFFFRKV.KAFGQNLAKYHNDF.SAVV.LPGRN
```

FIGURE 22

Strain 1218FutA fucosyltransferase nucleotide coding sequence (SEQ ID NO:23)
```
ggatccTCTGGCTTGCACAGCTATGCCGCAGGCGATCCCTTGCCTATCCCTACTTTCTTATACCTTTTTGG
TAGCGATACCTTTCGCTCTCGTGATCTTGGCTTATTTCAAACGCCATTTGAGTTTGCCTAAATTGGTTTAA
AGGATAACCATGTTCCAACCCCTATTAGACGCTTATATAGAAAGCGCTTCCATTGAAAAAATTACCTCTAA
ATCTCCCCCCCCCCTAAAAATCGCTGTGGCGAATTGGTGGGGAGATGAAGAGGTTGAAGAATTTAAAAAGA
ACATTCTTTATTTTATTCTCAGTCAGCATTACACAATCACCCTCCACCAAAACCCCAACGAACCCTCCGAT
CTCGTCTTTGGCAGTCCTATTGGATCAGCCAGAAAAATCTTATCCTATCAAAACGCAAAAAGAGTGTTTTA
CACCGGTGAAAACGAATCGCCTAATTTCAACCTCTTTGATTACGCCATAGGCTTTGATGAATGGATTTTAG
AGATCGTTATTTAAGAATGCCTTTATATTATGATAGACTACACCATAAAGCCGAGAGCGTGAATGACACCA
CTTCGCCTTACAAACTCAAACCTGACAGCCTTTATGCTTTAAAAAAACCCTCCCATCATTTTAAAGAAAAC
CACCCCAATTTATGCGCAGTAGTGAACAATGAGAGCGATCCTTTGAAAAGAGGGTTTGCGAGTTTTGTAGC
GAGCAACCCTAACGCTCCTAAAAGGAATGCTTTCTATGACGCTTTAAATTCTATAGAGCCAGTTATTGGGG
GAGGGAGCGTGAAAAACACTTTAGGCTATAACATTAAAAACAAGAGCGAGTTTTAAGCCAATACAAATTC
AATCTGTGTTTTGAAAACTCACAAGGCTATGGCTATGTAACTGAAAAAATCATTGACGCTTACTTTAGCCA
TACCATTCCTATTTATTGGGGGAGTCCTAGCGTGGCACAAGATTTTAACCCTAAGAGTTTTGTGAATGTTT
GTGATTTTAAAGATTTTGATGAAGCGATTGATCATGTGCGATACTTGCACACGCACCCAAACGCTTATTTA
GACATGCTTTATGAAAACCCTTTAAACACCCTTGATGGGAAAGCTTACTTTCCAAAATTTGAGTTTTAAAA
AAATCCTAGATTTTTTAAAACGATCTTAGAAAACGACACGATTTATCACGATAACCCTTTTATTTTTTAT
CGTGATTTGAATGAGCCGTTAATATCTATTGATGATTTGAGGGTTAATTATGATGATTTGAGGGTTAATTA
TGATGATTTGAGGGTTAATTATGATGATTTGAGGGTTAATTATGATGATTTGAGGGTTAATTATGATGATT
TGAGGGTTAATTATGATGATTTGAGGGTTAATTATGATGATTTGAGGGTTAATTATGATGATTTGAGGGTT
AATTGTGATGATTTGAGGGTTAATTATGATGATTTGAGGGTTAATTATGAGCGGCTCTTACAAAACGCCTC
GCCTTTATTAGAACTCTCTCAAAACACCACTTTTAAAATCTATCGCAAAGCTTATCAAAAATCCTTACCTT
TGTTGCGTGCGGCGAGAAAGTTGATTAAAAAATTGGGTTTGTAAAATTGGGGGTAATCAAACCCCTTGCGC
TATCATCGCAGACGCCACCTTTCTAAAACCAGCGATATTAGCCCCTAAAACAAAATTAGTAGGGTCTTTAA
ACTCTTTAGCGGTTTGAGAGACATTCTTATAAgaattc
```

Strain 1218FutA fucosyltransferase amino acid sequence (SEQ ID NO:24)
```
MFQPLLDAYIESASIEKITSKSPPPLKIAVANWWGDEEVEEFKKNILYFILSQHYTITLHQNPNEPSDLVF
GSPIGSARKILSYQNAKRVFYTGENESPNFNLFDYAIGFDEWILEIVI.ECLYIMIDYTIKPRA.MTPLRL
TNSNLTAFML.KNPPIILKKTTPIYAQ..TMRAIL.KEGLRVL.RATLTLLKGMLSMTL.IL.SQLLGEGA
.KTL.AITLKTRASF.ANTNSICVLKTHKAMAM.LKKSLTLTLAIPFLFIGGVLAWHKILTLRVL.MFVIL
KILMKRLIMCDTCTRTQTLI.TCFMKTL.TPLMGKLTFQNLSFKKILDFFKTILENDTIYHDNPFIFYRDL
NEPLISIDDLRVNYDDLRVNYDDLRVNYDDLRVNYDDLRVNYDDLRVNYDDLRVNYDDLRVNYDDLRVNCD
DLRVNYDDLRVNYERLLQNASPLLELSQNTTFKIYRKAYQKSLPLLRAARKLIKKLGL.NWG.SNPLRYHR
RRHLSKTSDISP.NKISRVFKLFSGLRDILIRIRYQAYRYRRPRGGAR
```

H. PYLORI FUCOSYLTRANSFERASES

FIELD OF INVENTION

This invention provides nucleic acid and amino acid sequences of fucosyltransferases from *Helicobactor pylori*. The invention also provides methods to use the fucosyltransferases to synthesize oligosaccharides, glycoproteins, and glycolipids.

BACKGROUND OF THE INVENTION

Although in recent years significant advances have been made in carbohydrate chemistry, there are still substantial difficulties associated with the chemical synthesis of glycoconjugates, particularly with the formation of the ubiquitous β-1,2-cis-mannoside linkage found in mammalian oligosaccharides. Moreover, regio- and stereo-chemical obstacles must be resolved at each step of the de novo synthesis of a carbohydrate.

In view of the difficulties associated with the chemical synthesis of glycoconjugates, the use of glycosyltransferases to enzymatically synthesize glycoproteins and glycolipids, having desired oligosaccharide moieties, is a promising approach to preparing such glycoconjugates. Enzyme-based syntheses have the advantages of regioselectivity and stereoselectivity, and can be performed using unprotected substrates. Moreover, glycosyltransferases have been used to enzymatically modify oligosaccharide moieties and have been shown to be very effective for producing specific products with good stereochemical and regiochemical control. The glycosyltransferases of interest include fucosyltransferases, sialyltransferases, galactosyltransferases, and N-acetylglucosaminyltransferases. For a general review, see, Crout et al., *Curr. Opin. Chem. Biol.* 2: 98-111 (1998) and Arsequell, et al., *Tetrahedon: Assymetry* 10: 2839 (1997).

Many glycoproteins and glycolipids require the presence of a particular glycoform, or the absence of a particular glycoform, in order to exhibit a particular biological activity. For example, many glycoprotein and glycolipids require the presence of particular fucosylated structures in order to exhibit biological activity. Intercellular recognition mechanisms often require a fucosylated oligosaccharide. For example, a number of glycoproteins that function as cell adhesion molecules, including P-selectin, L-selectin, and E-selectin, bind specific cell surface fucosylated carbohydrate structures such as the sialyl Lewis-x and the sialyl Lewis-a structures. In addition, the specific carbohydrate structures that form the ABO blood group system are fucosylated. The carbohydrate structures in each of the three groups share a Fucα1,2Galβ1-disaccharide unit. In blood group O structures, this disaccharide is the terminal structure; whereas the blood group A structure is formed by an α1,3 GalNAc transferase that adds a terminal GalNAc residue to the disaccharide; and the blood group B structure is formed by an α1,3 galactosyltransferase that adds a terminal galactose residue.

The Lewis blood group structures are also fucosylated. For example the Lewis-x and Lewis-a structures are Galβ1,4(Fucα1,3)GlcNac and Galβ1,3(Fucα1,4)GlcNac, respectively. Both these structures can be further sialylated (NeuAcα2,3-) to form the corresponding sialylated structures. Other Lewis blood group structures of interest are the Lewis-y and Lewis-b structures which are Fucα1,2Galβ1,4(Fucα1,3)GlcNAcβ-OR and Fucα1,2Galβ1,3(Fucα1,4)GlcNAc-OR, respectively. For a description of the structures of the ABO and Lewis blood group structures and the enzymes involved in their synthesis see, *Essentials of Glycobiology*, Varki et al. eds., Chapter 16 (Cold Spring Harbor Press, Cold Spring Harbor, N.Y., 1999).

Specifically, fucosyltransferases have been used in synthetic pathways to transfer a fucose residue from guanosine-5'-diphosphofucose to a specific hydroxyl of a saccharide acceptor. A variety of donor substrates and acceptor substrates are known (see Guo et al., *Applied Biochem. and Biotech.* 68: 1-20 (1997)). For example, Ichikawa prepared sialyl Lewis-x by a method that involves the fucosylation of sialylated lactosamine with a cloned fucosyltransferase (Ichikawa et al., *J. Am. Chem. Soc.* 114: 9283-9298 (1992)). Lowe has described a method for expressing non-native fucosylation activity in cells, thereby producing fucosylated glycoproteins on cell surfaces, etc. (U.S. Pat. No. 5,955,347).

Thus, since the biological activity of many commercially important recombinantly and transgenically produced glycoproteins and glycolipids depends upon the presence of a particular glycoform, or the absence of a particular glycoform, a need exists for an efficient method for enzymatically synthesizing glycoconjugates having the desired fucoylated oligosaccharide moieties. In additoin, there is a need for the efficient production of focosylated oligosaccharides. The present invention fulfills these and other needs.

BRIEF SUMMARY OF THE INVENTION

The present invention provides α-1,3/4-fucosyltranferase proteins and nucleic acids from *H. pylori*. The α-1,3/4-fucosyltranferase proteins catalyzes the transfer of a fucose residue from a donor substrate to an acceptor substrate. In one embodiment, the invention provides α-1,3/4-fucosyltranferase nucleic acids with greater than 90% identity to a nucleotide sequence selected from SEQ ID NO:1, 3, or 7 and that encode α-1,3/4-fucosyltranferase proteins that transfer fucose to GlcNAc residues. In another embodiment, the invention provides α-1,3/4-fucosyltranferase nucleic acids with greater than 90% identity to SEQ ID NO:5 and that encode α-1,3/4-fucosyltranferase proteins that transfer fucose to Glucose residues.

In another embodiment the α-1,3/4-fucosyltranferase nucleic acid is selected from SEQ ID NO:1, 3, 5 or 7. The invention also provides nucleic acid sequences that encode α-1,3/4-fucosyltranferase proteins, including SEQ ID NO:2, 4, 6, or 8 and that catalyze the transfer of fucose to an N-acetylglucosamine residue or to a glucose residue. In one aspect the encoded α-1,3/4-fucosyltransferase also includes an amino acid tag.

In a further aspect the invention provides an isolated nucleic acid that includes SEQ ID NO:11, and that encodes an α-1,3/4-fucosyltransferase protein that catalyzes the transfer of a fucose residue from a donor substrate to a glucose residue. In another aspect the invention provides a nucleic acid that encodes SEQ ID NO:12.

In another embodiment the invention provides expression vectors that include the above described α-1,3/4-fucosyltranferase nucleic acids, host cells that include the expression vectors, and methods to produce the α-1,3/4-fucosyltranferase proteins using the host cells cultured under conditions suitable for expression of the α-1,3/4-fucosyltransferase protein.

In another embodiment the invention provides recombinant fucosyltransferase proteins that include amino acid sequence having greater than 90% identity to SEQ ID NO:2, 4, or 8, wherein the fucosyltransferase catalyzes the transfer of a fucose residue from a donor substrate to N-acetylglucosamine. In another embodiment the invention provides recombinant fucosyltransferase proteins that include amino acid sequence having greater than 90% identity to SEQ ID NO:6, wherein the fucosyltransferase catalyzes the transfer of a fucose residue from a donor substrate to glucose. In one aspect, the fucosyltransferase proteins comprise SEQ ID NO:2, 4, 6, or 8. In another aspect the fucosyltranferase proteins also include an amino acid tag.

In another embodiment the invention provides recombinant fucosyltransferase proteins that include SEQ ID NO:12, and that catalyzes the transfer of a fucose residue from a donor substrate to glucose. In another aspect the fucosyltranferase proteins also include an amino acid tag.

The present invention provides additional α-1,3/4-fucosyltranferase proteins and nucleic acids from *H. pylori* that catalyze the transfer of a fucose residue from a donor substrate to an acceptor substrate. In one embodiment, the invention provides α-1,3/4-fucosyltranferase nucleic acids with greater than 90% identity to a nucleotide sequence selected from SEQ ID NO:15 or 17 and that encode α-1,3/4-fucosyltranferase proteins that transfer fucose to acceptor substrates.

In another embodiment the α-1,3/4-fucosyltranferase nucleic acid is selected from SEQ ID NO:15 or 17. The invention also provides nucleic acid sequences that encode α-1,3/4-fucosyltranferase proteins, including SEQ ID NO:14 or 16 and that catalyze the transfer of fucose to an acceptor substrate, e.g., an N-acetylglucosamine residue or to a glucose residue. In one aspect the encoded α-1,3/4-fucosyltransferase also includes an amino acid tag.

In a further aspect the invention provides an isolated nucleic acid comprising a nucleic acid sequence with greater than 90% identity to SEQ ID NO:19, and that encodes an α-1,3/4-fucosyltransferase protein that catalyzes the transfer of a fucose residue from a donor substrate to an acceptor substrate. The invention also provides an isolated nucleic acid comprising a nucleic acid sequence that is SEQ ID NO:19. In another aspect the invention provides a nucleic acid that encodes SEQ ID NO:20.

In another embodiment the invention provides expression vectors that include the above described α-1,3/4-fucosyltranferase nucleic acids, host cells that include the expression vectors, and methods to produce the α-1,3/4-fucosyltranferase proteins using the host cells cultured under conditions suitable for expression of the α-1,3/4-fucosyltransferase protein.

In another embodiment the invention provides recombinant fucosyltransferase proteins that include amino acid sequence having greater than 90% identity to SEQ ID NO:16, or 18, wherein the fucosyltransferase catalyzes the transfer of a fucose residue from a donor substrate to an acceptor substrate, e.g., an N-acetylglucosamine residue or a glucose residue. In another embodiment the invention provides recombinant fucosyltransferase proteins that include amino acid sequence having greater than 93% identity to SEQ ID NO:20, wherein the fucosyltransferase catalyzes the transfer of a fucose residue from a donor substrate to an acceptor substrate, e.g., an N-acetylglucosamine residue or a glucose residue. In one aspect, the fucosyltransferase proteins comprise SEQ ID NO:16, 18, or 20. In another aspect the fucosyltranferase proteins also include an amino acid tag.

The present invention also provides methods to use the above α-1,3/4-fucosyltransferase protein, e.g., SEQ ID NOS:2, 4, 6, 12, 16, 18, or 20, to produce fucosylated oligosaccharides. The fucosylated oligosaccharides can be further purified. The acceptor substrate can be either N-acetylglucosamine or glucose depending on the needs of the user. In one embodiment the acceptor substrate is Lacto-N-neo-Tetraose (LNnT) and the fucosyltated product is Lacto-N-Fucopentaose III (LNFP III). The α-1,3/4-fucosyltransferase can be used in combination with other glycosyltransferases to produce a fucosylated oligosaccharide. For example, using lactose as a starting material, LNFP can by produced through the action of an α-1,3/4-fucosyltransferase that transfers fucose to N-acetylglucosamine, a β-1,3-N-acetylglucosaminyltransferase, and a β-1,4-galactosyltransferase. The β-1,3-N-acetylglucosaminyltransferase and the β-1,4-galactosyltransferase can be bacterial enzymes and in a preferred embodiment are from *Neisseria gonococcus*.

In another embodiment, the α-1,3/4-fucosyltransferase protein of the present invention, e.g., SEQ ID NOS:2, 4, 6, 12, 16, 18, or 20, are used to produce fucosylated glycolipids. The acceptor substrate can be either N-acetylglucosamine or glucose depending on the needs of the user.

In another embodiment, the present invention provides a method for producing a fucosylated glycoprotein, by combining an α-1,3/4-fucosyltransferase described herein, e.g., SEQ ID NOS:2, 4, 6, 12, 16, 18, or 20, with a glycoprotein that includes an appropriate acceptor substrate under conditions suitable to produce a fucosylated glycoprotein. The acceptor substrate can be selected from Galβ1-OR, Galβ,3/4GlcNAc-OR, NeuAcα2,3Galβ1,3/4GlcNAc-Or, wherein R is an amino acid, a saccharide, an oligosaccharide, or an aglycon group having at least one carbon atom. The accepter substrate can be an N-acetylglucosamine residue or a glucose residue. The α-1,3/4-fucosyltransferase can also include an amino acid tag.

BRIEF DESCRIPTION OF THE DRAWINGS

FIG. 1 provides the nucleic acid (SEQ ID NO:1) and amino acid (SEQ ID NO:2) sequences of fucosyltransferase from *H. pylori* strain 1182B.

FIG. 2 provides the nucleic acid (SEQ ID NO:3) and amino acid (SEQ ID NO:4) sequences of fucosyltransferase from *H. pylori* strain 1111A.

FIG. 3 provides the nucleic acid (SEQ ID NO:5) and amino acid (SEQ ID NO:6) sequences of fucosyltransferase from *H. pylori* strain 1218B.

FIG. 4 provides the nucleic acid (SEQ ID NO:7) and amino acid (SEQ ID NO:8) sequences of fucosyltransferase from *H. pylori* strain 19C2B.

FIG. 5 provides the nucleic acid (SEQ ID NO:9) and amino acid (SEQ ID NO:10) sequences of fucosyltransferase from *H. pylori* strain 915A.

FIG. 6 provides the nucleic acid (SEQ ID NO:11) and amino acid (SEQ ID NO:12) sequences of fucosyltransferase from *H. pylori* strain 26695A.

FIG. 7 provides the nucleic acid (SEQ ID NO:13) and amino acid (SEQ ID NO:14) sequences of fucosyltransferase from *H. pylori* strain 19C2A.

FIG. 8 provides an alignment between 1182 futB amino acid sequence (SEQ ID NO:64) and a consensus sequence from the glycosyltransferase family 10 (SEQ ID NO:65), i.e., the fucosyltransferase family. Amino acids 23 through 305 of 1182 futB are shown in the top line and represent the most conserved region of the protein, i.e. the fucosyltransferase catalytic domain.

FIG. 9 provides an alignment between 1111 futA amino acid sequence (SEQ ID NO:66) and a consensus sequence from the glycosyltransferase family 10 (SEQ ID NO:67), i.e., the fucosyltransferase family. Amino acids 27 through 417 of 1111 futA are shown in the top line and represent the most conserved region of the protein, i.e. the fucosyltransferase catalytic domain.

FIG. 10 provides an alignment between 1218 futB amino acid sequence (SEQ ID NO:68) and a consensus sequence from the glycosyltransferase family 10 (SEQ ID NO:69), i.e., the fucosyltransferase family. Amino acids 23 through 399 of 1218 futB are shown in the top line and represent the most conserved region of the protein, i.e. the fucosyltransferase catalytic domain.

FIG. 11 provides an alignment between 19C2 futB amino acid sequence (SEQ ID NO:70) and a consensus sequence from the glycosyltransferase family 10 (SEQ ID NO:71), i.e., the fucosyltransferase family. Amino acids 23 through 377 of 19C2 futB are shown in the top line and represent the most conserved region of the disclosed protein, i.e. the fucosyltransferase catalytic domain.

FIG. 12 provides an alignment between amino acid sequence of *H. pylori* strains 1182 FutB (SEQ ID NO:74), 1111 FutA (SEQ ID NO:72), 1218 FutB (SEQ ID NO:75), 19C2 FutB (SEQ ID NO:76), 915FutA (SEQ ID NO:10), 19C2 FutA (SEQ ID NO:14), and 26695 FutA (SEQ ID NO:73). The bottom sequence is a consensus sequence (SEQ ID NO:77).

FIG. 13 provides an alignment between nucleic acid sequence of *H. pylori* strains 1182 FutB (SEQ ID NO:1), 1111 FutA (SEQ ID NO:3), 1218 FutB (SEQ ID NO:5), 19C2 FutB (SEQ ID NO:7), 915FutA (SEQ ID NO:78), 19C2 FutA (SEQ ID NO:13), and 26695 FutA (SEQ ID NO:11). The bottom sequence is a consensus sequence (SEQ ID NO:79)

FIG. 14 provides oligosaccharide structures of Lacto-N-neo-Tetraose (LNnT), a substrate of the *H. pylori* fucosyltransferases and Lacto-N-Fucopentaose III (LNFPIII or LNFIII), a product of the *H. pylori* fucosyltransferases.

FIG. 15 provides the results of analysis of acceptor specificity for the *H. pylori* fucosyltransferases.

FIG. 16 provides the yield of LNFIII synthesis using the *H. pylori* fucosyltransferases. Two ion exchange resins were tested: MR3 $NH_4HCO_3$ and Dowex1/Dowex50 resin.

FIG. 17 demonstrates the use of FutB α-1,3/4-fucosyltranferase from *H. pylori* strain 1182 to transfer fucose to the glycoprotein asialyltranferrin. The upper panel shows GC/MS analysis of sialylated transferrin. The lower panel shows GC/MS analysis of sialylated transferrin that has been enzymatically asialylated and then fucosylated using *H. pylori* strain 1182 FutB α-1,3/4-fucosyltranferase. Key to sugar structures: filled squares-GlcNAc; open circles-mannose; filled diamonds-galactose; triangles-fucose; stars-sialic acid.

FIG. 18 provides the nucleic acid sequence (top; SEQ ID NO:15) and amino acid sequence (bottom; SEQ ID NO:16) of *H. pylori* strain 1111FutB fucosyltransferase. The nucleic acid sequence begins with a BamHI site in lower case letters. The coding sequence is also in lower case letters (i.e., atg . . . taa), and the sequence ends with an EcoRI site in lower case letters.

FIG. 19 provides the nucleic acid sequence (top; SEQ ID NO:17) and amino acid sequence (bottom; SEQ ID NO:18) of *H. pylori* strain 802FutA fucosyltransferase. The nucleic acid sequence begins with a BamHI site in lower case letters. The coding sequence begins with an atg in lower case letters, and ends with a stop codon (taa) in lower case letters, and the sequence ends with an EcoRI site in lower case letters.

FIG. 20 provides the nucleic acid sequence (top; SEQ ID NO:19) and amino acid sequence (bottom; SEQ ID NO:20) of *H. pylori* strain 948FutA fucosyltransferase. The nucleic acid sequence begins with a BamHI site in lower case letters. The coding sequence is also in lower case letters (i.e., atg . . . taa), and the sequence ends with an EcoRI site in lower case letters.

FIG. 21 provides the nucleic acid sequence (top; SEQ ID NO:21) and amino acid sequences (bottom; SEQ ID NOS: 22-46) of *H. pylori* strain 955FutA fucosyltransferase. The nucleic acid sequence begins with a BamHI site in lower case letters. The start codon (i.e., atg) is in lower case letters, and the sequence ends with an EcoRI site in lower case letters.

FIG. 22 provides the nucleic acid sequence (top; SEQ ID NO:47) and amino acid sequences (bottom; SEQ ID NOS: 48-61) of *H. pylori* strain 1218FutA fucosyltransferase. The nucleic acid sequence begins with a BamHI site in lower case letters, and the sequence ends with an EcoRI site in lower case letters.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

The terms "α-1,3/4-fucosyltranferase or fucosyltransferase" or a nucleic acid encoding an "α-1,3/4-fucosyltranferase or fucosyltransferase" refer to nucleic acid and polypeptide polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to a polypeptide encoded by a nucleic acid selected from SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19; or an amino acid sequence of SEQ ID NO:2; SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20; (2) specifically bind to antibodies, e.g., polyclonal antibodies, raised against an immunogen comprising an amino acid sequence of SEQ ID NO:2; SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20; immunogenic fragments thereof, and conservatively modified variants thereof; (3) specifically hybridize under stringent hybridization conditions to a nucleic acid encoding SEQ ID NO:2; SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20; e.g., a nucleic acid sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19; or its complement, and conservatively modified variants thereof; (4) have a nucleic acid sequence that has greater than about 90%, preferably greater than about 91%, 92%, 93%, 94%, 95%, 96%, 97%, 98%, 99%, or higher nucleotide sequence identity, preferably over a region of at least about 25, 50, 100, 200, 500, 1000, or more nucleotides, to SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19; or its complement. The nucleic acids and proteins of the invention include both naturally occurring or recombinant molecules.

The α-1,3/4-fucosyltranferase enzymes of the invention can also be recognized by the presence of highly conserved catalytic domains that are found in a family of fucosyltransferase proteins, glycosyltransferase family 10, see e.g., gnl|CDD|16836 pfam00852, Glyco_transf_10. Alignments between conserved catalytic domains of 1182 futB, 1111 futA, 1218 futB, and 19C2 futB and a consensus sequence from the catalytic domain of glycosyltransferase family 10 members are shown in FIGS. 8-11. Those of skill will recognize that similar alignments can be made to determine conserved catalytic domains in e.g., SEQ ID NO:16, SEQ ID NO:18, or SEQ ID NO:20.

A biologically active fucosyltransferase as described herein is a fucosyltransferase that catalyzes the transfer of fucose from a donor substrate, for example, GDP-fucose, to an acceptor molecule in an α-1,3/4-linkage. The acceptor molecule can be either N-acetylglucosylamine (GlucNAc) or glucose. For example, Fucosyltransferases from the following *H. pylori* strains transfer fucose to Glc-NAc: Strain 915 FutA, Strain 1111 FutA, Strain 19C2 FutB, and Strain 1182 FutB. The FutA gene product from *H. pylori* Strain 19C2 FutA transfers fucose to the reducing glucose of the LNnT acceptor, as did the FutB gene product from *H. pylori* strain 1218, and a novel 26695 FutA protein. In preferred embodiments, the fucosyltransferase transfers fuscose exclusively to GlcNAc or exclusively to glucose. The acceptor molecule can be a carbohydrate, an oligosaccharide, a glycolipid, or a glycoprotein.

The *H. pylori* fucosyltransferase proteins of the invention are useful for transferring a saccharide from a donor substrate to an acceptor substrate. The addition generally takes place at the non-reducing end of an oligosaccharide or carbohydrate moiety on a biomolecule. However, in some embodiments the fucose residue is added to a reducing glucose residue. Biomolecules as defined here include but are not limited to biologically significant molecules such as carbohydrates, oligosaccchrides, proteins (e.g., glycoproteins), and lipids (e.g., glycolipids, phospholipids, sphingolipids and gangliosides).

The following abbreviations are used herein:
Ara=arabinosyl;
Fru=fructosyl;
Fuc=fucosyl;
Gal=galactosyl;
GalNAc=N-acetylgalactosylamino;
Glc=glucosyl;
GlcNAc=N-acetylglucosylamino;
Man=mannosyl; and
NeuAc=sialyl (N-acetylneuraminyl)

FT or Fut=fucosyltransferase*
ST=sialyltransferase*
GalT=galactosyltransferase*

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

All oligosaccharides described herein are described with the name or abbreviation for the non-reducing saccharide (e.g., Gal), followed by the configuration of the glycosidic bond (α or β), the ring bond, the ring position of the reducing saccharide involved in the bond, and then the name or abbreviation of the reducing saccharide (e.g., GlcNAc). The linkage between two sugars may be expressed, for example, as 2,3, 2→3, or (2,3). Each saccharide is a pyranose or furanose.

The term "sialic acid" refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O—$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); *Sialic Acids: Chemistry, Metabolism and Function*, R. Schauer, Ed. (Springer-Verlag, New York (1992)). The synthesis and use of sialic acid compounds in a sialylation procedure is disclosed in international application WO 92/16640, published Oct. 1, 1992.

An "acceptor substrate" for a glycosyltransferase is an oligosaccharide moiety that can act as an acceptor for a particular glycosyltransferase. When the acceptor substrate is contacted with the corresponding glycosyltransferase and sugar donor substrate, and other necessary reaction mixture components, and the reaction mixture is incubated for a sufficient period of time, the glycosyltransferase transfers sugar residues from the sugar donor substrate to the acceptor substrate. The acceptor substrate will often vary for different types of a particular glycosyltransferase.

An "acceptor substrate" for an *H. pylori* fucosyltransferase is an oligosaccharide moiety that can act as an acceptor for a the *H. pylori* fucosyltransferase. When the acceptor substrate is contacted with the *H. pylori* fucosyltransferase and sugar donor substrate (e.g., GDP-fucose), and other necessary reaction mixture components, and the reaction mixture is incubated for a sufficient period of time, the *H. pylori* fucosyltransferase transfers fucose residues from the GDP-fucose to the acceptor substrate. The acceptor substrate will often vary for different types of a particular fucosyltransferases. For example, the acceptor substrate for a mammalian galactoside 2-L-fucosyltransferase (α1,2-fucosyltransferase) will include a Galβ1,4-GlcNAc-R at a non-reducing terminus of an oligosaccharide; this fucosyltransferase attaches a fucose residue to the Gal via an α1,2 linkage. Terminal Galβ1,4-GlcNAc-R and Galβ1,3-GlcNAc-R and sialylated analogs thereof are acceptor substrates for α1,3 and α1,4-fucosyltransferases, respectively.

These enzymes, however, attach the fucose residue to the GlcNAc residue of the acceptor substrate. Accordingly, the term "acceptor substrate" is taken in context with the particular glycosyltransferase of interest for a particular application. The *H. pylori* fucosyltransferase described herein will transfer fucose to sialylated or unsialylated acceptor substrates. Some *H. pylori* fucosyltransferase described herein will transfer fucose to glucose residues.

A "donor substrate" for glycosyltransferases is an activated nucleotide sugar. Such activated sugars generally consist of uridine, guanosine, and cytidine monophosphate derivatives of the sugars (UMP, GMP and CMP, respectively) or diphosphate derivatives of the sugars (UDP, GDP and CDP, respectively) in which the nucleoside monophosphate or diphosphate serves as a leaving group. For example, a donor substrate for fucosyltransferases is GDP-fucose. Donor substrates for sialyltransferases, for example, are activated sugar nucleotides comprising the desired sialic acid. For instance, in the case of NeuAc, the activated sugar is CMP-NeuAc.

A "substantially uniform glycoform" or a "substantially uniform glycosylation pattern," when referring to a glycoprotein species, refers to the percentage of acceptor substrates that are glycosylated by the glycosyltransferase of interest (e.g., fucosyltransferase). For example, in the case of the α1,3 or α1,4 fucosyltransferase noted above, a substantially uniform fucosylation pattern exists if substantially all (as defined below) of the Galβ1,4-GlcNAc-R and sialylated or unsialylated analogues thereof are fucosylated in a composition comprising the glycoprotein of interest. It will be understood by one of skill in the art, that the starting material may contain glycosylated acceptor substrates (e.g., fucosylated Galβ1,4-GlcNAc-R substrates). Thus, the calculated amount of glycosylation will include acceptor substrates that are glycosylated by the methods of the invention, as well as those acceptor substrates already glycosylated in the starting material.

The term "substantially" in the above definitions of "substantially uniform" generally means at least about 60%, at least about 70%, at least about 80%, or more preferably at least about 90%, 91%, 92%, 93%, 94%, 95%, 96%, 97%, 98%, 99%, or 100% of the acceptor substrates for a particular glycosyltransferase are glycosylated (e.g., fucosylated Galβ1,4-GlcNAc-R substrates).

The term "substantially identical fucosylation pattern," refers to a glycosylation pattern of a glycoprotein produced by a method of the invention which is at least about 80%, more preferably at least about 90%, even more preferably at least about 91%, 92%, 93%, 94%, or 95% and still more preferably at least about 96%, 97%, 98% or 99% identical to the fucosylation of a known glycoprotein. "Known fucosylation pattern," refers to a fucosylation pattern of a known glycoprotein from any source having any known level of fucosylation.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Protein", "polypeptide", or "peptide" refer to a polymer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, β-alanine, phenylglycine and homoarginine are also included. Amino acids that are not gene-encoded may also be used in the present invention. Furthermore, amino acids that have been modified to include reactive groups may also be used in the invention. All of the amino acids used in the present invention may be either the D- or L-isomer. The L-isomers are generally preferred. In addition, other peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques. A "recombinant protein" is one which has been produced by a recombinant cell.

A "fusion protein" refers to an *H. pylori* fucosyltransferase protein comprising amino acid sequences that are in addition to, in place of, less than, and/or different from the amino acid sequences encoding the original or native full-length protein or subsequences thereof.

Components of fusion proteins include "accessory enzymes" and/or "purification or amino acid tags." An "accessory enzyme" as referred to herein, is an enzyme that is involved in catalyzing a reaction that, for example, forms a substrate for a fucosyltransferase. An accessory enzyme can, for example, catalyze the formation of a nucleotide sugar that is used as a donor moiety by a fucosyltransferase, e.g., GDP-fucose. An accessory enzyme can also be one that is used in the generation of a nucleotide triphosphate required for formation of a nucleotide sugar, or in the generation of the sugar which is incorporated into the nucleotide sugar, e.g., fucose. The recombinant fusion protein of the invention can be constructed and expressed as a fusion protein with a molecular "purification tag" at one end, which facilitates purification of the protein. Such tags can also be used for immobilization of a protein of interest during the glycosylation reaction. Suitable tags include "epitope tags," which are a protein sequence that is specifically recognized by an antibody. Epitope tags are generally incorporated into fusion proteins to enable the use of a readily available antibody to unambiguously detect or isolate the fusion protein. A "FLAG tag" is a commonly used epitope tag, specifically recognized by a monoclonal anti-FLAG antibody, consisting of the sequence Asp-TyrLysAspAspAspAspLys (SEQ ID NO:80) or a substantially identical variant thereof. Other suitable tags are known to those of skill in the art, and include, for example, an affinity tag such as a hexahistidine (SEQ ID NO:81) peptide, which will bind to metal ions such as nickel or cobalt ions. Purification tags also include maltose binding domains and starch binding domains. Purification of maltose binding domain proteins is know to those of skill in the art. Starch binding domains are described in WO 99/15636, herein incorporated by reference. Affinity purification of a fusion protein comprising a starch binding domain using a betacyclodextrin (BCD)-derivatized resin is described in U.S. Ser. No. 60/468,374, filed May 5, 2003, herein incorporated by reference in its entirety.

The term "functional domain" with reference to glycosyltransferases, refers to a domain of the glycosyltransferase that confers or modulates an activity of the enzyme, e.g., acceptor substrate specificity, catalytic activity, binding affinity, or other biological or biochemical activity. Examples of functional domains of glycosyltransferases include, but are not limited to, the catalytic domain.

The terms "expression level" or "level of expression" with reference to a protein refers to the amount of a protein produced by a cell. The amount of protein produced by a cell can be measured by the assays and activity units described herein or known to one skilled in the art. One skilled in the art would know how to measure and describe the amount of protein produced by a cell using a variety of assays and units, respectively. Thus, the quantitation and quantitative description of the level of expression of a protein, e.g., an H. pylori fucosyltransferase, can be assayed measuring the enzymatic activity or the units used to describe the activity, or the amount of protein. The amount of protein produced by a cell can be determined by standard known assays, for example, the protein assay by Bradford (1976), the bicinchoninic acid protein assay kit from Pierce (Rockford, Ill.), or as described in U.S. Pat. No. 5,641,668.

The term "enzymatic activity" refers to an activity of an enzyme and may be measured by the assays and units described herein or known to one skilled in the art.

The term "specific activity" as used herein refers to the catalytic activity of an enzyme, e.g., an H. pylori fucosyltransferase protein of the present invention, and may be expressed in activity units. As used herein, one activity unit catalyzes the formation of 1 μmol of product per minute at a given temperature (e.g., at 37° C.) and pH value (e.g., at pH 7.5). Thus, 10 units of an enzyme is a catalytic amount of that enzyme where 10 μmol of substrate are converted to 10 μmol of product in one minute at a temperature of, e.g., 37° C. and a pH value of, e.g., 7.5.

A "catalytic domain" refers to a protein domain, or a subsequence thereof, that catalyzes an enzymatic reaction performed by the enzyme. For example, a catalytic domain of a fucosyltransferase will include a subsequence of the fucosyltransferase sufficient to transfer a fucose residue from a donor to an acceptor saccharide. A catalytic domain can include an entire enzyme, a subsequence thereof, or can include additional amino acid sequences that are not attached to the enzyme, or a subsequence thereof, as found in nature. The α-1,3/4-fucosyltranferase enzymes of the invention can also be recognized by the presence of highly conserved catalytic domains that are found in a family of fucosyltransferase proteins, glycosyltransferase family 10, see e.g., gnl|CDD|16836 pfam00852, Glyco_transf_10. Alignments between conserved catalytic domains of 1182 futB, 1111 futA, 1218 futB, and 19C2 futB and a consensus sequence from the catalytic domain of glycosyltransferase family 10 members are shown in FIGS. 8-11. Alignments between conserved catalytic domains of 1182 futB, 1111 futA, 1218 futB, and 19C2 futB and a consensus sequence from the catalytic domain of glycosyltransferase family 10 members are shown in FIGS. 8-11. Those of skill will recognize that similar alignments can be made to determine conserved catalytic domains in e.g., SEQ ID NO:16, SEQ ID NO:18, or SEQ ID NO:20. Highly conserved regions, similar to a region of the glycosyltransferase family 10 catalytic domain consensus sequence starting at about amino acid 11 and ending at amino acid 301, are found in each of the H. pylori α-1,3/4-fucosyltranferase enzymes listed above, e.g., 1182 futB, amino acids 23-305; 1111 futA, amino acids 27-304; 1218 futB, amino acids 23-305; and 19C2 futB amino acids 22-277, and are believed to be the catalytic domains of the enzyme. Thus, polypeptides comprising the above-identified fucosyltransferase catalytic domains can be used in the methods of the invention, e.g., fucosylating glycoproteins. Nucleic acids that encode the above-identified fucosyltransferase catalytic domains can also be used in the methods of the invention, e.g., production of fucosyltransferase proteins for fucosylating glycoproteins.

A "subsequence" refers to a sequence of nucleic acids or amino acids that comprise a part of a longer sequence of nucleic acids or amino acids (e.g., protein) respectively.

The term "nucleic acid" refers to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

A "heterologous sequence" or a "heterologous nucleic acid", as used herein, is one that originates from a source foreign to the particular host cell, or, if from the same source, is modified from its original form. Thus, a heterologous glycoprotein gene in a eukaryotic host cell includes a glycoprotein-encoding gene that is endogenous to the particular host cell that has been modified. Modification of the heterologous sequence may occur, e.g., by treating the DNA with a restriction enzyme to generate a DNA fragment that is capable of being operably linked to the promoter. Techniques such as site-directed mutagenesis are also useful for modifying a heterologous sequence.

The term "isolated" refers to material that is substantially or essentially free from components which interfere with the activity of an enzyme. For a saccharide, protein, or nucleic acid of the invention, the term "isolated" refers to material that is substantially or essentially free from components which normally accompany the material as found in its native state. Typically, an isolated saccharide, protein, or nucleic acid of the invention is at least about 80% pure, usually at least about 90%, and preferably at least about 95% pure as measured by band intensity on a silver stained gel or other method for determining purity. Purity or homogeneity can be indicated by a number of means well known in the art. For example, a protein or nucleic acid in a sample can be resolved by polyacrylamide gel electrophoresis, and then the protein or nucleic acid can be visualized by staining. For certain purposes high resolution of the protein or nucleic acid may be desirable and HPLC or a similar means for purification, for example, may be utilized.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The terms "identical" or percent "identity," in the context of two or more nucleic acids or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or proteins, refers to two or more sequences or subsequences that have greater than about 60% nucleic acid or amino acid sequence identity, 65%, 70%, 75%, 80%, 85%, 90%, preferably 91%, 92%, 93%, 94%, 95%, 96%, 97%, 98% or 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschuel et al. (1977) Nucleic Acids Res. 25: 3389-3402, respectively. Software for performing BLAST analyses is publicly available through the National Center for Biotechnology Information (on the World Wide Web at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89: 10915 (1989)). BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or proteins are substantially identical is that the protein encoded by the first nucleic acid is immunologically cross reactive with the protein encoded by the second nucleic acid, as described below. Thus, a protein is typically substantially identical to a second protein, for example, where the two peptides differ only by conservative substitutions. Another indication that two nucleic acid sequences are substantially identical is that the two molecules hybridize to each other under stringent conditions, as described below.

The phrase "hybridizing specifically to" refers to the binding, duplexing, or hybridizing of a molecule only to a particular nucleotide sequence under stringent conditions when that sequence is present in a complex mixture (e.g., total cellular) DNA or RNA.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 15° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is typically at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32-48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90-95° C. for 30-120 sec, an annealing phase lasting 30-120 sec, and an extension phase of about 72° C. for 1-2 min. Protocols and guidelines for low and high stringency amplification reactions are available, e.g., in Innis, et al. (1990) *PCR Protocols: A Guide to Methods and Applications* Academic Press, N.Y.

The phrases "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given protein. For instance, the codons CGU, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations," which are one species of "conservatively modified variations." Every polynucleotide sequence described herein which encodes a protein also describes every possible silent variation, except where otherwise noted. One of skill will recognize that each codon in a nucleic acid (except AUG, which is ordinarily the only codon for methionine, and UGG which is ordinarily the only codon for tryptophan) can be modified to yield a functionally identical molecule by standard techniques. Accordingly, each "silent variation" of a nucleic acid which encodes a protein is implicit in each described sequence.

Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art.

One of skill will appreciate that many conservative variations of the fusion proteins and nucleic acid which encode the fusion proteins yield essentially identical products. For example, due to the degeneracy of the genetic code, "silent substitutions" (i.e., substitutions of a nucleic acid sequence which do not result in an alteration in an encoded protein) are an implied feature of every nucleic acid sequence which encodes an amino acid. As described herein, sequences are preferably optimized for expression in a particular host cell used to produce the chimeric glycosyltransferases (e.g., yeast, human, and the like). Similarly, "conservative amino acid substitutions," in one or a few amino acids in an amino acid sequence are substituted with different amino acids with highly similar properties (see, the definitions section, supra), are also readily identified as being highly similar to a particular amino acid sequence, or to a particular nucleic acid sequence which encodes an amino acid. Such conservatively substituted variations of any particular sequence are a feature of the present invention. See also, Creighton (1984) *Proteins*, W.H. Freeman and Company. In addition, individual substitutions, deletions or additions which alter, add or delete a single amino acid or a small percentage of amino acids in an encoded sequence are also "conservatively modified variations".

The practice of this invention can involve the construction of recombinant nucleic acids and the expression of genes in transfected host cells. Molecular cloning techniques to achieve these ends are known in the art. A wide variety of cloning and in vitro amplification methods suitable for the construction of recombinant nucleic acids such as expression vectors are well known to persons of skill. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); and *Current Protocols in Molecular Biology*, F. M. Ausubel et al., eds., Current Protocols, a joint venture between Greene Publishing Associates, Inc. and John Wiley & Sons, Inc., (1999 Supplement) (Ausubel). Suitable host cells for expression of the recombinant *H. pylori* fucosyltransferases are known to those of skill in the art, and include, for example, bacterial cells, including *E. coli*. Eucaryotic cells can also be used in the present invention, for example insect cells such as Sf9 cell and yeast or fungal cells (e.g., *Aspergillus niger* or yeast).

Examples of protocols sufficient to direct persons of skill through in vitro amplification methods, including the polymerase chain reaction (PCR) the ligase chain reaction (LCR), Qβ-replicase amplification and other RNA polymerase mediated techniques are found in Berger, Sambrook, and Ausubel, as well as Mullis et al. (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87: 1874; Lomell et al. (1989) *J. Clin. Chem.* 35: 1826; Landegren et al. (1988) *Science* 241: 1077-1080; Van Brunt (1990) *Biotechnology* 8: 291-294; Wu and Wallace (1989) *Gene* 4: 560; and Barringer et al. (1990) *Gene* 89: 117. Improved methods of cloning in vitro amplified nucleic acids are described in Wallace et al., U.S. Pat. No. 5,426,039.

DETAILED DESCRIPTION OF THE INVENTION

The present invention provides for the first time bacterial α-1,3/4-fucosyltranferases, i.e., *H. pylori* fucosyltransferases, that transfer fucose from a donor substrate to an acceptor sugar on a glycoprotein. In addition, the fucosyltransferases are useful for producing fucosylated oligosaccharides and glycolipids.

Specifically, α-1,3/4-fucosyltransferases from the following *H. pylori* strains were cloned and analyzed: 915A2, 1111A2, 19C2B1, 1182B3, 19C2A5, 26695, and 1218. Fucosyltransferases from the following *H. pylori* strains transferred fucose to Glc-NAc: 915A2, 1111A2, 19C2FutB, and 1182B3. The FutA gene product from *H. pylori* strain 19C2A5 transferred fucose to the reducing glucose of the LNnT acceptor, as did the FutB gene product from *H. pylori* strain 1218. The ability of FutA gene product from *H. pylori* strain 26695 to transfer fucose to glucose was confirmed.

A major advantage of the *H. pylori* α-1,3/4-fucosyltranferases over mammalian α-1,3/4-fucosyltransferases is that the *H. pylori* enzyme appears to be unaffected by the sialylation status of the acceptor. In addition some of the *H. pylori* fucosyltransferases add fucose exclusively to the N-acetylglucosamine (glcNAc) residue in acceptor sugars that contain both glucose and glcNAc residues. In contrast, mammalian an α-1,3/4-fucosyltransferases are sensitive to the degree of sialylation of the acceptor and some mammalian enzymes add to both glucose and glcNAc residues in the same acceptor. In addition bacterially expressed enzymes offer a large cost savings relative to the expression of mammalian gene products in Sf9 or CHO systems.

A. Cloning of *H. pylori* α-1,3/4-Fucosyltranferases Proteins

Nucleic acids that encode glycosyltransferases, e.g., *H. pylori* α-1,3/4-fucosyltranferases and methods of obtaining such nucleic acids, are known to those of skill in the art. Suitable nucleic acids (e.g., cDNA, genomic, or subsequences (probes)) can be cloned, or amplified by in vitro methods such as the polymerase chain reaction (PCR), the ligase chain reaction (LCR), the transcription-based amplification system (TAS), or the self-sustained sequence replication system (SSR). A wide variety of cloning and in vitro amplification methodologies are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, NY, (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864.

A DNA that encodes an *H. pylori* α-1,3/4-fucosyltranferase, or a subsequences thereof, can be prepared by any suitable method described above, including, for example, cloning and restriction of appropriate sequences with restriction enzymes. In one preferred embodiment, nucleic acids encoding *H. pylori* α-1,3/4-fucosyltranferases are isolated by routine cloning methods. A nucleotide sequence of a *H. pylori* α-1,3/4-fucosyltranferase as provided in, for example, GenBank or other sequence database (see above) can be used to provide probes that specifically hybridize to a *H. pylori* α-1,3/4-fucosyltranferases gene in a genomic DNA sample, or to an mRNA, encoding an *H. pylori* α-1,3/4-fucosyltranferase, in a total RNA sample (e.g., in a Southern or Northern blot). Once the target nucleic acid encoding a *H. pylori* α-1,3/4-fucosyltranferase is identified, it can be isolated according to standard methods known to those of skill in the art (see, e.g., Sambrook et al. (1989) *Molecular Cloning: A Laboratory Manual,* 2nd Ed., Vols. 1-3, Cold Spring Harbor Laboratory; Berger and Kimmel (1987) *Methods in Enzymology, Vol.* 152: *Guide to Molecular Cloning Techniques*, San Diego: Academic Press, Inc.; or Ausubel et al. (1987) *Current Protocols in Molecular Biology*, Greene Publishing and Wiley-Interscience, New York). Further, the isolated nucleic acids can be cleaved with restriction enzymes to create nucleic acids encoding the full-length *H. pylori* α-1,3/4-fucosyltranferase, or subsequences thereof, e.g., containing subsequences encoding at least a subsequence of a catalytic domain of a *H. pylori* α-1,3/4-fucosyltranferase. These restriction enzyme fragments, encoding an *H. pylori* α-1,3/4-fucosyltranferase or subsequences thereof, may then be ligated, for example, to produce a nucleic acid encoding an *H. pylori* α-1,3/4-fucosyltranferase protein.

A nucleic acid encoding an *H. pylori* α-1,3/4-fucosyltranferase, or a subsequence thereof, can be characterized by assaying for the expressed product. Assays based on the detection of the physical, chemical, or immunological properties of the expressed protein can be used. For example, one can identify a cloned *H. pylori* α-1,3/4-fucosyltranferases, by the ability of a protein encoded by the nucleic acid to catalyze the transfer of a fucose residue from a donor substrate to an acceptor substrate. In one method, capillary electrophoresis is employed to detect the reaction products. This highly sensitive assay involves using either saccharide or disaccharide aminophenyl derivatives which are labeled with fluorescein as described in Wakarchuk et al. (1996) *J. Biol. Chem.* 271 (45): 28271-276. For example, to assay for a *Neisseria* lgtC enzyme, either FCHASE-AP-Lac or FCHASE-AP-Gal can be used, whereas for the *Neisseria* lgtB enzyme an appropriate reagent is FCHASE-AP-GlcNAc (Id.). Other methods for detection of a fucosylated reation product include thin layer chromatography and GC/MS.

Also, a nucleic acid encoding an *H. pylori* α-1,3/4-fucosyltranferase, or a subsequence thereof, can be chemically synthesized. Suitable methods include the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.*, 22: 1859-1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill recognizes that while chemical synthesis of DNA is often limited to sequences of about 100 bases, longer sequences may be obtained by the ligation of shorter sequences.

Nucleic acids encoding *H. pylori* α-1,3/4-fucosyltranferases, or subsequences thereof, can be cloned using DNA amplification methods such as polymerase chain reaction (PCR). Thus, for example, the nucleic acid sequence or subsequence is PCR amplified, using a sense primer containing one restriction enzyme site (e.g., NdeI) and an antisense primer containing another restriction enzyme site (e.g., HindIII). This will produce a nucleic acid encoding the desired *H. pylori* α-1,3/4-fucosyltranferases or subsequence and having terminal restriction enzyme sites. This nucleic acid can then be easily ligated into a vector containing a nucleic acid encoding the second molecule and having the appropriate corresponding restriction enzyme sites. Suitable PCR primers can be determined by one of skill in the art using the sequence information provided in GenBank or other sources. Appropriate restriction enzyme sites can also be added to the nucleic acid encoding the *H. pylori* α-1,3/4-fucosyltranferase protein or protein subsequence by site-directed mutagenesis. The plasmid containing the *H. pylori* α-1,3/4-fucosyltranferase-encoding nucleotide sequence or subsequence is cleaved with the appropriate restriction endonuclease and then ligated into an appropriate vector for amplification and/or expression according to standard methods. Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al., eds) Academic Press Inc. San Diego, Calif. (1990) (Innis); Arnheim & Levinson (Oct. 1, 1990) C&EN 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.*, 35: 1826; Landegren et al., (1988) *Science* 241: 1077-1080; Van Brunt (1990) *Biotechnology* 8: 291-294; Wu and Wallace (1989) *Gene* 4: 560; and Barringer et al. (1990) *Gene* 89: 117.

Other physical properties of a cloned *H. pylori* α-1,3/4-fucosyltranferase protein expressed from a particular nucleic acid, can be compared to properties of known *H. pylori* α-1,3/4-fucosyltranferases to provide another method of identifying suitable sequences or domains of the *H. pylori* α-1,3/4-fucosyltranferases that are determinants of acceptor substrate specificity and/or catalytic activity. Alternatively, a putative *H. pylori* α-1,3/4-fucosyltranferase gene or recombinant *H. pylori* α-1,3/4-fucosyltranferase gene can be mutated, and its role as an α-1,3/4-fucosyltranferases, or the role of particular sequences or domains established by detecting a variation in the structure of a carbohydrate normally produced by the unmutated, naturally-occurring, or control α-1,3/4-fucosyltranferases.

Functional domains of cloned *H. pylori* α-1,3/4-fucosyltranferases can be identified by using standard methods for mutating or modifying the g *H. pylori* α-1,3/4-fucosyltranferases and testing the modified or mutated proteins for activities such as acceptor substrate activity and/or catalytic activity, as described herein. The functional domains of the various *H. pylori* α-1,3/4-fucosyltranferases can be used to construct nucleic acids encoding α-1,3/4-fucosyltranferases proteins comprising the functional domains of one or more α-1,3/4-fucosyltranferases. These fusion proteins can then be tested for the desired acceptor substrate or catalytic activity.

In an exemplary approach to cloning nucleic acids encoding α-1,3/4-fucosyltranferase proteins, the known nucleic acid or amino acid sequences of cloned glycosyltransferases are aligned and compared to determine the amount of sequence identity between various glycosyltransferases. This information can be used to identify and select protein domains that confer or modulate glycosyltransferase activities, e.g., acceptor substrate activity and/or catalytic activity based on the amount of sequence identity between the glycosyltransferases of interest. For example, domains having sequence identity between the fucosyltransferases of interest, and that are associated with a known activity, can be used to construct fucosyltransferase proteins containing that domain, and having the activity associated with that domain (e.g., acceptor substrate specificity and/or catalytic activity).

B. Fusion Protein Comprising Accessory Enzymes Involved in Nucleotide Sugar Formation In some embodiments, the fusion polypeptides of the invention include, in addition to the α-1,3/4-fucosyltranferases catalytic domain(s) and/or other functional domains, at least one catalytic domain from an accessory enzyme. Accessory enzymes include, for example, those enzymes that are involved in the formation of a nucleotide sugar. The accessory enzyme can be involved in attaching the sugar to a nucleotide, or can be involved in making the sugar or the nucleotide, for example. The nucleotide sugar is generally one that is utilized as a saccharide donor by the glycosyltransferase catalytic domain of the particular fusion polypeptide. α-1,3/4-fucosyltranferases utilize GDP-fucose as a sugar donor. Examples of fusion proteins comprising a functional domain from a glycosyltransferase and an accessory enzyme and methods to make such fusions are found for example in PCT/CA98/01180, U.S. Ser. No. 09/211,691 filed Dec. 14, 1998 both of which are herein incorporated by reference for all purposes.

Accessory enzymes that are involved in synthesis of nucleotide sugars are well known to those of skill in the art. For a review of bacterial polysaccharide synthesis and gene nomenclature, see, e.g., Reeves et al., *Trends Microbiol.* 4: 495-503 (1996). The methods described above for obtaining glycosyltransferase-encoding nucleic acids are also applicable to obtaining nucleic acids that encode enzymes involved in the formation of nucleotide sugars. For example, one can use one of nucleic acids known in the art, some of which are listed below, directly or as a probe to isolate a corresponding nucleic acid from other organisms of interest.

An example of a fusion polypeptide provided by the invention is used for producing a fucosylated soluble oligosaccharide. The donor nucleotide sugar for fucosyltransferases is GDP-fucose, which is relatively expensive to produce. To reduce the cost of producing the fucosylated oligosaccharide, the invention provides fusion polypeptides that can convert the relatively inexpensive GDP-mannose into GDP-fucose, and then catalyze the transfer of the fucose to an acceptor saccharide. These fusion polypeptides include a catalytic domain from at least one of a GDP-mannose dehydratase, a GDP-4-keto-6-deoxy-D-mannose 3,5-epimerase, or a GDP-4-keto-6-deoxy-L-glucose 4-reductase. When each of these enzyme activities is provided, one can convert GDP-mannose into GDP-fucose.

The nucleotide sequence of an *E. coli* gene cluster that encodes GDP-fucose-synthesizing enzymes is described by Stevenson et al. (1996) *J. Bacteriol.* 178: 4885-4893; GenBank Accession No. U38473). This gene cluster had been reported to include an open reading frame for GDP-mannose dehydratase (nucleotides 8633-9754; Stevenson et al., supra.). It was recently discovered that this gene cluster also contains an open reading frame that encodes an enzyme that has both 3,5 epimerization and 4-reductase activities (see, commonly assigned U.S. Pat. No. 6,500,661, issued Dec. 31, 2002), and thus is capable of converting the product of the GDP-mannose dehydratase reaction (GDP-4-keto-6-deoxymannose) to GDP-fucose. This ORF, which is designated YEF B, is found between nucleotides 9757-10722. Prior to this discovery that YEF B encodes an enzyme having two activities, it was not known whether one or two enzymes were required for conversion of GDP-4-keto-6-deoxymannose to GDP-fucose. The nucleotide sequence of a gene encoding the human Fx enzyme is found in GenBank Accession No. U58766.

Also provided are fusion polypeptides that include a mannosyltransferase catalytic domain and a catalytic domain of a GDP-Man pyrophosphorylase (EC 2.7.7.22), which converts Man-1-P to GDP-Man. Suitable genes are known from many organisms, including *E. coli*: GenBank U13629, AB010294, D43637 D13231, Bastin et al., *Gene* 164: 17-23 (1995), Sugiyama et al., *J. Bacteriol.* 180: 2775-2778 (1998), Sugiyama et al., *Microbiology* 140 (Pt 1): 59-71 (1994), Kido et al., *J. Bacteriol.* 177: 2178-2187 (1995); *Klebsiella pneumoniae*: GenBank AB010296, AB010295, Sugiyama et al., *J. Bacteriol.* 180: 2775-2778 (1998); *Salmonella enterica*: GenBank X56793 M29713, Stevenson et al., *J. Bacteriol.* 178: 4885-4893 (1996).

The fusion polypeptides of the invention for fucosylating a saccharide acceptor can also utilize enzymes that provide a minor or "scavenge" pathway for GDP-fucose formation. In this pathway, free fucose is phosphorylated by fucokinase to form fucose 1-phosphate, which, along with guanosine 5'-triphosphate (GTP), is used by GDP-fucose pyrophosphorylase to form GDP-fucose (Ginsburg et al., *J. Biol. Chem.*, 236: 2389-2393 (1961) and Reitman, *J. Biol. Chem.*, 255: 9900-9906 (1980)). Accordingly, a fucosyltransferase catalytic domain can be linked to a catalytic domain from a GDP-fucose pyrophosphorylase, for which suitable nucleic acids are described in copending, commonly assigned U.S. patent application Ser. No. 08/826,964, filed Apr. 9, 1997. Fucokinase-encoding nucleic acids are described for, e.g., *Haemophilus influenzae* (Fleischmann et al. (1995) *Science* 269: 496-512) and *E. coli* (Lu and Lin (1989) *Nucleic Acids Res.* 17: 4883-4884).

Additional accessory enzymes from which one can obtain a catalytic domain are those that are involved in forming reactants consumed in a glycosyltransferase cycle. For example, any of several phosphate kinases are useful as accessory enzymes. Polyphosphate kinase (EC 2.7.4.1), for example, catalyzes the formation of ATP; nucleoside phosphate kinases (EC 2.7.4.4) can form the respective nucleoside diphosphates; creatine phosphate kinase (EC 2.7.3.2); myokinase (EC 2.7.4.3); N-acetylglucosamine acetyl kinase (EC 2.7.1.59); acetyl phosphate kinase; and pyruvate kinase (EC 2.7.1.40).

C. Expression Cassettes and Host Cells for Expressing Recombinant *H. pylori* α-1,3/4-fucosyltranferase Proteins Fusion proteins of the invention can be expressed in a variety of host cells, including *E. coli*, other bacterial hosts, and yeast. The host cells are preferably microorganisms, such as, for example, yeast cells, bacterial cells, or filamentous fungal cells. Examples of suitable host cells include, for example, *Azotobacter* sp. (e.g., *A. vinelandii*), *Pseudomonas* sp., *Rhizobium* sp., *Erwinia* sp., *Escherichia* sp. (e.g., *E. coli*), *Bacillus*, *Pseudomonas*, *Proteus*, *Salmonella*, *Serratia*, *Shigella*, *Rhizobia*, *Vitreoscilla*, *Paracoccus* and *Klebsiella* sp., among many others. The cells can be of any of several genera, including *Saccharomyces* (e.g., *S. cerevisiae*), *Candida* (e.g., *C. utilis*, *C. parapsilosis*, *C. krusei*, *C. versatilis*, *C. lipolytica*, *C. zeylanoides*, *C. guilliermondii*, *C. albicans*, and *C. humicola*), *Pichia* (e.g., *P. farinosa* and *P. ohmeri*), *Torulopsis* (e.g., *T. candida*, *T. sphaerica*, *T. xylinus*, *T. famata*, and *T. versatilis*), *Debaryomyces* (e.g., *D. subglobosus*, *D. cantarellii*, *D. globosus*, *D. hansenii*, and *D. japonicus*), *Zygosaccharomyces* (e.g., *Z. rouxii* and *Z. bailii*), *Kluyveromyces* (e.g., *K. marxianus*), *Hansenula* (e.g., *H. anomala* and *H. jadinii*), and *Brettanomyces* (e.g., *B. lambicus* and *B. anomalus*). Examples of useful bacteria include, but are not limited to, *Escherichia*, *Enterobacter*, *Azotobacter*, *Erwinia*, *Klebsielia*.

Typically, the polynucleotide that encodes the α-1,3/4-fucosyltranferase protein is placed under the control of a promoter that is functional in the desired host cell. An extremely wide variety of promoters are well known, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Accordingly, the invention provides expression cassettes into which the nucleic acids that encode fusion proteins are incorporated for high level expression in a desired host cell.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198: 1056), the tryptophan (trp) promoter system (Goeddel et al., *Nucleic Acids Res.* (1980) 8: 4057), the tac promoter (DeBoer, et al., *Proc. Natl. Acad. Sci. U.S.A.* (1983) 80: 21-25); and the lambda-derived $P_L$ promoter and N-gene ribosome binding site (Shimatake et al., *Nature* (1981) 292: 128). The particular promoter system is not critical to the invention, any available promoter that functions in prokaryotes can be used.

For expression of α-1,3/4-fucosyltranferase proteins in prokaryotic cells other than *E. coli*, a promoter that functions in the particular prokaryotic species is required. Such promoters can be obtained from genes that have been cloned from the species, or heterologous promoters can be used. For example, the hybrid trp-lac promoter functions in *Bacillus* in addition to *E. coli*.

A ribosome binding site (RBS) is conveniently included in the expression cassettes of the invention. An RBS in *E. coli*, for example, consists of a nucleotide sequence 3-9 nucleotides in length located 3-11 nucleotides upstream of the initiation codon (Shine and Dalgarno, *Nature* (1975) 254: 34; Steitz, *In Biological regulation and development: Gene expression* (ed. R. F. Goldberger), vol. 1, p. 349, 1979, Plenum Publishing, NY).

For expression of the α-1,3/4-fucosyltranferase proteins in yeast, convenient promoters include GAL1-10 (Johnson and Davies (1984) *Mol. Cell. Biol.* 4: 1440-1448) ADH2 (Russell et al. (1983) *J. Biol. Chem.* 258: 2674-2682), PHO5 (*EMBO J.* (1982) 6: 675-680), and MFα (Herskowitz and Oshima (1982) in *The Molecular Biology of the Yeast Saccharomyces* (eds. Strathem, Jones, and Broach) Cold Spring Harbor Lab., Cold Spring Harbor, N.Y., pp. 181-209). Another suitable promoter for use in yeast is the ADH2/GAPDH hybrid promoter as described in Cousens et al., *Gene* 61: 265-275 (1987). For filamentous fungi such as, for example, strains of the fungi *Aspergillus* (McKnight et al., U.S. Pat. No. 4,935,349), examples of useful promoters include those derived from *Aspergillus nidulans* glycolytic genes, such as the ADH3 promoter (McKnight et al., *EMBO J.* 4: 2093 2099 (1985)) and the tpiA promoter. An example of a suitable terminator is the ADH3 terminator (McKnight et al.).

Either constitutive or regulated promoters can be used in the present invention. Regulated promoters can be advantageous because the host cells can be grown to high densities before expression of the fusion proteins is induced. High level expression of heterologous proteins slows cell growth in some situations. An inducible promoter is a promoter that directs expression of a gene where the level of expression is alterable by environmental or developmental factors such as, for example, temperature, pH, anaerobic or aerobic conditions, light, transcription factors and chemicals. Such promoters are referred to herein as "inducible" promoters, which allow one to control the timing of expression of the glycosyltransferase or enzyme involved in nucleotide sugar synthesis. For *E. coli* and other bacterial host cells, inducible promoters are known to those of skill in the art. These include, for example, the lac promoter, the bacteriophage lambda $P_L$ promoter, the hybrid trp-lac promoter (Amann et al. (1983) *Gene* 25: 167; de Boer et al. (1983) *Proc. Nat'l. Acad. Sci. USA* 80: 21), and the bacteriophage T7 promoter (Studier et al. (1986) *J. Mol. Biol.*; Tabor et al. (1985) *Proc. Nat'l. Acad. Sci. USA* 82: 1074-8). These promoters and their use are discussed in Sambrook et al., supra. A particularly preferred inducible promoter for expression in prokaryotes is a dual promoter that includes a tac promoter component linked to a promoter component obtained from a gene or genes that encode enzymes involved in galactose metabolism (e.g., a promoter from a UDPgalactose 4-epimerase gene (galE)). The dual tac-gal promoter, which is described in PCT Patent Application Publ. No. WO98/20111, A construct that includes a polynucleotide of interest operably linked to gene expression control signals that, when placed in an appropriate host cell, drive expression of the polynucleotide is termed an "expression cassette." Expression cassettes that encode the fusion proteins of the invention are often placed in expression vectors for introduction into the host cell. The vectors typically include, in addition to an expression cassette, a nucleic acid sequence that enables the vector to replicate independently in one or more selected host cells. Generally, this sequence is one that enables the vector to replicate independently of the host chromosomal DNA, and includes origins of replication or autonomously replicating sequences. Such sequences are well known for a variety of bacteria. For instance, the origin of replication from the plasmid pBR322 is suitable for most Gram-negative bacteria. Alternatively, the vector can replicate by becoming integrated into the host cell genomic complement and being replicated as the cell undergoes DNA replication. A preferred expression vector for expression of the enzymes is in bacterial cells is pTGK, which includes a dual tac-gal promoter and is described in PCT Patent Application Publ. NO. WO98/20111.

The construction of polynucleotide constructs generally requires the use of vectors able to replicate in bacteria. A plethora of kits are commercially available for the purification of plasmids from bacteria (see, for example, EasyPrepJ, FlexiPrepJ, both from Pharmacia Biotech; StrataCleanJ, from Stratagene; and, QIAexpress Expression System, Qiagen). The isolated and purified plasmids can then be further manipulated to produce other plasmids, and used to transfect cells. Cloning in *Streptomyces* or *Bacillus* is also possible.

Selectable markers are often incorporated into the expression vectors used to express the polynucleotides of the invention. These genes can encode a gene product, such as a protein, necessary for the survival or growth of transformed host cells grown in a selective culture medium. Host cells not transformed with the vector containing the selection gene will not survive in the culture medium. Typical selection genes encode proteins that confer resistance to antibiotics or other toxins, such as ampicillin, neomycin, kanamycin, chloramphenicol, or tetracycline. Alternatively, selectable markers may encode proteins that complement auxotrophic deficiencies or supply critical nutrients not available from complex media, e.g., the gene encoding D-alanine racemase for Bacilli. Often, the vector will have one selectable marker that is functional in, e.g., *E. coli*, or other cells in which the vector is replicated prior to being introduced into the host cell. A number of selectable markers are known to those of skill in the art and are described for instance in Sambrook et al., supra.

Construction of suitable vectors containing one or more of the above listed components employs standard ligation techniques as described in the references cited above. Isolated plasmids or DNA fragments are cleaved, tailored, and re-ligated in the form desired to generate the plasmids required. To confirm correct sequences in plasmids constructed, the plasmids can be analyzed by standard techniques such as by restriction endonuclease digestion, and/or sequencing according to known methods. Molecular cloning techniques to achieve these ends are known in the art. A wide variety of cloning and in vitro amplification methods suitable for the construction of recombinant nucleic acids are well-known to persons of skill. Examples of these techniques and instructions sufficient to direct persons of skill through many cloning exercises are found in Berger and Kimmel, *Guide to Molecular Cloning Techniques, Methods in Enzymology*, Volume 152, Academic Press, Inc., San Diego, Calif. (Berger); and Current Protocols in Molecular Biology, F. M. Ausubel et al., eds., *Current Protocols*, a joint venture between Greene Publishing Associates, Inc. and John Wiley & Sons, Inc., (1998 Supplement) (Ausubel).

A variety of common vectors suitable for use as starting materials for constructing the expression vectors of the invention are well known in the art. For cloning in bacteria, common vectors include pBR322 derived vectors such as PBLUESCRIPT™, and λ-phage derived vectors. In yeast, vectors include Yeast Integrating plasmids (e.g., YIp5) and Yeast Replicating plasmids (the YRp series plasmids) and pGPD-2. Expression in mammalian cells can be achieved using a variety of commonly available plasmids, including pSV2, pBC12BI, and p91023, as well as lytic virus vectors (e.g., vaccinia virus, adeno virus, and baculovirus), episomal virus vectors (e.g., bovine papillomavirus), and retroviral vectors (e.g., murine retroviruses).

The methods for introducing the expression vectors into a chosen host cell are not particularly critical, and such methods are known to those of skill in the art. For example, the expression vectors can be introduced into prokaryotic cells, including E. coli, by calcium chloride transformation, and into eukaryotic cells by calcium phosphate treatment or electroporation. Other transformation methods are also suitable.

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), *J. Biol. Chem.* 263: 16297-16302.

The α-1,3/4-fucosyltranferase proteins can be expressed intracellularly, or can be secreted from the cell. Intracellular expression often results in high yields. If necessary, the amount of soluble, active fusion protein may be increased by performing refolding procedures (see, e.g., Sambrook et al., supra.; Marston et al., *Bio/Technology* (1984) 2: 800; Schoner et al., *Bio/Technology* (1985) 3: 151). In embodiments in which the α-1,3/4-fucosyltranferase proteins are secreted from the cell, either into the periplasm or into the extracellular medium, the DNA sequence is linked to a cleavable signal peptide sequence. The signal sequence directs translocation of the fusion protein through the cell membrane. An example of a suitable vector for use in *E. coli* that contains a promoter-signal sequence unit is pTA1529, which has the *E. coli* phoA promoter and signal sequence (see, e.g., Sambrook et al., supra.; Oka et al., *Proc. Natl. Acad. Sci. USA* (1985) 82: 7212; Talmadge et al., *Proc. Natl. Acad. Sci. USA* (1980) 77: 3988; Takahara et al., *J. Biol. Chem.* (1985) 260: 2670). In another embodiment, the fusion proteins are fused to a subsequence of protein A or bovine serum albumin (BSA), for example, to facilitate purification, secretion, or stability.

The α-1,3/4-fucosyltranferase proteins of the invention can also be further linked to other bacterial proteins. This approach often results in high yields, because normal prokaryotic control sequences direct transcription and translation. In *E. coli*, lacZ fusions are often used to express heterologous proteins. Suitable vectors are readily available, such as the pUR, pEX, and pMR100 series (see, e.g., Sambrook et al., supra.). For certain applications, it may be desirable to cleave the non-glycosyltransferase and/or accessory enzyme amino acids from the fusion protein after purification. This can be accomplished by any of several methods known in the art, including cleavage by cyanogen bromide, a protease, or by Factor $X_a$ (see, e.g., Sambrook et al., supra.; Itakura et al., *Science* (1977) 198: 1056; Goeddel et al., *Proc. Natl. Acad. Sci. USA* (1979) 76: 106; Nagai et al., *Nature* (1984) 309: 810; Sung et al., *Proc. Natl. Acad. Sci. USA* (1986) 83: 561). Cleavage sites can be engineered into the gene for the fusion protein at the desired point of cleavage.

More than one recombinant protein may be expressed in a single host cell by placing multiple transcriptional cassettes in a single expression vector, or by utilizing different selectable markers for each of the expression vectors which are employed in the cloning strategy.

A suitable system for obtaining recombinant proteins from *E. coli* which maintains the integrity of their N-termini has been described by Miller et al. *Biotechnology* 7:698-704 (1989). In this system, the gene of interest is produced as a C-terminal fusion to the first 76 residues of the yeast ubiquitin gene containing a peptidase cleavage site. Cleavage at the junction of the two moieties results in production of a protein having an intact authentic N-terminal reside.

D. Purification of α-1,3/4-Fucosyltranferase Proteins

The *H. pylori* fucosyltransferase proteins of the present invention can be expressed as intracellular proteins or as proteins that are secreted from the cell, and can be used in this form, in the methods of the present invention. For example, a crude cellular extract containing the expressed intracellular or secreted *H. pylori* fucosyltransferase protein can used in the methods of the present invention.

Alternatively, the *H. pylori* fucosyltransferase proteins can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol. 182: Guide to Protein Purfication.*, Academic Press, Inc. N.Y. (1990)). Substantially pure compositions of at least about 70 to 90% homogeneity are preferred, and 98 to 99% or more homogeneity are most preferred. The purified proteins may also be used, e.g., as immunogens for antibody production.

To facilitate purification of the *H. pylori* α-1,3/4-fucosyltranferase proteins of the invention, the nucleic acids that encode the fusion proteins can also include a coding sequence for an epitope or "tag" for which an affinity binding reagent is available, i.e. a purification tag. Examples of suitable epitopes include the myc and V-5 reporter genes; expression vectors useful for recombinant production of fusion proteins having these epitopes are commercially available (e.g., Invitrogen (Carlsbad Calif.) vectors pcDNA3.1/Myc-His and pcDNA3.1/V5-His are suitable for expression in mammalian cells). Additional expression vectors suitable for attaching a tag to the *H. pylori* α-1,3/4-fucosyltranferase proteins of the invention, and corresponding detection systems are known to those of skill in the art, and several are commercially available (e.g., FLAG" (Kodak, Rochester N.Y.). Another example of a suitable tag is a polyhistidine sequence, which is capable of binding to metal chelate affinity ligands. Typically, six adjacent histidines (SEQ ID NO:81) are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In Genetic Engineering: Principles and Methods, J. K. Setlow, Ed., Plenum Press, NY; commercially available from Qiagen (Santa Clarita, Calif.)).

Purification tags also include maltose binding domains and starch binding domains. Purification of maltose binding domain proteins is know to those of skill in the art. Starch binding domains are described in WO 99/15636, herein incorporated by reference. Affinity purification of a fusion protein comprising a starch binding domain using a betacyclodextrin (BCD)-derivatized resin is described in U.S. Ser. No. 60/468,374, filed May 5, 2003, herein incorporated by reference in its entirety.

Other haptens that are suitable for use as tags are known to those of skill in the art and are described, for example, in the Handbook of Fluorescent Probes and Research Chemicals (6th Ed., Molecular Probes, Inc., Eugene Oreg.). For example, dinitrophenol (DNP), digoxigenin, barbiturates (see, e.g., U.S. Pat. No. 5,414,085), and several types of fluorophores are useful as haptens, as are derivatives of these compounds. Kits are commercially available for linking haptens and other moieties to proteins and other molecules. For example, where the hapten includes a thiol, a heterobifunctional linker such as SMCC can be used to attach the tag to lysine residues present on the capture reagent.

One of skill would recognize that modifications can be made to the α-1,3/4-fucosyltranferase catalytic or functional domains without diminishing their biological activity. Some modifications may be made to facilitate the cloning, expression, or incorporation of the catalytic domain into a fusion protein. Such modifications are well known to those of skill in the art and include, for example, the addition of codons at either terminus of the polynucleotide that encodes the catalytic domain to provide, for example, a methionine added at the amino terminus to provide an initiation site, or additional amino acids (e.g., poly His) placed on either terminus to create conveniently located restriction enzyme sites or termination codons or purification sequences.

E. Uses of the *H. pylori* Fucosyltransferase Proteins

The invention provides *H. pylori* α-1,3/4-fucosyltranferase proteins and methods of using the *H. pylori* α-1,3/4-fucosyltranferase proteins to enzymatically synthesize glycoproteins, glycolipids, and oligosaccharide moieties. The glycosyltransferase reactions of the invention take place in a reaction medium comprising at least one *H. pylori* α-1,3/4-fucosyltranferase, acceptor substrate, and donor substrate, and typically a soluble divalent metal cation. In some embodiments, accessory enzymes and substrates for the accessory enzyme catalytic moiety are also present, so that the accessory enzymes can synthesize the donor substrate for the *H. pylori* α-1,3/4-fucosyltranferase.

A number of methods of using glycosyltransferases to synthesize glycoproteins and glycolipids having desired oligosaccharide moieties are known. Exemplary methods are described, for instance, WO 96/32491, Ito et al. (1993) *Pure Appl. Chem.* 65: 753, and U.S. Pat. Nos. 5,352,670, 5,374,541, and 5,545,553.

The *H. pylori* fucosyltransferase proteins prepared as described herein can be used in combination with additional glycosyltransferases. For example, one can use a combination of recombinant sialyltransferase fusion protein and a recombinant *H. pylori* α-1,3/4-fucosyltranferases. By conducting two glycosyltransferase reactions in sequence in a single vessel, overall yields are improved over procedures in which an intermediate species is isolated. Moreover, cleanup and disposal of extra solvents and by-products is reduced. Similarly, the recombinant glycoosyltransferases can be used with recombinant accessory enzyme, which may or may not be present as a the fusion protein. In other embodiments, the *H. pylori* α-1,3/4-fucosyltranferase and additional glycosyltransferases or accessory enzymes are produced in the same cell and used to synthesize a desired end product.

The products produced by the above processes can be used without purification. However, standard, well known techniques, for example, thin or thick layer chromatography, ion exchange chromatography, or membrane filtration can be used for recovery of glycosylated saccharides. Also, for example, membrane filtration, utilizing a nanofiltration or reverse osmotic membrane as described in commonly assigned AU Patent No. 735695 may be used. As a further example, membrane filtration wherein the membranes have a molecular weight cutoff of about 1000 to about 10,000 Daltons can be used to remove proteins. As another example, nanofiltration or reverse osmosis can then be used to remove salts. Nanofilter membranes are a class of reverse osmosis membranes which pass monovalent salts but retain polyvalent salts and uncharged solutes larger than about 200 to about 1000 Daltons, depending upon the membrane used. Thus, for example, the oligosaccharides produced by the compositions and methods of the present invention can be retained in the membrane and contaminating salts will pass through.

F. Donor Substrates and Acceptor Substrates

Suitable donor substrates used by the *H. pylori* fucosyltransferase proteins and other glycosyltranferases in the methods of the invention include, but are not limited to, UDP-Glc, UDP-GlcNAc, UDP-Gal, UDP-GalNAc, GDP-Man, GDP-Fuc, UDP-GlcUA, and CMP-sialic acid. Guo et al., *Applied Biochem. and Biotech.* 68: 1-20 (1997).

Suitable acceptor substrates used by the *H. pylori* fucosyltransferase proteins and methods of the invention include, but are not limited to, polysaccharides, oligosaccharides, lipids, and glycolipids. For example, the oligosaccharide LNnT can be fucosylated to form LNFIII. The fucosyltmaferases described herein can also be used in multienzyme systems to produce a desired product from a convenient starting material. For example, LNFIII was prepared on a multigram scale from lactose using the *H. pylori* α-1,3/4-fucosyltranferases from strain 1182 described herein, in combination with *Neisseria gonococcus* β-1,3N-acetylglucosaminyltransferase (lgtA) and *Neisseria gonococcus* β-1,4-galactosyltransferase (lgtB).

Suitable acceptor substrates used by the *H. pylori* fucosyltransferase proteins and methods of the invention include, but are not limited to, proteins, lipids, gangliosides and other biological structures (e.g., whole cells) that can be modified by the methods of the invention. Exemplary structures, which can be modified by the methods of the invention include any a of a number glycolipids, glycoproteins and carbohydrate structures on cells known to those skilled in the art as set forth is Table 1.

TABLE 1

Hormones and Growth Factors

G-CSF
GM-CSF
TPO
EPO
EPO variants
α-TNF
Leptin

Enzymes and Inhibitors t-PA
t-PA variants
Urokinase
Factors VII, VIII, IX, X
DNase
Glucocerebrosidase
Hirudin
α1 antitrypsin
Antithrombin III Cytokines and Chimeric Cytokines Interleukin-1 (IL-1), 1B, 2, 3, 4
Interferon-α (IFN-α)
IFN-α-2b
IFN-β
IFN-γ
Chimeric diptheria toxin-IL-2

TABLE 1-continued

Receptors and Chimeric Receptors

CD4
Tumor Necrosis Factor (TNF) receptor
Alpha-CD20
MAb-CD20
MAb-alpha-CD3
MAb-TNF receptor
MAb-CD4
PSGL-1
MAb-PSGL-1
Complement
GlyCAM or its chimera
N-CAM or its chimera
LFA-3
CTLA-IV Monoclonal Antibodies (Immunoglobulins)

MAb-anti-RSV
MAb-anti-IL-2 receptor
MAb-anti-CEA
MAb-anti-platelet IIb/IIIa receptor
MAb-anti-EGF
MAb-anti-Her-2 receptor Cells Red blood cells
White blood cells (e.g., T cells, B cells, dendritic cells, macrophages, NK cells, neutrophils, monocytes and the like
Stem cells Examples of suitable acceptor substrates used in fucosyltransferase-catalyzed reactions, and examples of suitable acceptor substrates used in sialyltransferase-catalyzed reactions are described in Guo et al., Applied Biochem. and Biotech. 68: 1-20 (1997), but are not limited thereto.

The present invention provides H. pylori fucosyltransferase proteins (e.g., fucosyltransferases) that are selected for their ability to produce glycoproteins and glycolipids having desired oligosaccharide moieties. Similarly, if present, accessory enzymes are chosen based on an desired activated sugar substrate or on a sugar found on the product oligosaccharide.

One can readily identify suitable H. pylori fucosyltransferase proteins by reacting various amounts of a H. pylori α-1,3/4-fucosyltranferase protein of interest (e.g., 0.01-100 mU/mg protein) with a glycoprotein (e.g., at 1-10 mg/ml) to which is linked an oligosaccharide that has a potential acceptor site for glycosylation by the fusion protein of interest. The abilities of the recombinant glycosyltransferases fusion proteins of the present invention to add a sugar residue at the desired acceptor site are compared, and a H. pylori fucosyltransferase protein having the desired property (e.g., acceptor substrate specificity or catalytic activity) is selected.

In general, the efficacy of the enzymatic synthesis of glycoproteins and glycolipids, having desired oligosaccharide moieties, can be enhanced through use of recombinantly produced H. pylori α-1,3/4-fucosyltranferasesproteins of the present invention. Recombinant techniques enable production of the recombinant H. pylori α-1,3/4-fucosyltranferase proteins in the large amounts that are required for large-scale glycoprotein and glycolipid modification.

Suitable glycoproteins and glycolipids for use by the H. pylori fucosyltransferase proteins and methods of the invention can be glycoproteins and glycolipids immobilized on a solid support during the glycosylation reaction. The term "solid support" also encompasses semi-solid supports. Preferably, the target glycoprotein or glycolipid is reversibly immobilized so that the respective glycoprotein or glycolipid can be released after the glycosylation reaction is completed. Many suitable matrices are known to those of skill in the art. Ion exchange, for example, can be employed to temporarily immobilize a glycoprotein or glycolipid on an appropriate resin while the glycosylation reaction proceeds. A ligand that specifically binds to the glycoprotein or glycolipid of interest can also be used for affinity-based immobilization. For example, antibodies that specifically bind to a glycoprotein are suitable. Also, where the glycoprotein of interest is itself an antibody or contains a fragment thereof, one can use protein A or G as the affinity resin. Dyes and other molecules that specifically bind to a glycoprotein or glycolipid of interest are also suitable.

The recombinant fusion protein of the invention can be constructed and expressed as a fusion protein with a molecular "tag" at one end, which facilitates purification of the protein, i.e., a purification tag. Such tags can also be used for immobilization of a protein of interest during the glycosylation reaction. Suitable tags include "epitope tags," which are a protein sequence that is specifically recognized by an antibody. Epitope tags are generally incorporated into fusion proteins to enable the use of a readily available antibody to unambiguously detect or isolate the fusion protein. A "FLAG tag" is a commonly used epitope tag, specifically recognized by a monoclonal anti-FLAG antibody, consisting of the sequence AspTyrLysAspAspAspAspLys (SEQ ID NO:80) or a substantially identical variant thereof. A mcy tag is another commonly used epitope tag. Other suitable tags are known to those of skill in the art, and include, for example, an affinity tag such as a hexahistidine (SEQ ID NO:81) peptide, which will bind to metal ions such as nickel or cobalt ions. Purification tags also include maltose binding domains and starch binding domains. Purification of maltose binding domain proteins is know to those of skill in the art. Starch binding domains are described in WO 99/15636, herein incorporated by reference. Affinity purification of a fusion protein comprising a starch binding domain using a betacylodextrin (BCD)-derivatized resin is described in U.S. Ser. No. 60/468,374, filed May 5, 2003, herein incorporated by reference in its entirety.

Preferably, when the glycoprotein is a truncated version of the full-length glycoprotein, it preferably includes the biologically active subsequence of the full-length glycoprotein. Exemplary biologically active subsequences include, but are not limited to, enzyme active sites, receptor binding sites, ligand binding sites, complementarity determining regions of antibodies, and antigenic regions of antigens.

In some embodiments, the H. pylori fucosyltransferase proteins and methods of the present invention are used to enzymatically synthesize a glycoprotein or glycolipid that has a substantially uniform glycosylation pattern. The glycoproteins and glycolipids include a saccharide or oligosaccharide that is attached to a protein, glycoprotein, lipid, or glycolipid for which a glycoform alteration is desired. The saccharide or oligosaccharide includes a structure that can function as an acceptor substrate for a glycosyltransferase. When the acceptor substrate is glycosylated, the desired oligosaccharide moiety is formed. The desired oligosaccharide moiety is one that imparts the desired biological activity upon the glycoprotein or glycolipid to which it is attached. In the compositions of the invention, the preselected saccharide residue is linked to at least about 30% of the potential acceptor sites of interest. More preferably, the preselected saccharide residue is linked to at least about 50% of the potential acceptor substrates of interest, and still more preferably to at least 70% of the potential acceptor substrates of interest. In situations in which the starting glycoprotein or glycolipid exhibits heterogeneity in the oligosaccharide moiety of interest (e.g., some of the oligosaccharides on the starting glycoprotein or glycolipid already have the preselected saccharide residue attached to the acceptor substrate of interest), the recited percentages include such pre-attached saccharide residues.

The term "altered" refers to the glycoprotein or glycolipid of interest having a glycosylation pattern that, after application of the *H. pylori* fucosyltransferase proteins and methods of the invention, is different from that observed on the glycoprotein as originally produced. An example of such glycoconjugates are glycoproteins in which the glycoforms of the glycoproteins are different from those found on the glycoprotein when it is produced by cells of the organism to which the glycoprotein is native. Also provided are *H. pylori* fucosyltransferase proteins and methods of using such fusion proteins for enzymatically synthesizing glycoproteins and glycolipids in which the glycosylation pattern of these glycoconjugates are modified compared to the glycosylation pattern of the glycoconjugates as originally produced by a host cell, which can be of the same or a different species than the cells from which the native glycoconjugates are produced.

One can assess differences in glycosylation patterns not only by structural analysis of the glycoproteins and glycolipids, but also by comparison of one or more biological activities of the glycoconjugates. For example, a glycoprotein having an "altered glycoform" includes one that exhibits an improvement in one more biological activities of the glycoprotein after the glycosylation reaction compared to the unmodified glycoprotein. For example, an altered glycoconjugate includes one that, after application of the *H. pylori* fucosyltransferase proteins and methods of the invention, exhibits a greater binding affinity for a ligand or receptor of interest, a greater therapeutic half-life, reduced antigenicity, and targeting to specific tissues. The amount of improvement observed is preferably statistically significant, and is more preferably at least about a 25% improvement, and still more preferably is at least about 50%, 60%, 70%, and even still more preferably is at least 80%.

G. Fucosyltransferase Reactions

The *H. pylori* fucosyltransferase proteins, acceptor substrates, donor substrates and other reaction mixture ingredients, including other glycosyltransferases and accessory enzymes are combined by admixture in an aqueous reaction medium. The medium generally has a pH value of about 5 to about 8.5. The selection of a medium is based on the ability of the medium to maintain pH value at the desired level. Thus, in some embodiments, the medium is buffered to a pH value of about 7.5. If a buffer is not used, the pH of the medium should be maintained at about 5 to 8.5, depending upon the particular glycosyltransferase used. For fucosyltransferases, the pH range is preferably maintained from about 6.0 to 8.0. For sialyltransferases, the range is preferably from about 5.5 and about 7.5.

Enzyme amounts or concentrations are expressed in activity units, which is a measure of the initial rate of catalysis. One activity unit catalyzes the formation of 1 μmol of product per minute at a given temperature (typically 37° C.) and pH value (typically 7.5). Thus, 10 units of an enzyme is a catalytic amount of that enzyme where 10 μmol of substrate are converted to 10 μmol of product in one minute at a temperature of 37° C. and a pH value of 7.5.

The reaction mixture may include divalent metal cations ($Mg^{2+}$, $Mn^{2+}$). The reaction medium may also comprise solubilizing detergents (e.g., Triton or SDS) and organic solvents such as methanol or ethanol, if necessary. The enzymes can be utilized free in solution or can be bound to a support such as a polymer. The reaction mixture is thus substantially homogeneous at the beginning, although some precipitate can form during the reaction.

The temperature at which an above process is carried out can range from just above freezing to the temperature at which the most sensitive enzyme denatures. That temperature range is preferably about 0° C. to about 45° C., and more preferably at about 20° C. to about 37° C.

The reaction mixture so formed is maintained for a period of time sufficient to obtain the desired high yield of desired oligosaccharide products, including determinants present on oligosaccharide groups attached to the glycoprotein to be glycosylated. For large-scale preparations, the reaction will often be allowed to proceed for between about 0.5-240 hours, and more typically between about 1-18 hours.

In embodiments in which more than one glycosyltransferase is used to obtain the oligosaccharide products, the enzymes and reagents for a second glycosyltransferase reaction can be added to the reaction medium once the first glycosyltransferase reaction has neared completion. For some combinations of enzymes, the glycosyltransferases and corresponding substrates can be combined in a single initial reaction mixture; the enzymes in such simultaneous reactions preferably do not form a product that cannot serve as an acceptor for the other enzyme. By conducting two glycosyltransferase reactions in sequence in a single vessel, overall yields are improved over procedures in which an intermediate species is isolated. Moreover, cleanup and disposal of extra solvents and by-products is reduced. In addition, in some embodiments, the fucosyltransferase and additionally glycosyltransferases or accessory enzymes are expressed in the same host cell and the desired product is synthesized within the host cell.

One or more of the glycosyltransferase reactions can be carried out as part of a glycosyltransferase cycle. Preferred conditions and descriptions of glycosyltransferase cycles have been described. A number of glycosyltransferase cycles (for example, sialyltransferase cycles, galactosyltransferase cycles, and fucosyltransferase cycles) are described in U.S. Pat. No. 5,374,541 and WO 9425615 A. Other glycosyltransferase cycles are described in Ichikawa et al. *J. Am. Chem. Soc.* 114: 9283 (1992), Wong et al. *J. Org. Chem.* 57: 4343 (1992), DeLuca, et al., *J. Am. Chem. Soc.* 117:5869-5870 (1995), and Ichikawa et al. In *Carbohydrates and Carbohydrate Polymers.* Yaltami, ed. (ATL Press, 1993).

Other glycosyltransferases can be substituted into similar transferase cycles as have been described in detail for the fucosyltransferases and sialyltransferases. In particular, the glycosyltransferase can also be, for instance, glucosyltransferases, e.g., Alg8 (Stagljov et al., *Proc. Natl. Acad. Sci. USA* 91:5977 (1994)) or Alg5 (Heesen et al. *Eur. J. Biochem.* 224:71 (1994)), N-acetylgalactosaminyltransferases such as, for example, α(1,3) N-acetylgalactosaminyltransferase, β(1,4) N-acetylgalactosaminyltransferases (Nagata et al. *J. Biol. Chem.* 267:12082-12089 (1992) and Smith et al. *J. Biol. Chem.* 269:15162 (1994)) and polypeptide N-acetylgalactosaminyltransferase (Homa et al. *J. Biol. Chem.* 268:12609 (1993)). Suitable N-acetylglucosaminyltransferases include GnTI (2.4.1.101, Hull et al., *BBRC* 176:608 (1991)), GnTII, and GnTIII (Ihara et al. *J. Biochem.* 113:692 (1993)), GnTV (Shoreiban et al. *J. Biol. Chem.* 268: 15381 (1993)), O-linked N-acetylglucosaminyltransferase (Bierhuizen et al. *Proc. Natl. Acad. Sci. USA* 89:9326 (1992)), N-acetylglucosamine-1-phosphate transferase (Rajput et al. *Biochem J.* 285:985 (1992), and hyaluronan synthase. Suitable mannosyltransferases include α(1,2) mannosyltransferase, α(1,3) mannosyltransferase, β(1,4) mannosyltransferase, Dol-P-Man synthase, OCh1, and Pmt1.

For the above glycosyltransferase cycles, the concentrations or amounts of the various reactants used in the processes depend upon numerous factors including reaction conditions such as temperature and pH value, and the choice and amount of acceptor saccharides to be glycosylated. Because the glycosylation process permits regeneration of activating nucleotides, activated donor sugars and scavenging of produced PPi in the presence of catalytic amounts of the enzymes, the process is limited by the concentrations or amounts of the stoichiometric substrates discussed before. The upper limit for the concentrations of reactants that can be used in accordance with the method of the present invention is determined by the solubility of such reactants.

Preferably, the concentrations of activating nucleotides, phosphate donor, the donor sugar and enzymes are selected such that glycosylation proceeds until the acceptor is consumed.

Each of the enzymes is present in a catalytic amount. The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

The fucosyltransferase reaction can be carried out using an oligosaccharide or polysaccharide as an acceptor molecule. Suitable acceptor substrates used by the *H. pylori* fucosyltransferase proteins and methods of the invention include, but are not limited to, polysaccharides, oligosaccharides, lipids, glycolipids, and glycoproteins. For example, the oligosaccharide LNnT can be fucosylated to form LNFIII. The fucosyltransferases described herein can also be used in multienzyme systems to produce a desired product from a convenient starting material. For example, LNFIII was prepared on a multigram scale from lactose using the *H. pylori* α-1,3/4-fucosyltranferases from strain 1182 described herein, in combination with *Neisseria gonococcus* β-1,3N-acetylglucosaminyltransferase (lgtA) and *Neisseria gonococcus* β-1,4-galactosyltransferase (lgtB).

The recombinant fucosyltransferase fusion protein used in the methods of the invention is chosen based upon its ability to fucosylate the fucosyltransferase acceptor substrates of interest. Preferably, the fucosyltransferase is assayed for suitability using a fucosyltransferase acceptor substrate that is attached to a soluble saccharide or oligosaccharide. The use of a soluble saccharide or oligosaccharide acceptor substrate in the assay to determine fucosyltransferase activity allows one to select a fucosyltransferase that produces the desired oligosaccharide product.

The fucosyltransferase reaction can be carried out using a lipid or glycolipid as an acceptor molecule. Many saccharides require the presence of particular fucosylated structures in order to exhibit biological activity. Intercellular recognition mechanisms often require a fucosylated oligosaccharide. For example, a number of proteins that function as cell adhesion molecules, including P-selectin, E-selectin, bind specific cell surface fucosylated carbohydrate structures, for example, the sialyl Lewis x and the sialyl Lewis a structures. In addition, the specific carbohydrate structures that form the ABO blood group system are fucosylated. The carbohydrate structures in each of the three groups share a Fucα1,2Galβ1-disaccharide unit. In blood group O structures, this disaccharide is the terminal structure. The group A structure is formed by an α1,3 GalNAc transferase that adds a terminal GalNAc residue to the dissacharide. The group B structure is formed by an α1,3 galactosyltransferase that adds terminal galactose residue. The Lewis blood group structures are also fucosylated. For example the Lewis x and Lewis a structures are Galβ1,4 (Fucα1,3)GlcNac and Galβ1,4(Fucα1,4)GlcNac, respectively. Both these structures can be further sialylated (NeuAcα2,3-) to form the corresponding sialylated structures. Other Lewis blood group structures of interest are the Lewis y and b structures which are Fucα1,2Galβ1,4(Fucα1, 3)GlcNAcβ-OR and Fucα1,2Galβ1,3(Fucα1,4)GlcNAc-OR, respectively. For a description of the structures of the ABO and Lewis blood group stuctures and the enzymes involved in their synthesis see, *Essentials of Glycobiology*, Varki et al. eds., Chapter 16 (Cold Spring Harbor Press, Cold Spring Harbor, N.Y., 1999).

The recombinant fucosyltransferase fusion protein used in the methods of the invention is chosen based upon its ability to fucosylate the fucosyltransferase acceptor substrates of interest. Preferably, the fucosyltransferase is assayed for suitability using a fucosyltransferase acceptor substrate that is attached to a lipid or glycolipid. The use of a glycolipid-linked acceptor substrate, rather than an acceptor substrate that is part of a soluble oligosaccharide, in the assay to determine fucosyltransferase activity allows one to select a fucosyltransferase that produces the selected fucosylation pattern on the glycolipid.

Fucosyltransferases have been used in synthetic pathways to transfer a fucose unit from guanosine-5'-diphosphofucose to a specific hydroxyl of a saccharide acceptor. For example, Ichikawa prepared sialyl Lewis-X by a method that involves the fucosylation of sialylated lactosamine with a cloned fucosyltransferase (Ichikawa et al., *J. Am. Chem. Soc.* 114: 9283-9298 (1992)). Lowe has described a method for expressing non-native fucosylation activity in cells, thereby producing fucosylated glycoproteins, cell surfaces, etc. (U.S. Pat. No. 5,955,347).

In one embodiment, the methods of the invention are practiced by contacting a substrate, having an acceptor moiety for a fucosyltransferase, with a reaction mixture that includes a fucose donor moiety, a fucosyltransferase, and other reagents required for fucosyltransferase activity. The substrate is incubated in the reaction mixture for a sufficient time and under appropriate conditions to transfer fucose from the fucose donor moiety to the fucosyltransferase acceptor moiety. In preferred embodiments, the fucosyltransferase catalyzes the fucosylation of at least 60% of the fucosyltransferase respective acceptor moieties in the composition.

Specificity for a selected substrate is only the first criterion a preferred fucosyltransferase should satisfy. The fucosyltransferase used in the method of the invention is preferably also able to efficiently fucosylate a variety of substrates, and support scale-up of the reaction to allow the fucosylation of at least about 500 mg of the substrate. More preferably, the fucosyltransferase will support the scale of the fucosylation reaction to allow the synthesis of at least about 1 kg, and more preferably, at least 10 kg of substrate with relatively low cost and infrastructure requirements.

Suitable acceptor moieties for fucosyltransferase-catalyzed attachment of a fucose residue include, but are not limited to, GlcNAc-OR, Galβ1,3GlcNAc-OR, NeuAcα2, 3Galβ1,3GlcNAc-OR, Galβ1,4GlcNAc-OR and NeuAcα2, 3Galβ1,4GlcNAc-OR, where R is an amino acid, a saccharide, an oligosaccharide or an aglycon group having at least one carbon atom. R is linked to or is part of a substrate. The appropriate fucosyltransferase for a particular reaction is chosen based on the type of fucose linkage that is desired (e.g., α2, α3, or α4), the particular acceptor of interest, and the ability of the fucosyltransferase to achieve the desired high yield of fucosylation. Suitable fucosyltransferases and their properties are described above.

If a sufficient proportion of the substrate-linked oligosaccharides in a composition does not include a fucosyltransferase acceptor moiety, one can synthesize a suitable acceptor. For example, one preferred method for synthesizing an acceptor for a fucosyltransferase involves use of a GlcNAc transferase to attach a GlcNAc residue to a GlcNAc transferase acceptor moiety, which is present on the substrate-linked oligosaccharides. In preferred embodiments a transferase is chosen, having the ability to glycosylate a large fraction of the potential acceptor moieties of interest. The resulting GlcNAcβ-OR can then be used as an acceptor for a fucosyltransferase.

The resulting GlcNAcβ-OR moiety can be galactosylated prior to the fucosyltransferase reaction, yielding, for example, a Galβ1,3GlcNAc-OR or Gal β1,4GlcNAc-OR residue. In some embodiments, the galactylation and fucosylation steps can be carried out simultaneously. By choosing a fucosyltransferase that requires the galactosylated acceptor, only the desired product is formed. Thus, this method involves:

(a) galactosylating a compound of the formula GlcNAcβ-OR with a galactosyltransferase in the presence of a UDP-galactose under conditions sufficient to form the compounds Galβ1,4GlcNAcβ-OR or Galβ1,3GlcNAc-OR; and (b) fucosylating the compound formed in (a) using a fucosyltransferase in the presence of GDP-fucose under conditions sufficient to form a compound selected from:

Fucα1,2Galβ1,4GlcNAc1β-O1R;
Fucα1,2Galβ1,3GlcNAc-OR;
Fucα1,2Galβ1,4GalNAc 1-O1R;
Fucα1,2Galβ1,3GalNAc-OR;
Galβ1,4(Fuc1,α3)GlcNAcβ-OR; or
Galβ1,3(Fucα1,4)GlcNAc-OR.

One can add additional fucose residues to the above structures by including an additional fucosyltransferase, which has the desired activity. For example, the methods can form oligosaccharide determinants such as Fucα1,2Galβ1,4(Fucα1,3)GlcNAcβ-OR and Fucα1,2Galβ1,3(Fucα1,4)GlcNAc-OR. Thus, in another preferred embodiment, the method includes the use of at least two fucosyltransferases. The multiple fucosyltransferases are used either simultaneously or sequentially. When the fucosyltransferases are used sequentially, it is generally preferred that the glycoprotein is not purified between the multiple fucosylation steps. When the multiple fucosyltransferases are used simultaneously, the enzymatic activity can be derived from two separate enzymes or, alternatively, from a single enzyme having more than one fucosyltransferase activity.

The fucosyltransferase reaction can carried out by contacting recombinant fucosyltransferase protein of the present invention with a mixture that includes, for example, multiple copies of a glycoprotein species, a majority of which preferably have one or more linked oligosaccharide groups that include an acceptor substrate for a fucosyltransferase; fucose donor substrate; and other reagents required for fucosyltransferase activity. The glycoprotein is incubated in the reaction mixture for a sufficient time and under appropriate conditions to transfer fucose from a donor substrate to a fucosyltransferase acceptor substrate.

The recombinant fucosyltransferase fusion protein used in the methods of the invention is chosen based upon its ability to fucosylate the fucosyltransferase acceptor substrates of interest. Preferably, the fucosyltransferase is assayed for suitability using a fucosyltransferase acceptor substrate that is attached to a glycoprotein. The use of a glycoprotein-linked acceptor substrate, rather than an acceptor substrate that is part of a soluble oligosaccharide, in the assay to determine fucosyltransferase activity allows one to select a fucosyltransferase that produces the selected fucosylation pattern on the glycoprotein.

In a preferred embodiment, the recombinant fucosyltransferase fusion protein of the present invention has a high level of expression in cells and/or high enzymatic activity (e.g., high specificity for a selected substrate and/or high catalytic activity). In another preferred embodiment, the fucosyltransferase is useful in a method for fucosylating a commercially important recombinant or transgenic glycoprotein. The fucosyltransferase used in the method of the invention is preferably also able to efficiently fucosylate a variety of glycoproteins, and support scale-up of the reaction to allow the fucosylation of at least about 500 mg of the glycoprotein. More preferably, the fucosyltransferase will support the scale of the fucosylation reaction to allow the synthesis of at least about 1 kg, and more preferably, at least 10 kg of recombinant glycoprotein with relatively low cost and infrastructure requirements.

In an exemplary embodiment, the method of the invention results in the formation on a glycoprotein of at least one ligand for a selectin. Confirmation of the formation of the ligand is assayed in an operational manner by probing the ability of the glycoprotein to interact with a selectin. The interaction between a glycoprotein and a specific selectin is measurable by methods familiar to those in the art (see, for example, Jutila et al., *J. Immunol.* 153: 3917-28 (1994); Edwards et al., *Cytometry* 43(3): 211-6 (2001); Stahn et al., *Glycobiology* 8: 311-319 (1998); Luo et al., *J. Cell Biochem.* 80(4):522-31 (2001); Dong et al., *J. Biomech.* 33(1): 35-43 (2000); Jung et al., *J. Immunol.* 162(11): 6755-62 (1999); Keramidaris et al., *J. Allergy Clin. Immunol.* 107(4): 734-8 (2001); Fieger et al., *Biochim. Biophys. Acta* 1524(1): 75-85 (2001); Bruehl et al., *J. Biol. Chem.* 275(42): 32642-8 (2000); Tangemann et al., *J. Exp. Med.* 190(7): 935-42 (1999); Scalia et al., *Circ. Res.* 84(1): 93-102 (1999); Alon et al., *J. Cell Biol.* 138(5): 1169-80 (1997); Steegmaier et al., *Eur. J. Immunol.* 27(6): 1339-45 (1997); Stewart et al., *J. Med. Chem.* 44(6): 988-1002 (2001); Schurmann et al, *Gut* 36(3): 411-8 (1995); Burrows et al., *J. Clin. Pathol.* 47(10): 939-44 (1994)).

Suitable acceptor substrates for fucosyltransferase-catalyzed attachment of a fucose residue include, but are not limited to, GlcNAc-OR, Galβ1,3GlcNAc-OR, NeuAcα2,3 Galβ1,3GlcNAc-OR, Galβ1,4GlcNAc-OR and NeuAcα2, 3Galβ1,4GlcNAc-OR, where R is an amino acid, a saccharide, an oligosaccharide or an aglycon group having at least one carbon atom. R is linked to or is part of a glycoprotein. The appropriate fucosyltransferase for a particular reaction is chosen based on the type of fucose linkage that is desired (e.g., α2, α3, or α4), the particular acceptor of interest, and the ability of the fucosyltransferase to achieve the desired high yield of fucosylation. Suitable fucosyltransferases and their properties are described above.

If a sufficient proportion of the glycoprotein-linked oligosaccharides in a composition does not include a fucosyltransferase acceptor substrate, one can synthesize a suitable acceptor. For example, one preferred method for synthesizing an acceptor for a fucosyltransferase involves use of a GlcNAc transferase to attach a GlcNAc residue to a GlcNAc transferase acceptor substrate, which is present on the glycoprotein-linked oligosaccharides. In preferred embodiments a transferase is chosen, having the ability to glycosylate a large fraction of the potential acceptor substrates of interest. The resulting GlcNAcβ-OR can then be used as an acceptor for a fucosyltransferase.

The resulting GlcNAcβ-OR moiety can be galactosylated prior to the fucosyltransferase reaction, yielding, for example, a Galβ1,3GlcNAc-OR or Gal β1,4GlcNAc-OR residue. In some embodiments, the galactosylation and fucosylation steps are carried out simultaneously. Thus, this method involves:

(a) galactosylating a compound of the formula GlcNAcβ-OR with a galactosyltransferase in the presence of a UDP-galactose under conditions sufficient to form the compounds Galβ1,4GlcNAcβ-OR or Galβ1,3GlcNAc-OR; and (b) fucosylating the compound formed in (a) using a fucosyltransferase in the presence of GDP-fucose under conditions sufficient to form a compound selected from:
Fucα1,2Gal 1,4GlcNAc1β-O1R;
Fucα1,2Galβ1,3GlcNAc-OR;
Fucα1,2Galβ1,4GalNAc1β-O1R;
Fucα1,2Galβ1,3GalNAc-OR;
Galβ1,4(Fuc1,α3)GlcNAcβ-OR; or
Galβ1,3(Fucα1,4)GlcNAc-OR.

One can add additional fucose residues to a fucosylated glycoprotein treating the fucosylated peptide with a fucosyltransferase, which has the desired activity. For example, the methods can form oligosaccharide determinants such as Fucα1,2Galβ1,4(Fucα1,3)GlcNAcβ-OR and Fucα1,2Galβ1,3(Fucα1,4)GlcNAc-OR. Thus, in another preferred embodiment, the method includes the use of at least two fucosyltransferases. The multiple fucosyltransferases are used either simultaneously or sequentially. When the fucosyltransferases are used sequentially, it is generally preferred that the glycoprotein is not purified between the multiple fucosylation steps. When the multiple fucosyltransferases are used simultaneously, the enzymatic activity can be derived from two separate enzymes or, alternatively, from a single enzyme having more than one fucosyltransferase activity.

H. Multiple-Enzyme Oligosaccharide Synthesis

As discussed above, in some embodiments, two or more enzymes may be used to form a desired oligosaccharide or oligosaccharide determinant on a glycoprotein or glycolipid. For example, a particular oligosaccharide determinant might require addition of a galactose, a sialic acid, and a fucose in order to exhibit a desired activity. Accordingly, the invention provides methods in which two or more enzymes, e.g., glycosyltransferases, trans-sialidases, or sulfotransferases, are used to obtain high-yield synthesis of a desired oligosaccharide determinant.

In one preferred embodiment, LNFIII was prepared from lactose using the *H. pylori* α-1,3/4-fucosyltranferases from strain 1182 described herein, in combination with *Neisseria gonococcus* β-1,3N-acetylglucosaminyltransferase (lgtA) and *Neisseria gonococcus* β-1,4-galactosyltransferase (lgtB). Those of skill will recognize that other β-1,3N-acetylglucosaminyltransferase and β-1,4-galactosyltransferase enzymes can be used in this embodiment of the invention.

In some cases, a glycoprotein- or glycolipid linked oligosaccharide will include an acceptor substrate for the particular glycosyltransferase of interest upon in vivo biosynthesis of the glycoprotein or glycolipid. Such glycoproteins or glycolipids can be glycosylated using the *H. pylori* fucosyltransferase proteins and methods of the invention without prior modification of the glycosylation pattern of the glycoprotein or glycolipid, respectively. In other cases, however, a glycoprotein or glycolipid of interest will lack a suitable acceptor substrate. In such cases, the methods of the invention can be used to alter the glycosylation pattern of the glycoprotein or glycolipid so that the glycoprotein- or glycolipid-linked oligosaccharides then include an acceptor substrate for the glycosyltransferase-catalyzed attachment of a preselected saccharide unit of interest to form a desired oligosaccharide moiety.

Glycoprotein- or glycolipid linked oligosaccharides optionally can be first "trimmed," either in whole or in part, to expose either an acceptor substrate for the glycosyltransferase or a moiety to which one or more appropriate residues can be added to obtain a suitable acceptor substrate. Enzymes such as glycosyltransferases and endoglycosidases are useful for the attaching and trimming reactions. For example, a glycoprotein that displays "high mannose"-type oligosaccharides can be subjected to trimming by a mannosidase to obtain an acceptor substrate that, upon attachment of one or more preselected saccharide units, forms the desired oligosaccharide determinant.

The methods are also useful for synthesizing a desired oligosaccharide moiety on a protein or lipid that is unglycosylated in its native form. A suitable acceptor substrate for the corresponding glycosyltransferase can be attached to such proteins or lipids prior to glycosylation using the methods of the present invention. See, e.g., U.S. Pat. No. 5,272,066 for methods of obtaining polypeptides having suitable acceptors for glycosylation.

Thus, in some embodiments, the invention provides methods for in vitro sialylation of saccharide groups present on a glycoconjugate that first involves modifying the glycoconjugate to create a suitable acceptor. Examples of preferred methods of multi-enzyme synthesis of desired oligosaccharide moieties are as follows.

Fucosylated and Sialylated Oligosaccharide Moieties

Oligosaccharide determinants that confer a desired biological activity upon a glycoprotein often are sialylated in addition to being fucosylated. Accordingly, the invention provides methods in which a glycoprotein-linked oligosaccharide is sialylated and fucosylated in high yields.

The sialylation can be accomplished using either a trans-sialidase or a sialyltransferase, except where a particular moiety requires an α2,6-linked sialic acid, in which a sialyltransferase is used. Suitable examples of each type of enzyme are described above. These methods involve sialylating an acceptor for a sialyltransferase or a trans-sialidase by contacting the acceptor with the appropriate enzyme in the presence of an appropriate donor substrate. For sialyltransferases, CMP-sialic acid is a preferred donor substrate. Trans-sialidases, however, preferably use a donor substrate that includes a leaving group to which the trans-sialidase cannot add sialic acid.

Acceptor substrates of interest include, for example, Galβ-OR. In some embodiments, the acceptor substrates are contacted with a sialyltransferase in the presence of CMP-sialic acid under conditions in which sialic acid is transferred to the non-reducing end of the acceptor substrate to form the compound NeuAcα2,3Galβ-OR or NeuAcα2,6Galβ-OR. In this formula, R is an amino acid, a saccharide, an oligosaccharide or an aglycon group having at least one carbon atom. R is linked to or is part of a glycoprotein. An α2,8-sialyltransferase can also be used to attach a second or multiple sialic acid residues to the above structures.

To obtain an oligosaccharide moiety that is both sialylated and fucosylated, the sialylated acceptor is contacted with a fucosyltransferase as discussed above. The sialyltransferase and fucosyltransferase reactions are generally conducted sequentially, since most sialyltransferases are not active on a fucosylated acceptor. FT VII, however, acts only on a sialylated acceptor substrate. Therefore, FTVII can be used in a simultaneous reaction with a sialyltransferase.

If the trans-sialidase is used to accomplish the sialylation, the fucosylation and sialylation reactions can be conducted either simultaneously or sequentially, in either order. The protein to be modified is incubated with a reaction mixture that contains a suitable amount of a trans-sialidase, a suitable sialic acid donor substrate, a fucosyltransferase (capable of making an α1,3 or α1,4 linkage), and a suitable fucosyl donor substrate (e.g., GDP-fucose).

Galactosylated, Fucosylated and Sialylated Oligosaccharide Determinants

The invention also provides methods for enzymatically synthesizing oligosaccharide moieties that are galactosylated, fucosylated, and sialylated. Either a sialyltransferase or a trans-sialidase (for α2,3-linked sialic acid only) can be used in these methods.

The trans-sialidase reaction involves incubating the protein to be modified with a reaction mixture that contains a suitable amount of a galactosyltransferase (galβ1,3 or galβ1,4), a suitable galactosyl donor (e.g., UDP-galactose), a trans-sialidase, a suitable sialic acid donor substrate, a fucosyltransferase (capable of making an α1,3 or β1,4 linkage), a suitable fucosyl donor substrate (e.g., GDP-fucose), and a divalent metal ion. These reactions can be carried out either sequentially or simultaneously.

If a sialyltransferase is used, the method involves incubating the protein to be modified with a reaction mixture that contains a suitable amount of a galactosyltransferase (galβ1,3 or galβ1,4), a suitable galactosyl donor (e.g., UDP-galactose), a sialyltransferase (α2,3 or α2,6) and a suitable sialic acid donor substrate (e.g., CMP sialic acid). The reaction is allowed to proceed substantially to completion, and then a fucosyltransferase (capable of making an α1,3 or α1,4 linkage) and a suitable fucosyl donor substrate (e.g., GDP-fucose). If a fucosyltransferase is used that requires a sialylated substrate (e.g., FT VII), the reactions can be conducted simultaneously.

Sialyltransferase Reactions

As discussed above, in some embodiments, the present invention provides a H. pylori fucosyltransferase proteins and methods for fucosylating a glycoprotein following the sialylation of the glycoprotein. In a preferred embodiment, the fusion proteins and methods of the invention synthesize glycoproteins having a substantially uniform sialylation pattern. The sialylated glycoprotein is then fucosylated, thereby producing a population of fucosylated glycoproteins in which the members have a substantially uniform fucosylation pattern.

The glycoprotein can be contacted with a sialyltransferase and a sialic acid donor substrate for a sufficient time and under appropriate reaction conditions to transfer sialic acid from the sialic acid donor substrate to the saccharide groups. Sialyltransferases comprise a family of glycosyltransferases that transfer sialic acid from the donor substrate CMP-sialic acid to acceptor oligosaccharide substrates. In preferred embodiments, the sialyltransferases are recombinant sialyltransferase fusion proteins. Suitable sialyltransferase reactions are described in U.S. Provisional Application No. 60/035,710, filed Jan. 16, 1997 and U.S. nonprovisional application Ser. No. 09/007,741, filed Jan. 15, 1998.

In some embodiments, the saccharide moieties on a glycoprotein having sialylation patterns altered by the H. pylori fucosyltransferase proteins of the present invention have a greater percentage of terminal galactose residues sialylated than the unaltered glycoprotein. Preferably, greater than about 80% of terminal galactose residues present on the glycoprotein-linked oligosaccharides will be sialylated following use of the methods. More preferably, use of the H. pylori fucosyltransferase proteins and methods of the invention will result in greater than about 90% sialylation, and even more preferably greater than about 95% sialylation of terminal galactose residues. Most preferably, essentially 100% of the terminal galactose residues present on the glycoproteins in the composition are sialylated following modification using the methods of the present invention. The fusion proteins and methods of the inventions are typically capable of achieving the desired level of sialylation in about 48 hours or less, and more preferably in about 24 hours or less.

At least 15 different mammalian sialyltransferases have been documented, and the cDNAs of thirteen of these have been cloned to date (for the systematic nomenclature that is used herein, see, Tsuji et al. (1996) *Glycobiology* 6: v-xiv). These cDNAs can be used for making the recombinant sialyltransferase fusion proteins of the invention.

Preferably, for glycosylation of N-linked and/or O-linked carbohydrates of glycoproteins, the sialyltransferase transfer sialic acid to the terminal sequence Galβ1,4-OR or GalNAc-OR, where R is an amino acid, a saccharide, an oligosaccharide or an aglycon group having at least one carbon atom and is linked to or is part of a glycoprotein. Galβ1,4-GlcNAc is the most common penultimate sequence underlying the terminal sialic acid on fully sialylated carbohydrate structures. At least three of the cloned mammalian sialyltransferases meet this acceptor specificity requirement, and each of these have been demonstrated to transfer sialic acid to N-linked and O-linked carbohydrate groups of glycoproteins.

In some embodiments, the invention sialylation methods that have increased commercial practicality through the use of bacterial sialyltransferases, either recombinantly produced or produced in the native bacterial cells. Two bacterial sialyltransferases have been recently reported; an ST6Gal II from *Photobacterium damsela* (Yamamoto et al. (1996) *J. Biochem.* 120: 104-110) and an ST3Gal V from *Neisseria meningitidis* (Gilbert et al. (1996) *J. Biol. Chem.* 271: 28271-28276). The two recently described bacterial enzymes transfer sialic acid to the Galβ1,4GlcNAc sequence on oligosaccharide substrates.

A recently reported viral α2,3-sialyltransferase is also suitable for testing and possible use in the sialylation methods of the invention (Sujino et al. (2000) *Glycobiology* B10: 313-320). This enzyme, v-ST3Gal I, was obtained from Myxoma virus-infected cells and is apparently related to the mammalian ST3Gal IV as indicated by comparison of the respective amino acid sequences. v-ST3Gal I catalyzes the sialylation of Type I (Galβ1,3-GlcNAcβ1-R), Type II (Galβ1,4GlcNAc-β1-R) and III (Gal β1,3GalNAcβ1-R) acceptors. The enzyme can also transfer sialic acid to fucosylated acceptor substrates (e.g., Lewis-x and Lewis-a).

An example of a sialyltransferase that is useful in the claimed methods is ST3Gal III, which is also referred to as α(2,3)sialyltransferase (EC 2.4.99.6). This enzyme catalyzes the transfer of sialic acid to the Gal of a Galβ1, 3GlcNAc, Galβ1,3GalNAc or Galβ1,4GlcNAc glycoside (see, e.g., Wen et al. (1992) *J. Biol. Chem.* 267: 21011; Van den Eijnden et al. (1991) *J. Biol. Chem.* 256: 3159). The sialic acid is linked to a Gal with the formation of an α-linkage between the two saccharides. Bonding (linkage) between the saccharides is between the 2-position of NeuAc and the 3-position of Gal. This particular enzyme can be isolated from rat liver (Weinstein et al. (1982) *J. Biol. Chem.* 257: 13845); the human cDNA (Sasaki et al. (1993) *J. Biol. Chem.* 268: 22782-22787; Kitagawa & Paulson (1994) *J. Biol. Chem.* 269: 1394-1401) and genomic (Kitagawa et al. (1996) *J. Biol. Chem.* 271: 931-938) DNA sequences are known, facilitating production of this enzyme by recombinant expression. In a preferred embodiment, the claimed sialylation methods use a rat ST3Gal III.

Other sialyltransferases, including those listed above, are also useful in an economic and efficient large scale process for sialylation of commercially important glycoproteins. As described above, a simple test to find out the utility of these other enzymes, is to react various amounts of each enzyme (1-100 mU/mg protein) with a readily available glycoprotein protein such as asialo-$\alpha_1$-AGP (at 1-10 mg/ml) to compare the ability of the sialyltransferase of interest to sialylate glycoproteins. The results can be compared to, for example, either or both of an ST6Gal I or an ST3Gal III (e.g., a bovine or human enzyme), depending upon the particular sialic acid linkage that is desired. Alternatively, other glycoproteins or glycoproteins, or N- or O-linked oligosaccharides enzymatically released from the peptide backbone can be used in place of asialo-$\alpha_1$ AGP for this evaluation, or one can use saccharides that are produced by other methods or purified from natural products such as milk. Preferably, however, the sialyltransferases are assayed using an oligosaccharide that is linked to a glycoprotein. Sialyltransferases showing an ability to, for example, sialylate N-linked or O-linked oligosaccharides of glycoproteins more efficiently than ST6Gal I are useful in a practical large scale process for glycoprotein sialylation.

In some embodiments bacterial sialyltransferases are used in to modify an oligosaccharide, a polysaccharide, a glycolipid or a glycoprotein. Examples of bacterial sialyltransferases are found e.g., in U.S. Pat. Nos. 6,503,744; 6,096,529, and 6210933; and U.S. Ser. No. 09/272,960, filed Mar. 18, 1998 and U.S. Ser. No. 09/816,028, filed Mar. 21, 2001; each of which is incorporated herein by reference for all purposes. U.S. Pat. No. 6,503,744 and U.S. Ser. No. 09/816,028, filed Mar. 21, 2001 each contain disclosures of additional glycosyltransferases that can be used in the invention.

The invention also provides methods of altering the sialylation pattern of a glycoprotein prior to fucosylation by adding sialic acid in an α2,6Gal linkage as well as the α2,3Gal linkage, both of which are found on N-linked oligosaccharides of human plasma glycoproteins. In this embodiment, ST3Gal III and ST6Gal I sialyltransferases are both present in the reaction and provide proteins having a reproducible ratio of the two linkages formed in the resialylation reaction. Thus, a mixture of the two enzymes may be of value if both linkages are desired in the final product.

An acceptor substrate for the sialyltransferase is present on the glycoprotein to be modified by the sialylation methods described herein. Suitable acceptors include, for example, galactosylated acceptors such as Galβ1,4GlcNAc, Galβ1,4GalNAc, Galβ1,3GalNAc, Galβ1,3GlcNAc, Galβ1,3Ara, Galβ1,6GlcNAc, Galβ1,4Glc (lactose), GalNAc-O-Ser, GalNAc-O-Thr, and other acceptors known to those of skill in the art (see, e.g., Paulson et al. (1978) *J. Biol. Chem.* 253: 5617-5624). Typically, the acceptors are included in oligosaccharide chains that are attached to asparagine, serine, or threonine residues present in a protein.

EXAMPLES

The following examples are offered to illustrate, but not to limit the claimed invention.

Example 1

Cloning of *Helicobacter pylori* Fucosyltransferases

Putative fucosyltransferase genes from the following strains of *Helicobacter pylori* were PCR amplified, cloned into vectors for expression in *E. coli*: strain 915 FutA, strain 1111 FutA, strain 19C2 FutB, strain 1182 FutB, strain 19C2 FutA, strain 26695 FutA, and strain 1218 FutB. Nucleic acid and amino acid sequences are provided in FIGS. 1-7. An amino acid sequence alignment is provided in FIG. 12; a nucleic acid sequence alignment is provided in FIG. 13.

The putative fucosyltransferase proteins were screened for α1,3/4-fucosyltransferase activity using LNnT and GDP-fucose substrates. The oligostructures of LNnT and one product, LNFPIII are shown in FIG. 14.

One hundred milliliter cultures of *E. coli* transformed with *H. pylori* fucosyltransferase were grown to OD600 of 0.8 and induced with IPTG, and harvested. Cell lysates were made using a french press. The fucosyltransferase enzymes were tested for enzymatic activity and acceptor specificity using the substrate LNnT. The reactions contained 3 mM GDP-fucose, 3 mM LNnT, 50 mM Tris pH 7.5, 20 mM $MnCl_2$, and 15% bacterial lysate. Reactions were incubated at 37° C. for twenty-four hours.

Reaction products were separated using the following TLC-buffer system: 7 IPA:2 $H_2O$:1 Acetic acid. The samples were methylated, hydrolyzed, reduced with sodium borodeuteride, acetylated and analyzed by GC/MS along with samples of LNnT and LNF3. Results are shown in FIG. 15. A Glc vs. Glc-NAc value close to 1 favors fucosylation of Glc-NAc. A Glc vs. Glc-NAc value close to 0 favors fucosylation of Glc. Fucosyltransferases from the following *H. pylori* strains transferred fucose to Glc-NAc: strain 915 FutA, strain 1111 FutA, strain 19C2 FutB, and strain 1182 FutB. The FutA gene product from *H. pylori* strain 19C2A transferred fucose to the reducing glucose of the LNnT acceptor, as did the FutB gene product from *H. pylori* strain 1218 FutB. A novel FutA gene product from *H. pylori* strain 26695 also catalyzed the transfer of fucose to glucose.

Example 2

Production of Oligosaccharides Using *Helicobacter pylori* Fucosyltransferases

One liter cultures of *E. coli* expressing *H. pylori* fucosyltransferases were grown, induce and harvested. The lysates were used to synthesize LNFIII from LNnT. Two different ion exchange resins were tested for purification of LNFIII. Reaction mixtures were centrifuged at 5,000 RPM for thirty minutes. Samples were then processed by ultrafiltration using hollow fiber ultrafiltration membranes with a molecular weight cut off of 10 kD. Ion exchange chromatography was done using either MR3 $NH_4HCO_3$ column 1 ml resin per 1 ml synthesis (70%) or Dowex1/Dowex50 column 2 ml resin per 1 ml synthesis (82%). Samples were then run on a P2 Size Exclusion column and then lyophilized. Results are shown in FIG. 16. Yields using the Dowex resin approached 50%, while yields from the MR3 NH₄HCO₃ column approached 70%.

LNFIII was prepared from lactose using lysates from *E. coli* cells expressing *H. pylori* α-1,3/4-fucosyltranferases from strain 1182 described herein, in combination with *Neisseria gonococcus* β-1,3N-acetylglucosaminyltransferase (lgtA) and *Neisseria gonococcus*, β-1,4-galactosyltransferase (lgtB) on a multigram scale. Those of skill will recognize that other β-1,3N-acetylglucosaminyltransferase and β-1,4-galactosyltransferase enzymes can be used in this embodiment of the invention.

Example 3

Production of Glycoproteins Using *Helicobacter pylori* Fucosyltransferases

The ability of fucosyltransferase from *H. pylori* strain 1182B to add fucose to acceptor molecules on glycoprotein was tested using asialyltransferrin as a substrate. The 1182B fucosyltransferase was produced in *E. coli* cells as described above. The reactions were carried out in a buffer containing 50 mM Tris pH. 7.5, 20 mM MnCl₂, 200 μg asialyltransferrin, and 5 mM GDP-fucose. Reactions were started by adding 15% v/v of the bacterial lysate. The reaction was incubated overnight at 37° C. The samples were analyzed using GC/MS. Results are shown in FIG. 17.

Example 4

Cloning of Additional *Helicobacter pylori* Fucosyltransferases

Putative fucosyltransferase genes from the following strains of *Helicobacter pylori* were PCR amplified, cloned into vectors for expression in *E. coli*: strain 955 FutA, strain 1111 FutB, strain 948 FutA, strain 802 FutA, and strain 1218 FutA. Nucleic acid and amino acid sequences are provided in FIGS. 18-22.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes

What is claimed is:

1. An isolated fucosyltransferase protein comprising a polypeptide that has greater than 90% identity to the full length of SEQ ID NO:16, wherein the fucosyltransferase catalyzes the transfer of a fucose residue from a donor substrate to an acceptor substrate.

2. The isolated fucosyltransferase of claim 1, further comprising an amino acid tag.

3. The isolated fucosyltransferase of claim 1, wherein the polypeptide is SEQ ID NO:16.

4. The isolated fucosyltransferase of claim 1, wherein the fucosyltransferase catalyzes the transfer of fucose to an acceptor molecule selected from an N-acetylglucosamine residue and a glucose residue.

5. The isolated fucosyltransferase protein of claim 1, wherein the polypeptide has greater than 95% identity to the full-length of SEQ ID NO:16.

6. A method for producing a fucosylated glycolipid, the method comprising:
  contacting the isolated fucosyltransferase protein of claim 1 with a mixture comprising a donor substrate comprising a fucose residue, and an acceptor substrate on a glycolipid, under conditions where the fucosyltransferase catalyzes the transfer of the fucose residue from a donor substrate to the acceptor substrate on the glycolipid, thereby producing a fucosylated glycolipid.

7. A method of making a fucosylated oligosaccharide, the method comprising:
  contacting the isolated fucosyltransferase of claim 1 with a mixture comprising a donor substrate comprising a fucose residue, and an acceptor substrate comprising a sugar or oligosaccharide, under conditions where the fusion protein catalyzes the transfer of a fucose residue from the donor substrate to the acceptor substrate, thereby producing a fucosylated oligosaccharide.

8. The method of claim 7, wherein the method further comprises a step of purifying the fucosylated oligosaccharide.

9. The method of claim 7, wherein a donor substrate is GDP-fucose.

10. The method of claim 7, wherein the fucosyltransferase comprises an amino acid tag.

11. The method of claim 7, wherein an acceptor substrate comprises a member selected from N-acetylglucosamine and glucose.

12. The method of claim 7, wherein the acceptor substrate is Lacto-N-neo-Tetraose (LNnT).

13. The method of claim 12, wherein the fucosylated oligosaccharide is Lacto-N-Fucopentaose III (LNFP III).

14. The method of claim 7, wherein the mixture further comprises lactose, a β-1,3-N-acetylglucosaminyltransferase, and a β-1,4-galactosyltransferase.

15. The method of claim 14, wherein the fucosylated oligosaccharide is Lacto-N-Fucopentaose III (LNFP III).

16. The method of claim 14, wherein the β-1,3-N-acetylglucosaminyltransferase is a bacterial enzyme.

17. The method of claim 16, wherein the β-1,3-N-acetylglucosaminyltransferase is from Neisseria gonococcus.

18. The method of claim 14, wherein the β-1,4-galactosyltransferase is a bacterial enzyme.

19. The method of claim 18, wherein the β-1,4-galactosyltransferase is from Neisseria gonococcus.

20. A method for producing a fucosylated glycoprotein, the method comprising:
  contacting a host cell extract comprising a fucosyltransferase protein having greater than 90% identity to the full-length of SEQ ID NO:16, with a mixture comprising a donor substrate comprising a fucose residue, and an acceptor substrate on a glycoprotein, under conditions where the fucosyltransferase catalyzes the transfer of the fucose residue from a donor substrate to the acceptor substrate on the glycoprotein, thereby producing a fucosylated glycoprotein, wherein the host cell extract is heterologous to the fucosyltransferase protein.

21. The method of claim 1, wherein the polypeptide comprises an amino acid sequence having greater than 95% identity to the full-length of SEQ ID NO:16.

22. The method of claim 1, wherein the polypeptide comprises SEQ ID NO:16.

23. The method of claim 1, wherein the polypeptide further comprises an amino acid tag.

24. The method of claim 1, wherein the method further comprises a step of purifying the fucosylated glycoprotein.

25. The method of claim 1, wherein the acceptor substrate is selected from a glucose residue and an N-acetylglucosamine residue.

26. The method of claim 1, wherein an acceptor substrate on the glycoprotein comprises Galb1-OR, Galb,3/4GlcNAc-OR, NeuAca2,3Galb1,3/4GlcNAc-Or, wherein R is an amino acid, a saccharide, an oligosaccharide, or an aglycon group having at least one carbon atom.

* * * * *

SEQUENCE LISTING

```
<160> NUMBER OF SEQ ID NOS: 81

<210> SEQ ID NO 1
<211> LENGTH: 1461
<212> TYPE: DNA
<213> ORGANISM: Helicobacter pylori
<220> FEATURE:
<223> OTHER INFORMATION: H. pylori strain 1182 FutB fucosyltransferase
      (1182B)

<400> SEQUENCE: 1
atgttccaac ccctattaga cgcttatata gaaagcgctt ccattgaaaa aattacctct      60
aaatctcccc cccccctaaa aatcgctgtg gcgaattggt ggggagatga agaggttgaa     120
gaatttaaaa agaacattct ttattttatt ctcagtcagc attacacaat caccctccac     180
caaaacccca acgaaccctc cgatctcgtc tttggcagtc ctattggatc agccagaaaa     240
atcttatcct atcaaaacgc aaaaagagtg ttttacaccg gtgaaaacga atcgcctaat     300
ttcaacctct ttgattacgc cataggcttt gatgaattgg atttagaga tcgttattta     360 agaatgcctt tatattatga tagactacac cataaagccg agagcgtgaa tgacaccact     420
tcgccttaca aactcaaacc tgacagcctt tatgctttaa aaaaccctc ccatcatttt     480 aaagaaaacc accccaattt atgcgcagta gtgaacaatg agagcgatcc tttgaaaaga     540
gggtttgcga gttttgtagc gagcaaccct aacgctccta aaaggaatgc tttctatgac     600
gttttaaatt ctatagagcc agttattggg ggagggagcg tgaaaaacac tttaggctat     660
aacattaaaa acaagagcga gttttaagc caatacaaat tcaatctgtg ttttgaaaac     720
tcacaaggct atggctatgt aactgaaaaa atcattgacg cttactttag ccataccatt     780
cctatttatt gggggagtcc tagcgtggca caagatttta accctaagag ttttgtgaat     840
gtttgtgatt ttaaagattt tgatgaagcg attgatcatg tgcgatactt gcacacgcac     900
ccaaacgctt atttagacat gctttatgaa aacccttaa acacccttga tgggaaagct     960
tacttttacc aaaatttgag ttttaaaaaa atcctagatt tttttaaaac gattttagaa    1020
```

-continued

```
aacgacacga tttatcacga taacccttttt atttttttatc gtgatttgaa tgagccgtta    1080
atatctattg atgatgattt gagggttaat tatgatgatt tgagggttaa ttatgatgat    1140
ttgagggtta attatgatga tttgagggtt aattatgatg atttgagggt taattatgat    1200
gatttgaggg ttaattatga tgatttgagg gttaattatg atgatttgag gttaattat     1260 gatgatttga gggttaatta tgatgatttg agggttaatt atgatgattt gagggttaat    1320
tatgagcggc tcttacaaaa cgcctcgcct ttattagaac tctctcaaaa caccactttt    1380
aaaatctatc gcaaagctta tcaaaaatcc ttacctttgt tgcgtgcggc gagaaagttg    1440
attaaaaaat tgggtttgta a                                              1461
```

<210> SEQ ID NO 2
<211> LENGTH: 486
<212> TYPE: PRT
<213> ORGANISM: Helicobacter pylori
<220> FEATURE:
<223> OTHER INFORMATION: H. pylori strain 1182 FutB fucosyltransferase

<400> SEQUENCE: 2

```
Met Phe Gln Pro Leu Leu Asp Ala Tyr Ile Glu Ser Ala Ser Ile Glu
  1               5                  10                  15

Lys Ile Thr Ser Lys Ser Pro Pro Leu Lys Ile Ala Val Ala Asn
             20                  25                  30

Trp Trp Gly Asp Glu Glu Val Glu Glu Phe Lys Lys Asn Ile Leu Tyr
         35                  40                  45

Phe Ile Leu Ser Gln His Tyr Thr Ile Thr Leu His Gln Asn Pro Asn
     50                  55                  60

Glu Pro Ser Asp Leu Val Phe Gly Ser Pro Ile Gly Ser Ala Arg Lys
 65                  70                  75                  80

Ile Leu Ser Tyr Gln Asn Ala Lys Arg Val Phe Tyr Thr Gly Glu Asn
                 85                  90                  95

Glu Ser Pro Asn Phe Asn Leu Phe Asp Tyr Ala Ile Gly Phe Asp Glu
            100                 105                 110

Leu Asp Phe Arg Asp Arg Tyr Leu Arg Met Pro Leu Tyr Tyr Asp Arg
        115                 120                 125

Leu His His Lys Ala Glu Ser Val Asn Asp Thr Thr Ser Pro Tyr Lys
    130                 135                 140

Leu Lys Pro Asp Ser Leu Tyr Ala Leu Lys Lys Pro Ser His His Phe
145                 150                 155                 160

Lys Glu Asn His Pro Asn Leu Cys Ala Val Val Asn Asn Glu Ser Asp
                165                 170                 175

Pro Leu Lys Arg Gly Phe Ala Ser Phe Val Ala Ser Asn Pro Asn Ala
            180                 185                 190

Pro Lys Arg Asn Ala Phe Tyr Asp Val Leu Asn Ser Ile Glu Pro Val
        195                 200                 205

Ile Gly Gly Gly Ser Val Lys Asn Thr Leu Gly Tyr Asn Ile Lys Asn
    210                 215                 220

Lys Ser Glu Phe Leu Ser Gln Tyr Lys Phe Asn Leu Cys Phe Glu Asn
225                 230                 235                 240

Ser Gln Gly Tyr Gly Tyr Val Thr Glu Lys Ile Ile Asp Ala Tyr Phe
                245                 250                 255

Ser His Thr Ile Pro Ile Tyr Trp Gly Ser Pro Ser Val Ala Gln Asp
            260                 265                 270

Phe Asn Pro Lys Ser Phe Val Asn Val Cys Asp Phe Lys Asp Phe Asp
```

-continued

```
              275                 280                 285
Glu Ala Ile Asp His Val Arg Tyr Leu His Thr His Pro Asn Ala Tyr
        290                 295                 300
Leu Asp Met Leu Tyr Glu Asn Pro Leu Asn Thr Leu Asp Gly Lys Ala
305                 310                 315                 320
Tyr Phe Tyr Gln Asn Leu Ser Phe Lys Lys Ile Leu Asp Phe Phe Lys
                325                 330                 335
Thr Ile Leu Glu Asn Asp Thr Ile Tyr His Asp Asn Pro Phe Ile Phe
            340                 345                 350
Tyr Arg Asp Leu Asn Glu Pro Leu Ile Ser Ile Asp Asp Asp Leu Arg
        355                 360                 365
Val Asn Tyr Asp Asp Leu Arg Val Asn Tyr Asp Asp Leu Arg Val Asn
370                 375                 380
Tyr Asp Asp Leu Arg Val Asn Tyr Asp Asp Leu Arg Val Asn Tyr Asp
385                 390                 395                 400
Asp Leu Arg Val Asn Tyr Asp Asp Leu Arg Val Asn Tyr Asp Asp Leu
                405                 410                 415
Arg Val Asn Tyr Asp Asp Leu Arg Val Asn Tyr Asp Asp Leu Arg Val
            420                 425                 430
Asn Tyr Asp Asp Leu Arg Val Asn Tyr Glu Arg Leu Leu Gln Asn Ala
        435                 440                 445
Ser Pro Leu Leu Glu Leu Ser Gln Asn Thr Thr Phe Lys Ile Tyr Arg
    450                 455                 460
Lys Ala Tyr Gln Lys Ser Leu Pro Leu Leu Arg Ala Ala Arg Lys Leu
465                 470                 475                 480
Ile Lys Lys Leu Gly Leu
                485
```

<210> SEQ ID NO 3
<211> LENGTH: 1299
<212> TYPE: DNA
<213> ORGANISM: Helicobacter pylori
<220> FEATURE:
<223> OTHER INFORMATION: H. pylori strain 1111 FutA fucosyltransferase
      (1111FutA)

<400> SEQUENCE: 3

```
atgttccaac ccctattaga tgcctttata gaaagcgctc cattgaaaaa atggcctcta      60
aatctccccc ccctaaaaat cgctgtggcg aattggtggg gagatgaaga aattaaaaaa     120
tttaaaaaga gcgttcttta ttttatccta agccagcatt acacaatcac tttacaccga     180
aaccctgata aacctgcgga catcgtcttt ggtaaccccc ttggatcagc cagaaaaatc     240
ttatcctatc aaaacgcaaa aagggtgttt tacaccggtg aaaatgaagt ccctaacttc     300
aacctctttg attacgccat aggctttgat gaattggact tagagatcg ttatttgaga     360
atgcctttgt attatgccta tttgcattat aaagccgagc ttgttaatga caccacttcg     420
ccttataaac tccaacctga cagcctttat gctttaaaaa acccctccca tcattttaaa     480
gaaaaccacc ccaatttgtg cgcagtagtg aataatgaga gtgatccttt gaaagagggg     540
tttgcgagct tgtcgcaag caaccctaac gctcctagaa ggaacgcttt ttatgaggct     600
ttaaacgcta ttgagccagt tgctggggga gggagcgtga aaaacacttt aggctataat     660
gtcaaaaaca gagcgagtt tttaagccaa tacaaattca atctgtgttt tgaaaacact     720
caaggctatg gctatgtaac tgaaaagatc attgacgctt atttcagcca taccattcct     780
atttattggg ggagtcccag cgtggcgaaa gattttaacc ctaagagttt tgtgaatgtc     840
```

```
catgatttca acaactttga tgaagcgatt gactatatca gatacttgca cacgcaccca      900
aacgcttatt tagacatgca ctatgaaaac ccttaaaca ctattgatgg aaagcttac       960 ttttaccaaa atttgagttt taaaaaaatc ctagatttt ttaaaacgat tttagaaaac      1020
gacacgatct atcacgataa ccctttcatt ttctatcgtg atttgaatga gccttcagta    1080
tctattgatg gtttgagggt taattatgat gatttgaggg ttaattatga tgatttgagg    1140
gttaattatg atgatttgag ggttaattat gagcgccttt tacaaaacgc ctcgccttta   1200
ttagaactct ctcaaaacac cactttaaa atctatcgca aagcttatca aaatccttg      1260 cctttgttgc gtgccataag gagatgggtt aaaaagtaa                            1299
```

<210> SEQ ID NO 4
<211> LENGTH: 432
<212> TYPE: PRT
<213> ORGANISM: Helicobacter pylori
<220> FEATURE:
<223> OTHER INFORMATION: H. pylori strain 1111 FutA fucosyltransferase

<400> SEQUENCE: 4

```
Met Phe Gln Pro Leu Leu Asp Ala Phe Ile Glu Ser Ala Pro Leu Lys
  1               5                  10                  15

Lys Trp Pro Leu Asn Leu Pro Pro Leu Lys Ile Ala Val Ala Asn Trp
             20                  25                  30

Trp Gly Asp Glu Glu Ile Lys Lys Phe Lys Lys Ser Val Leu Tyr Phe
         35                  40                  45

Ile Leu Ser Gln His Tyr Thr Ile Thr Leu His Arg Asn Pro Asp Lys
     50                  55                  60

Pro Ala Asp Ile Val Phe Gly Asn Pro Leu Gly Ser Ala Arg Lys Ile
 65                  70                  75                  80

Leu Ser Tyr Gln Asn Ala Lys Arg Val Phe Tyr Thr Gly Glu Asn Glu
                 85                  90                  95

Val Pro Asn Phe Asn Leu Phe Asp Tyr Ala Ile Gly Phe Asp Glu Leu
            100                 105                 110

Asp Phe Arg Asp Arg Tyr Leu Arg Met Pro Leu Tyr Tyr Ala Tyr Leu
        115                 120                 125

His Tyr Lys Ala Glu Leu Val Asn Asp Thr Thr Ser Pro Tyr Lys Leu
    130                 135                 140

Gln Pro Asp Ser Leu Tyr Ala Leu Lys Lys Pro Ser His His Phe Lys
145                 150                 155                 160

Glu Asn His Pro Asn Leu Cys Ala Val Val Asn Asn Glu Ser Asp Pro
                165                 170                 175

Leu Lys Arg Gly Phe Ala Ser Phe Val Ala Ser Asn Pro Asn Ala Pro
            180                 185                 190

Arg Arg Asn Ala Phe Tyr Glu Ala Leu Asn Ala Ile Glu Pro Val Ala
        195                 200                 205

Gly Gly Gly Ser Val Lys Asn Thr Leu Gly Tyr Asn Val Lys Asn Lys
    210                 215                 220

Ser Glu Phe Leu Ser Gln Tyr Lys Phe Asn Leu Cys Phe Glu Asn Thr
225                 230                 235                 240

Gln Gly Tyr Gly Tyr Val Thr Glu Lys Ile Ile Asp Ala Tyr Phe Ser
                245                 250                 255

His Thr Ile Pro Ile Tyr Trp Gly Ser Pro Ser Val Ala Lys Asp Phe
            260                 265                 270

Asn Pro Lys Ser Phe Val Asn Val His Asp Phe Asn Asn Phe Asp Glu
```

```
                275                 280                 285
Ala Ile Asp Tyr Ile Arg Tyr Leu His Thr His Pro Asn Ala Tyr Leu
    290                 295                 300

Asp Met His Tyr Glu Asn Pro Leu Asn Thr Ile Asp Gly Lys Ala Tyr
305                 310                 315                 320

Phe Tyr Gln Asn Leu Ser Phe Lys Lys Ile Leu Asp Phe Phe Lys Thr
                325                 330                 335

Ile Leu Glu Asn Asp Thr Ile Tyr His Asp Asn Pro Phe Ile Phe Tyr
            340                 345                 350

Arg Asp Leu Asn Glu Pro Ser Val Ser Ile Asp Gly Leu Arg Val Asn
        355                 360                 365

Tyr Asp Asp Leu Arg Val Asn Tyr Asp Asp Leu Arg Val Asn Tyr Asp
    370                 375                 380

Asp Leu Arg Val Asn Tyr Glu Arg Leu Leu Gln Asn Ala Ser Pro Leu
385                 390                 395                 400

Leu Glu Leu Ser Gln Asn Thr Thr Phe Lys Ile Tyr Arg Lys Ala Tyr
                405                 410                 415

Gln Lys Ser Leu Pro Leu Leu Arg Ala Ile Arg Arg Trp Val Lys Lys
            420                 425                 430

<210> SEQ ID NO 5
<211> LENGTH: 1458
<212> TYPE: DNA
<213> ORGANISM: Helicobacter pylori
<220> FEATURE:
<223> OTHER INFORMATION: H. pylori strain 1218 FutB fucosyltransferase
      (1218B.nuc)

<400> SEQUENCE: 5
atgttccaac ccctattaga cgcttatata gaaagcgctt ccattgaaaa aattacctct      60
aaatctcccc cccccctaaa aatcgctgtg gcgaattggt ggggagatga agaggttgaa    120
gaatttaaaa agaacattct ttattttatt ctcagtcagc attacacaat caccctccac    180
caaaacccca acgaaccctc cgatctcgtc tttggcagtc ctattggatc agccagaaaa    240
atcttatcct atcaaaacgc aaaaagagtg ttttacaccg gtgaaaacga atcgcctaat    300
ttcaacctct tgattacgc ataggctttt gatgaattgg attttagaga tcgttattta    360
agaatgcctt tatattatga tagactacac cataaagccg agagcgtgaa tgacaccact    420
tcgccttaca aactcaaacc tgacagcctt tatgctttaa aaaaccctc ccatcatttt    480 aaagaaaacc accccaattt atgcgcagta gtgaacaatg agagcgatcc tttgaaaaga    540
gggtttgcga gttttgtagc gagcaaccct aacgctccta aaaggaatgc tttctatgac    600
gctttaaatt ctatagagcc agttattggg ggagggagcg tgaaaacac tttaggctat    660 aacattaaaa acaagagcga gttttttaagc caatacaaat tcaatctgtg ttttgaaaac    720
tcacaaggct atggctatgt aactgaaaaa atcattgacg cttactttag ccataccatt    780
cctatttatt gggggagtcc tagcgtggca caagatttta accctaagag ttttgtgaat    840
gtttgtgatt ttaaagattt tgatgaagcg attgatcatg tgcgatactt gcacacgcac    900
ccaaacgctt atttagacat gctttatgaa aaccctttaa acacccttga tgggaaagct    960
tacttttacc aaaatttgag ttttaaaaaa atcctagatt tttttaaaac gatcttagaa   1020
aacgacacga tttatcacga taacccttt tattttttatc gtgatttgaa tgagccgtta   1080
atatctattg atgatttgag ggttaattat gatgatttga ggttaattat gatgattttg   1140 aggggttaatt atgatgattt gagggttaat tatgatgatt tgagggttaa ttatgatgat   1200
```

```
ttgagggtta attatgatga tttgagggtt aattatgatg atttgagggt taattatgat    1260
gatttgaggg ttaattgtga tgatttgagg gttaattatg atgatttgag ggttaattat    1320
gagcggctct tacaaaacgc ctcgccttta ttagaactct ctcaaaacac cacttttaaa    1380
atctatcgca aagcttatca aaatccttaa cctttgttgc gtgcggcgag aaagttgatt    1440
aaaaaattgg gtttgtaa                                                  1458
```

<210> SEQ ID NO 6
<211> LENGTH: 485
<212> TYPE: PRT
<213> ORGANISM: Helicobacter pylori
<220> FEATURE:
<223> OTHER INFORMATION: H. pylori strain 1218 FutB fucosyltransferase

<400> SEQUENCE: 6

```
Met Phe Gln Pro Leu Leu Asp Ala Tyr Ile Glu Ser Ala Ser Ile Glu
  1               5                  10                  15

Lys Ile Thr Ser Lys Ser Pro Pro Leu Lys Ile Ala Val Ala Asn
             20                  25                  30

Trp Trp Gly Asp Glu Glu Val Glu Glu Phe Lys Lys Asn Ile Leu Tyr
         35                  40                  45

Phe Ile Leu Ser Gln His Tyr Thr Ile Thr Leu His Gln Asn Pro Asn
     50                  55                  60

Glu Pro Ser Asp Leu Val Phe Gly Ser Pro Ile Gly Ser Ala Arg Lys
 65                  70                  75                  80

Ile Leu Ser Tyr Gln Asn Ala Lys Arg Val Phe Tyr Thr Gly Glu Asn
                 85                  90                  95

Glu Ser Pro Asn Phe Asn Leu Phe Asp Tyr Ala Ile Gly Phe Asp Glu
            100                 105                 110

Leu Asp Phe Arg Asp Arg Tyr Leu Arg Met Pro Leu Tyr Tyr Asp Arg
        115                 120                 125

Leu His His Lys Ala Glu Ser Val Asn Asp Thr Thr Ser Pro Tyr Lys
    130                 135                 140

Leu Lys Pro Asp Ser Leu Tyr Ala Leu Lys Pro Ser His His Phe
145                 150                 155                 160

Lys Glu Asn His Pro Asn Leu Cys Ala Val Val Asn Asn Glu Ser Asp
                165                 170                 175

Pro Leu Lys Arg Gly Phe Ala Ser Phe Val Ala Ser Asn Pro Asn Ala
            180                 185                 190

Pro Lys Arg Asn Ala Phe Tyr Asp Ala Leu Asn Ser Ile Glu Pro Val
        195                 200                 205

Ile Gly Gly Ser Val Lys Asn Thr Leu Gly Tyr Asn Ile Lys Asn
    210                 215                 220

Lys Ser Glu Phe Leu Ser Gln Tyr Lys Phe Asn Leu Cys Phe Glu Asn
225                 230                 235                 240

Ser Gln Gly Tyr Gly Tyr Val Thr Glu Lys Ile Ile Asp Ala Tyr Phe
                245                 250                 255

Ser His Thr Ile Pro Ile Tyr Trp Gly Ser Pro Ser Val Ala Gln Asp
            260                 265                 270

Phe Asn Pro Lys Ser Phe Val Asn Val Cys Asp Phe Lys Asp Phe Asp
        275                 280                 285

Glu Ala Ile Asp His Val Arg Tyr Leu His Thr His Pro Asn Ala Tyr
    290                 295                 300

Leu Asp Met Leu Tyr Glu Asn Pro Leu Asn Thr Leu Asp Gly Lys Ala
```

-continued

```
                305                 310                 315                 320
Tyr Phe Tyr Gln Asn Leu Ser Phe Lys Lys Ile Leu Asp Phe Phe Lys
                    325                 330                 335

Thr Ile Leu Glu Asn Asp Thr Ile Tyr His Asp Asn Pro Phe Ile Phe
                340                 345                 350

Tyr Arg Asp Leu Asn Glu Pro Leu Ile Ser Ile Asp Asp Leu Arg Val
            355                 360                 365

Asn Tyr Asp Asp Leu Arg Val Asn Tyr Asp Asp Leu Arg Val Asn Tyr
        370                 375                 380

Asp Asp Leu Arg Val Asn Tyr Asp Asp Leu Arg Val Asn Tyr Asp Asp
385                 390                 395                 400

Leu Arg Val Asn Tyr Asp Asp Leu Arg Val Asn Tyr Asp Asp Leu Arg
                405                 410                 415

Val Asn Tyr Asp Asp Leu Arg Val Asn Cys Asp Asp Leu Arg Val Asn
                420                 425                 430

Tyr Asp Asp Leu Arg Val Asn Tyr Glu Arg Leu Leu Gln Asn Ala Ser
            435                 440                 445

Pro Leu Leu Glu Leu Ser Gln Asn Thr Thr Phe Lys Ile Tyr Arg Lys
        450                 455                 460

Ala Tyr Gln Lys Ser Leu Pro Leu Leu Arg Ala Ala Arg Lys Leu Ile
465                 470                 475                 480

Lys Lys Leu Gly Leu
            485

<210> SEQ ID NO 7
<211> LENGTH: 831
<212> TYPE: DNA
<213> ORGANISM: Helicobacter pylori
<220> FEATURE:
<223> OTHER INFORMATION: H. pylori strain 19C2 FutB fucosyltransferase
      (ORF19C2B)

<400> SEQUENCE: 7
atgttccaac ccctattaga cgcttatata gacagcaccc gtttagatga aaccgattat      60
aagcccccat taaatatagc cctagcgaat tggtggcctt tggataaaag agaaagcaaa     120
gggtttagaa aaaaatttat cttacatttc attttaagtc agcattacac aatcgctctc     180
caccgaaacc ctgataaacc tgcggacatc gttttttggta accccttgg atcagccaga      240 aaaatcctat cctatcaaaa cgctaaaagg gtgtttttaca ccggtgaaaa cgaagtccct     300
aatttcaacc tctttgatta cgccataggc tttgatgaat ggactttag agatcgttat      360 ttgagaatgc ctttatatta tgatagacta caccataaag ccgagagcgt gaatgacacc     420
accgcacctt acaagattaa atctgacagc ctttatgctt taaaaaagcc ctcccatcat     480
tttaaagaaa accacccaca tttatgcgcg ctaatcaata tgagatcga tcctttgaaa      540 agagggtttg cgagctttgt cgcaagcaac cctaacgccc ctataaggaa cgctttctat     600
gaggctttaa attctattga gccagttact ggggaggga gcgtgagaaa cactttaggc      660
tataacgtca aaaacaaaaa cgaatttttg agccaataca agttcaatct gtgctttgaa      720
aacactcaag gctatggcta tgttactgaa aaaatcattg acgcttactt cagccacacc     780
attcctattt attgggggg agtccctagc gtggcgaaag atttttaaccc c               831

<210> SEQ ID NO 8
<211> LENGTH: 277
<212> TYPE: PRT
<213> ORGANISM: Helicobacter pylori
```

```
<220> FEATURE:
<223> OTHER INFORMATION: H. pylori strain 19C2 FutB fucosyltransferase

<400> SEQUENCE: 8

Met Phe Gln Pro Leu Leu Asp Ala Tyr Ile Asp Ser Thr Arg Leu Asp
  1               5                  10                  15

Glu Thr Asp Tyr Lys Pro Pro Leu Asn Ile Ala Leu Ala Asn Trp Trp
             20                  25                  30

Pro Leu Asp Lys Arg Glu Ser Lys Gly Phe Arg Lys Lys Phe Ile Leu
         35                  40                  45

His Phe Ile Leu Ser Gln His Tyr Thr Ile Ala Leu His Arg Asn Pro
     50                  55                  60

Asp Lys Pro Ala Asp Ile Val Phe Gly Asn Pro Leu Gly Ser Ala Arg
 65                  70                  75                  80

Lys Ile Leu Ser Tyr Gln Asn Ala Lys Arg Val Phe Tyr Thr Gly Glu
                 85                  90                  95

Asn Glu Val Pro Asn Phe Asn Leu Phe Asp Tyr Ala Ile Gly Phe Asp
            100                 105                 110

Glu Leu Asp Phe Arg Asp Arg Tyr Leu Arg Met Pro Leu Tyr Tyr Asp
        115                 120                 125

Arg Leu His His Lys Ala Glu Ser Val Asn Asp Thr Thr Ala Pro Tyr
    130                 135                 140

Lys Ile Lys Ser Asp Ser Leu Tyr Ala Leu Lys Lys Pro Ser His His
145                 150                 155                 160

Phe Lys Glu Asn His Pro His Leu Cys Ala Leu Ile Asn Asn Glu Ile
                165                 170                 175

Asp Pro Leu Lys Arg Gly Phe Ala Ser Phe Val Ala Ser Asn Pro Asn
            180                 185                 190

Ala Pro Ile Arg Asn Ala Phe Tyr Glu Ala Leu Asn Ser Ile Glu Pro
        195                 200                 205

Val Thr Gly Gly Gly Ser Val Arg Asn Thr Leu Gly Tyr Asn Val Lys
    210                 215                 220

Asn Lys Asn Glu Phe Leu Ser Gln Tyr Lys Phe Asn Leu Cys Phe Glu
225                 230                 235                 240

Asn Thr Gln Gly Tyr Gly Tyr Val Thr Glu Lys Ile Ile Asp Ala Tyr
                245                 250                 255

Phe Ser His Thr Ile Pro Ile Tyr Trp Gly Gly Val Pro Ser Val Ala
            260                 265                 270

Lys Asp Phe Asn Pro
        275

<210> SEQ ID NO 9
<211> LENGTH: 276
<212> TYPE: DNA
<213> ORGANISM: Helicobacter pylori
<220> FEATURE:
<223> OTHER INFORMATION: H. pylori strain 915 FutA fucosyltransferase

<400> SEQUENCE: 9
atggcctcta aatctccccc cctaaaaatc gctgtggcga attggtgggg agatgaagaa      60
attaaaaaat ttaaaagag cgttctttat tttatcctaa gccagcatta cacaatcact     120
ttacaccgaa accctgataa acctgcggac atcgtctttg gtaaccccct tggatcagcc     180
agaaaaatct tatcctatca aaacgcaaaa agggtgtttt acaccggtga aaatgaagtc     240
cctaacttca acctctttga ttacgccata ggcttt                               276
```

<210> SEQ ID NO 10
<211> LENGTH: 92
<212> TYPE: PRT
<213> ORGANISM: Helicobacter pylori
<220> FEATURE:
<223> OTHER INFORMATION: H. pylori strain 915 FutA fucosyltransferase
      (915A.pepneose)

<400> SEQUENCE: 10

Met Ala Ser Lys Ser Pro Pro Leu Lys Ile Ala Val Ala Asn Trp Trp
1               5                   10                  15

Gly Asp Glu Glu Ile Lys Lys Phe Lys Lys Ser Val Leu Tyr Phe Ile
            20                  25                  30

Leu Ser Gln His Tyr Thr Ile Thr Leu His Arg Asn Pro Asp Lys Pro
        35                  40                  45

Ala Asp Ile Val Phe Gly Asn Pro Leu Gly Ser Ala Arg Lys Ile Leu
    50                  55                  60

Ser Tyr Gln Asn Ala Lys Arg Val Phe Tyr Thr Gly Glu Asn Glu Val
65                  70                  75                  80

Pro Asn Phe Asn Leu Phe Asp Tyr Ala Ile Gly Phe
                85                  90

<210> SEQ ID NO 11
<211> LENGTH: 1278
<212> TYPE: DNA
<213> ORGANISM: Helicobacter pylori
<220> FEATURE:
<223> OTHER INFORMATION: H. pylori strain 26695 FutA fucosyltransferase
      (26695A.cod)

<400> SEQUENCE: 11
atgttccaac ccctattaga cgcctttata gaaagcgctt ccattgaaaa aatggcctct      60
aaatctcccc cccccccct aaaaatcgct gtggcgaatt ggtggggaga tgaagaaatt     120 aaagaatttta aaagagcgt tctttatttt atcctaagcc aacgctacgc aatcaccctc     180
caccaaaacc ccaatgaatt ttcagatcta gttttagca atcctcttgg agcggctaga     240 aagatttat cttatcaaaa cactaaacga gtgttttaca ccggtgaaaa cgaatcacct      300
aatttcaacc tctttgatta cgccataggc tttgatgaat ggattttaa tgatcgttat      360 ttgagaatgc ctttgtatta tgcccatttg cactataaag ccgagcttgt taatgacacc     420
actgcgccct acaaactcaa agacaacagc ctttatgctt taaaaaaacc ctctcatcat     480
tttaaagaaa accaccctaa tttgtgcgca gtagtgaatg atgagagcga tcttttaaaa     540
agagggtttg ccagttttgt agcgagcaac gctaacgctc ctatgaggaa cgcttttttat     600 gacgctctaa attccataga gccagttact ggggaggaa gtgtgagaaa cactttaggc     660
tataaggttg aaacaaaag cgagttttta agccaataca agttcaatct ctgttttgaa      720
aactcgcaag gttatggcta tgtaaccgaa aaaatccttg atgcgtattt tagccatacc     780
attcctattt attgggggag tcccagcgtg gcgaaagatt ttaaccctaa agttttgtg      840 aatgtgcatg atttcaacaa ctttgatgaa gcgattgatt atatcaaata cctgcacacg     900
cacccaaacg cttatttaga catgctctat gaaaaccctt taaacaccct tgatgggaaa      960
gcttactttt accaagattt gagttttaaa aaatcctag attttttttaa aacgatttta     1020 gaaaacgata cgatttatca caattctca acatctttca tgtgggagta cgatctgcat     1080
aagccgttag tatccattga tgatttgagg gttaattatg atgatttgag ggttaattat     1140
gaccggcttt tacaaaacgc ttcgccttta ttagaactct ctcaaaacac cacttttaaa     1200
atctatcgca aagcttatca aaaatccttg cctttgttgc gcgcggtgag aaagttggtt    1260
aaaaaattgg gtttgtaa                                                 1278

<210> SEQ ID NO 12
<211> LENGTH: 425
<212> TYPE: PRT
<213> ORGANISM: Helicobacter pylori
<220> FEATURE:
<223> OTHER INFORMATION: H. pylori strain 26695 FutA fucosyltransferase

<400> SEQUENCE: 12

```
Met Phe Gln Pro Leu Leu Asp Ala Phe Ile Glu Ser Ala Ser Ile Glu
 1               5                  10                  15

Lys Met Ala Ser Lys Ser Pro Pro Pro Leu Lys Ile Ala Val Ala
                20                  25                  30

Asn Trp Trp Gly Asp Glu Glu Ile Lys Glu Phe Lys Lys Ser Val Leu
             35                  40                  45

Tyr Phe Ile Leu Ser Gln Arg Tyr Ala Ile Thr Leu His Gln Asn Pro
     50                  55                  60

Asn Glu Phe Ser Asp Leu Val Phe Ser Asn Pro Leu Gly Ala Ala Arg
 65                  70                  75                  80

Lys Ile Leu Ser Tyr Gln Asn Thr Lys Arg Val Phe Tyr Thr Gly Glu
                 85                  90                  95

Asn Glu Ser Pro Asn Phe Asn Leu Phe Asp Tyr Ala Ile Gly Phe Asp
            100                 105                 110

Glu Leu Asp Phe Asn Asp Arg Tyr Leu Arg Met Pro Leu Tyr Tyr Ala
        115                 120                 125

His Leu His Tyr Lys Ala Glu Leu Val Asn Asp Thr Thr Ala Pro Tyr
    130                 135                 140

Lys Leu Lys Asp Asn Ser Leu Tyr Ala Leu Lys Lys Pro Ser His His
145                 150                 155                 160

Phe Lys Glu Asn His Pro Asn Leu Cys Ala Val Val Asn Asp Glu Ser
                165                 170                 175

Asp Leu Leu Lys Arg Gly Phe Ala Ser Phe Val Ala Ser Asn Ala Asn
            180                 185                 190

Ala Pro Met Arg Asn Ala Phe Tyr Asp Ala Leu Asn Ser Ile Glu Pro
        195                 200                 205

Val Thr Gly Gly Gly Ser Val Arg Asn Thr Leu Gly Tyr Lys Val Gly
    210                 215                 220

Asn Lys Ser Glu Phe Leu Ser Gln Tyr Lys Phe Asn Leu Cys Phe Glu
225                 230                 235                 240

Asn Ser Gln Gly Tyr Gly Tyr Val Thr Glu Lys Ile Leu Asp Ala Tyr
                245                 250                 255

Phe Ser His Thr Ile Pro Ile Tyr Trp Gly Ser Pro Ser Val Ala Lys
            260                 265                 270

Asp Phe Asn Pro Lys Ser Phe Val Asn Val His Asp Phe Asn Asn Phe
        275                 280                 285

Asp Glu Ala Ile Asp Tyr Ile Lys Tyr Leu His Thr His Pro Asn Ala
    290                 295                 300

Tyr Leu Asp Met Leu Tyr Glu Asn Pro Leu Asn Thr Leu Asp Gly Lys
305                 310                 315                 320

Ala Tyr Phe Tyr Gln Asp Leu Ser Phe Lys Lys Ile Leu Asp Phe Phe
                325                 330                 335

Lys Thr Ile Leu Glu Asn Asp Thr Ile Tyr His Lys Phe Ser Thr Ser
```

```
                    340             345             350
Phe Met Trp Glu Tyr Asp Leu His Lys Pro Leu Val Ser Ile Asp Asp
                355                 360                 365

Leu Arg Val Asn Tyr Asp Asp Leu Arg Val Asn Tyr Asp Arg Leu Leu
        370                 375                 380

Gln Asn Ala Ser Pro Leu Leu Glu Leu Ser Gln Asn Thr Thr Phe Lys
385                 390                 395                 400

Ile Tyr Arg Lys Ala Tyr Gln Lys Ser Leu Pro Leu Leu Arg Ala Val
                405                 410                 415

Arg Lys Leu Val Lys Lys Leu Gly Leu
                420                 425

<210> SEQ ID NO 13
<211> LENGTH: 45
<212> TYPE: DNA
<213> ORGANISM: Helicobacter pylori
<220> FEATURE:
<223> OTHER INFORMATION: H. pylori strain 19C2 fucosyltransferase
      (19C2FutA.cod)

<400> SEQUENCE: 13
atgttccaac ccttactaga cgcctttata gaaagtgctc caatt              45

<210> SEQ ID NO 14
<211> LENGTH: 15
<212> TYPE: PRT
<213> ORGANISM: Helicobacter pylori
<220> FEATURE:
<223> OTHER INFORMATION: H. pylori strain 19C2 fucosyltransferase
      (19C2A.pep)

<400> SEQUENCE: 14

Met Phe Gln Pro Leu Leu Asp Ala Phe Ile Glu Ser Ala Pro Ile
  1               5                  10                  15

<210> SEQ ID NO 15
<211> LENGTH: 1973
<212> TYPE: DNA
<213> ORGANISM: Helicobacter pylori
<220> FEATURE:
<223> OTHER INFORMATION: H. pylori strain 1111 FutB fucosyltransferase

<400> SEQUENCE: 15
ggatcccgag cgaccaatca ttacagggat ttattgcatt tagatgcggc tttcagtaac    60
acgctgatcg tggaaaataa cgccttaaac ggcttggtta ccgggcatat gatgttttca   120
cattctaaag gcgaaatgct cctcgctttg caacgctcgt tgaatatcag taaagatcgc   180
actttagtcg tgggcgatgg ggcgaatgat ttgagcatgt caaacatgc ccatattaaa   240 atcgctttca cgctaaaga ggttttaaaa cagcacgcca cgcattgcat caatgagcct   300
aatctagccc taatcaagcc tttgatttac aaaaattttt tttgtaaaat ccctttaaa   360 aggatagcca tgttccaacc cctattagac gcttatgtag aaagcgcttc cattgaaaaa   420
atggcctcta atctcccccc cccctaaaa atcgctgtgg cgaattggtg gggagatgaa   480
gaaattaaag aatttaaaaa gagcgttctt tattttatct ttagccaacg ctacacaatc   540
gccctccacc aaaaccccaa tgaattttca gatctagtct ttagcaatcc tcttggatca   600
gctagaaaaa tcttatcgta tcaaaacgct aaaagagtgt tttacaccgg tgaaaatgaa   660
gtccctaact tcaacctctt tgattacgcc ataggctttg atgaattgga ttttagagat   720
cgttatttga ggatgccttt atattatgat aggctacacc ataaagccga gagcgtgaat   780
```

-continued

```
gacaccactt cgccctacaa actcaaagac aacagccttt atactttaaa aaaaccctcc      840
catcaattta agaaaaacca ccctaattta gcgcagtcgt gaatgatgag agcgatcctt      900
tgaaaagagg ggttgtgagc tttgtagcga gcaacgctaa cgctcctatg agaaacgcct      960
tttatgacgc tttaaattct attgagccag ttactggggg agggagcgtg aaaaacactt     1020
taggctataa cgtcaaaaac aagagcgagt ttttaagcca atacaagttc aacctgtgtt     1080
ttgaaaactc acaaggctat ggctatgtaa ccgagaagat ccttgacgct tactttagcc     1140
acaccattcc tatttattgg gggagtccta gcgtggcgaa agattttaac cctaaagagt     1200
ttgtgaatgt ccatgatttc aacaactttg atgaagcgat agattatatc aaatacttgc     1260
acacgcaccc aaacgcttat ttagacatgc tctatgaaaa ccctttaaac gcccttgatg     1320
ggaaagctta cttttaccag gatttgagtt ttaaaaaaat cctagctttt tttaaaacga     1380
ttttagaaaa cgatacgatt tatcacaaat cctcaacatc tttcatgtgg agtgcgatct     1440
cgatgagccg ttagcgtcta ttgatgattt gagggttaat tatgatgatt tgagggttaa     1500
ttatgatgat ttgagggtta attatgatga tttgagggtt aattatgatg atttgagggt     1560
taattatgat gatttgaggg ttaattatag cgccttttgc aaaacgcttc acctttattg     1620
gaattatccc aaaacacctc ttttaaaatc tatcgcaaag cctatcaaag cctatcaaaa     1680
atccttaccc ttattgcgcg ccataaggag atgggttaaa agtaaggtg tcttttaaga      1740 ctggttgaga aattgaagcg ctattttaaa atgcgctaac gcttcttttt tgagcgtggg     1800 gttttttgagc atgtcctcta aagcatgggc gcttaaaaaa tgtttggatt ttaaagacac    1860
gatgcgccca aaggattctt ctttagaaag gtttaaaagg cgtttgggca aaatctcgcc    1920
aaatacgata atgacttttg aagcgctgtt gtctaattgc aggtcggaa ttc            1973
```

<210> SEQ ID NO 16
<211> LENGTH: 446
<212> TYPE: PRT
<213> ORGANISM: Helicobacter pylori
<220> FEATURE:
<223> OTHER INFORMATION: H. pylori strain 1111 FutB fucosyltransferase

<400> SEQUENCE: 16

```
Met Phe Gln Pro Leu Leu Asp Ala Tyr Val Glu Ser Ala Ser Ile Glu
  1               5                  10                  15

Lys Met Ala Ser Lys Ser Pro Pro Leu Lys Ile Ala Val Ala Asn
             20                  25                  30

Trp Trp Gly Asp Glu Glu Ile Lys Glu Phe Lys Lys Ser Val Leu Tyr
         35                  40                  45

Phe Ile Phe Ser Gln Arg Tyr Thr Ile Ala Leu His Gln Asn Pro Asn
     50                  55                  60

Glu Phe Ser Asp Leu Val Phe Ser Asn Pro Leu Gly Ser Ala Arg Lys
 65                  70                  75                  80

Ile Leu Ser Tyr Gln Asn Ala Lys Arg Val Phe Tyr Thr Gly Glu Asn
                 85                  90                  95

Glu Val Pro Asn Phe Asn Leu Phe Asp Tyr Ala Ile Gly Phe Asp Glu
            100                 105                 110

Leu Asp Phe Arg Asp Arg Tyr Leu Arg Met Pro Leu Tyr Tyr Asp Arg
        115                 120                 125

Leu His His Lys Ala Glu Ser Val Asn Asp Thr Thr Ser Pro Tyr Lys
    130                 135                 140

Leu Lys Asp Asn Ser Leu Tyr Thr Leu Lys Lys Pro Ser His Gln Phe
```

```
                145                 150                 155                 160
        Lys Glu Asn His Pro Asn Leu Cys Ala Val Val Asn Asp Glu Ser Asp
                        165                 170                 175

Pro Leu Lys Arg Gly Val Val Ser Phe Val Ala Ser Asn Ala Asn Ala
                    180                 185                 190

Pro Met Arg Asn Ala Phe Tyr Asp Ala Leu Asn Ser Ile Glu Pro Val
                195                 200                 205

Thr Gly Gly Gly Ser Val Lys Asn Thr Leu Gly Tyr Asn Val Lys Asn
                210                 215                 220

Lys Ser Glu Phe Leu Ser Gln Tyr Lys Phe Asn Leu Cys Phe Glu Asn
        225                 230                 235                 240

Ser Gln Gly Tyr Gly Tyr Val Thr Glu Lys Ile Leu Asp Ala Tyr Phe
                        245                 250                 255

Ser His Thr Ile Pro Ile Tyr Trp Gly Ser Pro Ser Val Ala Lys Asp
                        260                 265                 270

Phe Asn Pro Lys Glu Phe Val Asn Val His Asp Phe Asn Asn Phe Asp
                    275                 280                 285

Glu Ala Ile Asp Tyr Ile Lys Tyr Leu His Thr His Pro Asn Ala Tyr
                290                 295                 300

Leu Asp Met Leu Tyr Glu Asn Pro Leu Asn Ala Leu Asp Gly Lys Ala
        305                 310                 315                 320

Tyr Phe Tyr Gln Asp Leu Ser Phe Lys Lys Ile Leu Ala Phe Phe Lys
                        325                 330                 335

Thr Ile Leu Glu Asn Asp Thr Ile Tyr His Lys Ser Thr Ser Phe
                    340                 345                 350

Met Trp Glu Cys Asp Leu Asp Glu Pro Leu Ala Ser Ile Asp Asp Leu
                355                 360                 365

Arg Val Asn Tyr Asp Asp Leu Arg Val Asn Tyr Asp Asp Leu Arg Val
                370                 375                 380

Asn Tyr Asp Asp Leu Arg Val Asn Tyr Asp Asp Leu Arg Val Asn Tyr
        385                 390                 395                 400

Asp Asp Leu Arg Val Asn Tyr Glu Arg Leu Leu Gln Asn Ala Ser Pro
                        405                 410                 415

Leu Leu Glu Leu Ser Gln Asn Thr Ser Phe Lys Ile Tyr Arg Lys Ala
                    420                 425                 430

Tyr Gln Lys Pro Ile Lys Asn Pro Tyr Pro Tyr Cys Ala Pro
                435                 440                 445

<210> SEQ ID NO 17
<211> LENGTH: 1861
<212> TYPE: DNA
<213> ORGANISM: Helicobacter pylori
<220> FEATURE:
<223> OTHER INFORMATION: H. pylori strain 802 FutA fucosyltransferase

<400> SEQUENCE: 17
ggatcccggc gtgaattact acctttctgg cttgcacagc tatgccgcag gcgatccctt        60
gcctatccct acttttcttat acttttttggt agcgataccct tttgctctcg tgattttggc   120
ttatttcaaa cgccatttga gtttgcctaa attggtttaa aggatagcca tgttccagcc      180
cttactagac gcctttatag aaagtgcttc aattaaaaaa atgcctctga gttacccccc      240
cctaaaaatc gctgtggcga attggtgggg aggcgctgaa gaatttaaaa agagcgctat      300
gtatttcatc ctaagccaac gctacacaat caccctccac caaaacccca acgaaccctc      360
cgatctcgtc tttggcagtc ctattggagc agccagaaaa atcctatcct accaaaacac      420
```

```
taaaagagtg ttttacgccg gtgaaaatga agtccctaat ttcaacctct ttgattacgc    480
cataggcttt gatgaattgg attttagaga tcgttatttg agaatgcctt tatattatga    540
tagactacac cataaagccg agagcgtgaa tgacaccacc gcgccttaca agattaaacc    600
tgacagcctt tatactttaa aaaaccctc ccatcatttt aaagaaaaac accccatt     660 atgcgcagta gtgaatgatg agagcgatcc tttgaaaaga gggtttgcga gttttgtcgc    720
aagcaaccct aacgctccta aaaggaacgc cttctatgac gctttaaatt ctattgagcc    780
agttactggg ggagggagcg tgaaaaacac tttaggctat aaagttggaa acaaaaacga    840 gttttttaagc caatacaaat tcaatctgtg ttttgaaaac tctcaaggct atggctatgt    900
aaccgaaaaa atcattgacg cttactttag ccataccatt cctatttatt ggggagtcc    960 tagcgtggcg aaagatttta accctaagag ttttgtgaat gtgcatgatt ttaaaaactt    1020
tgatgaagcg attgattacg tgagatactt gcacacgcac ccaaacgctt atttagacat    1080
gctctatgaa aaccctttaa acaccttga tgggaaagct tacttttacc aagatttgag    1140
ttttaaaaaa atcctagatt tttttaaaac gattttagaa aacgatacga tctatcacaa    1200 taacccttttt gttttctatc gtgatttgaa tgagccgtta gtatctattg atgatttgag    1260
agccgattat aataatttga gagccgatta taataatttg agagccgatt ataataattt    1320
gagagccgat tataataatt tgagagccga ttacgatcgc ctgttacaaa accgttcgcc    1380
tttgttggaa ctctctcaaa acaccacttt taaaatctat cacaaagctt atcacaaatc    1440
cttacctttg ttgcgtgcca taggagatg ggttaaaaaa ttgggtttgt aaaattgggg    1500
gtaatcaaac cccttgcgct atcatcgcag acgccacttt tctaaaacca gcgatattag    1560 ccctaaaac aaaattagta gggtctttaa actctttagc ggtttgagag acattttttat    1620 aaatctcttt catgatgtgg tgtaatttcg catccaccac ttcaaaactc caagggtgca    1680
tgctcgcgtt ttgcgccatt tccaagccgc tcacgctcac ccccccagca ttagccgcct    1740
tgcctatacc ataagaaatc ttagcctgta aaacaattc aatcgcttca ttgcttgagg    1800
gcatgttcgc cccttcagcc acgcatttgc acccattaga aggagggtt ttgcggaatt    1860 c                                                                  1861
```

<210> SEQ ID NO 18
<211> LENGTH: 440
<212> TYPE: PRT
<213> ORGANISM: Helicobacter pylori
<220> FEATURE:
<223> OTHER INFORMATION: H. pylori strain 802 FutA fucosyltransferase

<400> SEQUENCE: 18

```
Met Phe Gln Pro Leu Leu Asp Ala Phe Ile Glu Ser Ala Ser Ile Lys
 1               5                  10                  15

Lys Met Pro Leu Ser Tyr Pro Pro Leu Lys Ile Ala Val Ala Asn Trp
            20                  25                  30

Trp Gly Gly Ala Glu Glu Phe Lys Lys Ser Ala Met Tyr Phe Ile Leu
        35                  40                  45

Ser Gln Arg Tyr Thr Ile Thr Leu His Gln Asn Pro Asn Glu Pro Ser
    50                  55                  60

Asp Leu Val Phe Gly Ser Pro Ile Gly Ala Ala Arg Lys Ile Leu Ser
65                  70                  75                  80

Tyr Gln Asn Thr Lys Arg Val Phe Tyr Ala Gly Glu Asn Glu Val Pro
                85                  90                  95
```

```
Asn Phe Asn Leu Phe Asp Tyr Ala Ile Gly Phe Asp Glu Leu Asp Leu
                100                 105                 110

Arg Asp Arg Tyr Leu Arg Met Pro Leu Tyr Tyr Asp Arg Leu His His
            115                 120                 125

Lys Ala Glu Ser Val Asn Asp Thr Thr Ala Pro Tyr Lys Ile Lys Pro
    130                 135                 140

Asp Ser Leu Tyr Thr Leu Lys Lys Pro Ser His His Phe Lys Glu Lys
145                 150                 155                 160

His Pro His Leu Cys Ala Val Val Asn Asp Glu Ser Asp Pro Leu Lys
                165                 170                 175

Arg Gly Phe Ala Ser Phe Val Ala Ser Asn Pro Asn Ala Pro Lys Arg
            180                 185                 190

Asn Ala Phe Tyr Asp Ala Leu Asn Ser Ile Glu Pro Val Thr Gly Gly
    195                 200                 205

Gly Ser Val Lys Asn Thr Leu Gly Tyr Lys Val Gly Asn Lys Asn Glu
    210                 215                 220

Phe Leu Ser Gln Tyr Lys Phe Asn Leu Cys Phe Glu Asn Ser Gln Gly
225                 230                 235                 240

Tyr Gly Tyr Val Thr Glu Lys Ile Ile Asp Ala Tyr Phe Ser His Thr
                245                 250                 255

Ile Pro Ile Tyr Trp Gly Ser Pro Ser Val Ala Lys Asp Phe Asn Pro
            260                 265                 270

Lys Ser Phe Val Asn Val His Asp Phe Lys Asn Phe Asp Glu Ala Ile
    275                 280                 285

Asp Tyr Val Arg Tyr Leu His Thr His Pro Asn Ala Tyr Leu Asp Met
290                 295                 300

Leu Tyr Glu Asn Pro Leu Asn Thr Leu Asp Gly Lys Ala Tyr Phe Tyr
                305                 310                 315                 320

Gln Asp Leu Ser Phe Lys Lys Ile Leu Asp Phe Phe Lys Thr Ile Leu
            325                 330                 335

Glu Asn Asp Thr Ile Tyr His Asn Asn Pro Phe Val Phe Tyr Arg Asp
    340                 345                 350

Leu Asn Glu Pro Leu Val Ser Ile Asp Asp Leu Arg Ala Asp Tyr Asn
                355                 360                 365

Asn Leu Arg Ala Asp Tyr Asn Asn Leu Arg Ala Asp Tyr Asn Asn Leu
            370                 375                 380

Arg Ala Asp Tyr Asn Asn Leu Arg Ala Asp Tyr Asp Arg Leu Leu Gln
385                 390                 395                 400

Asn Arg Ser Pro Leu Leu Glu Leu Ser Gln Asn Thr Thr Phe Lys Ile
                405                 410                 415

Tyr His Lys Ala Tyr His Lys Ser Leu Pro Leu Leu Arg Ala Ile Arg
            420                 425                 430

Arg Trp Val Lys Lys Leu Gly Leu
        435                 440

<210> SEQ ID NO 19
<211> LENGTH: 1664
<212> TYPE: DNA
<213> ORGANISM: Helicobacter pylori
<220> FEATURE:
<223> OTHER INFORMATION: H. pylori strain 948 FutA fucosyltransferase

<400> SEQUENCE: 19
ggatcccggc gtgaattact acctttctgg cttgcacagc tatgccgcag gcgatccctt    60
gcccatcccc actttcttat actttttaat agcgatacct tttgctctcg tgatcttggc   120
```

-continued

```
gtatttcaaa cgccatttga gtttgcctaa attggtttaa aggataaaaa tgttccagcc      180
cttactagac gctttcatag acagcaccca tttagatgaa acaacccata agccccatt      240 aaatgtagcc ctagccaatt ggtggccctt aaaaaatagc gaaaaaaaag gattcagaga      300
cttcattttg catttcatcc taaaacaacg ctataaaatc attctgcaca gcaaccctaa      360
tgaaccctca gatctagtct ttggcaatcc tttggaacaa gccagaaaaa tcttatctta      420
tcaaaacact aaacgagtgt tttacaccgg cgaaaatgaa gtgcctaatt caatctctt      480 tgattacgcc ataggctttg atgaattgga ttttaacgat cgctatttga gaatgccttt      540
gtattacgcc tatttgcatt ataaagccat gcttgttaat gacaccactt cgccctataa      600
actcaaagcc ctttatactt taaaaaaacc ttcccataaa tttaaagaaa ccaccccaa      660 tttatgtgcg ctaatccata acgagagcga tccttggaaa agagggtttg ccagttttgt      720
cgcaagcaat cctaacgctc ccatcagaaa cgctttctat gacgctttaa atgctattga      780
gccagtggct agtggaggga gtgtgaaaaa cactctaggc tataaggtca aaacaaaaa      840 cgaattttta agccaataca agttcaacct ctgttttgaa aactcacaag gctatggcta      900
tgtaaccgaa aaaatccttg atgcgtattt cagccacact atccctattt attgggggag      960
tcccagcgtg gcgaaagatt ttaacccaa agtttgtg aatgtgcatg atttcaacaa     1020
ctttgatgaa gcgattgatt atatcagata tttacacgcg caccaaaacg cttatttaga     1080
catgctttat gaaaacccct taaacaccat tgatgggaaa gcgggttttt accaagattt     1140
gagttttgaa aagatcttag atttttttcaa aaacattctt gaaaacgata cgatttatca     1200
ttgcaatgat gcccattatt ctgctcttca tcgtgatttg aatgagccgt tagtgtctgt     1260
tgatgatttg agaagagatc atgatgattt gagggttaat tatgatgatt tgagagttaa     1320
ttatgatgat ttgagagtta attatgatga tttgagagtt aattatgatg atttgagagt     1380
taattatgat gatttgagaa gagatcatga tgatttgaga agagatcatg aacgcctctt     1440
atcaaaggct accccttat tggagctatc ccaaaacacc tcttttaaaa tctatcgcaa     1500
agcttatcaa aagtccttac ccttgttgcg tgccataaaa acaattcaat cgcttcattg     1560
cttgagggca tgttcgcccc ttcagccacg catttgcacc cattagaaag gagggttttg     1620
cggaattcct gcagcccggg ggatccccg ggctgcagga attc                     1664
```

<210> SEQ ID NO 20
<211> LENGTH: 456
<212> TYPE: PRT
<213> ORGANISM: Helicobacter pylori
<220> FEATURE:
<223> OTHER INFORMATION: H. pylori strain 948 FutA fucosyltransferase

<400> SEQUENCE: 20

```
Met Phe Gln Pro Leu Leu Asp Ala Phe Ile Asp Ser Thr His Leu Asp
  1               5                  10                  15

Glu Thr Thr His Lys Pro Pro Leu Asn Val Ala Leu Ala Asn Trp Trp
                 20                  25                  30

Pro Leu Lys Asn Ser Glu Lys Lys Gly Phe Arg Asp Phe Ile Leu His
             35                  40                  45

Phe Ile Leu Lys Gln Arg Tyr Lys Ile Ile Leu His Ser Asn Pro Asn
         50                  55                  60

Glu Pro Ser Asp Leu Val Phe Gly Asn Pro Leu Glu Gln Ala Arg Lys
 65                  70                  75                  80

Ile Leu Ser Tyr Gln Asn Thr Lys Arg Val Phe Tyr Thr Gly Glu Asn
```

```
                    85                  90                  95
Glu Val Pro Asn Phe Asn Leu Phe Asp Tyr Ala Ile Gly Phe Asp Glu
                100                 105                 110

Leu Asp Phe Asn Asp Arg Tyr Leu Arg Met Pro Leu Tyr Tyr Ala Tyr
            115                 120                 125

Leu His Tyr Lys Ala Met Leu Val Asn Asp Thr Thr Ser Pro Tyr Lys
        130                 135                 140

Leu Lys Ala Leu Tyr Thr Leu Lys Lys Pro Ser His Lys Phe Lys Glu
145                 150                 155                 160

Asn His Pro Asn Leu Cys Ala Leu Ile His Asn Glu Ser Asp Pro Trp
                165                 170                 175

Lys Arg Gly Phe Ala Ser Phe Val Ala Ser Asn Pro Asn Ala Pro Ile
            180                 185                 190

Arg Asn Ala Phe Tyr Asp Ala Leu Asn Ala Ile Glu Pro Val Ala Ser
        195                 200                 205

Gly Gly Ser Val Lys Asn Thr Leu Gly Tyr Lys Val Lys Asn Lys Asn
210                 215                 220

Glu Phe Leu Ser Gln Tyr Lys Phe Asn Leu Cys Phe Glu Asn Ser Gln
225                 230                 235                 240

Gly Tyr Gly Tyr Val Thr Glu Lys Ile Leu Asp Ala Tyr Phe Ser His
                245                 250                 255

Thr Ile Pro Ile Tyr Trp Gly Ser Pro Ser Val Ala Lys Asp Phe Asn
            260                 265                 270

Pro Lys Ser Phe Val Asn Val His Asp Phe Asn Phe Asp Glu Ala
        275                 280                 285

Ile Asp Tyr Ile Arg Tyr Leu His Ala His Gln Asn Ala Tyr Leu Asp
290                 295                 300

Met Leu Tyr Glu Asn Pro Leu Asn Thr Ile Asp Gly Lys Ala Gly Phe
305                 310                 315                 320

Tyr Gln Asp Leu Ser Phe Glu Lys Ile Leu Asp Phe Phe Lys Asn Ile
                325                 330                 335

Leu Glu Asn Asp Thr Ile Tyr His Cys Asn Asp Ala His Tyr Ser Ala
            340                 345                 350

Leu His Arg Asp Leu Asn Glu Pro Leu Val Ser Val Asp Asp Leu Arg
        355                 360                 365

Arg Asp His Asp Asp Leu Arg Val Asn Tyr Asp Asp Leu Arg Val Asn
370                 375                 380

Tyr Asp Asp Leu Arg Val Asn Tyr Asp Asp Leu Arg Val Asn Tyr Asp
385                 390                 395                 400

Asp Leu Arg Val Asn Tyr Asp Asp Leu Arg Arg Asp His Asp Asp Leu
                405                 410                 415

Arg Arg Asp His Glu Arg Leu Leu Ser Lys Ala Thr Pro Leu Leu Glu
            420                 425                 430

Leu Ser Gln Asn Thr Ser Phe Lys Ile Tyr Arg Lys Ala Tyr Gln Lys
        435                 440                 445

Ser Leu Pro Leu Leu Arg Ala Ile
450                 455

<210> SEQ ID NO 21
<211> LENGTH: 1895
<212> TYPE: DNA
<213> ORGANISM: Helicobacter pylori
<220> FEATURE:
<223> OTHER INFORMATION: H. pylori strain 955 FutA fucosyltransferase
```

<400> SEQUENCE: 21

```
ggatcccgag cgaccaatca ttacagggat ttattaaatt tagatgtggc tttcagtaac     60
acgctgatag tggaaaatgg tgccttaaac ggcttggtta cggggcatat gatgttttca    120
cactctaaag gcgaaatgct tctcgcccta caacgcttgc taaatatcag tgaaacgagc    180
actttagttg tgggcgatgg agcgaatgac ttgagcatgt tcaaacatgc ccatattaaa    240
atcgctttca acgctaaaga ggttttaaaa caacacgcca cgcattgcat caatgagcct    300
gatttagccc taatcaagcc tttgatttaa aaaatttttt ttgtaaaata ctcctttaaa    360
ggataaagat gttccagccc ctattagatg ccttcataga aagcgcttca attaaaaaaa    420
aattgcctct aaatctcccc cccctaaaa atcgctgtgg cgaattggtt aacggcact    480
aaagaattta agcgagcgt tctttatttc atcctaaaac aacgctataa atcattctg    540
cacagcaacc ctaatgaacc ctcagatcta gtctttggca atcctttgga acaagccaga    600
aaaatcttat cttatcaaaa cactaaacga gtgttttaca ccggcgaaaa tgaagtgcct    660
aatttcaatc tctttgatta cgccataggc tttgatgaat tggattttaa cgatcgctat    720
ttgagaatgc ctttgtatta cgcctatttg cattataaag ccatgcttgt taatgacacc    780
acttcgccct ataaactcaa agccctttat actttaaaaa aaccttccca taaatttaaa    840
gaaaaccacc ccaatttatg tgcgctaatc cataacgaga gcgatccttg aaaagaggg    900
tttgccagtt ttgtcgcaag caatcctaac gctcccatca gaaacgcttt ctatgacgct    960
ttaaatgcta ttgagccagt ggctagtgga gggagtgtga aaaacactct aggctataag   1020
gtcaaaaaca aaaacgaatt tttaagccaa tacaagttca acctctgttt tgaaaactca   1080
caaggctatg gctatgtaac cgaaaaaatt ccttgatgcg tatttcagcc acactatccc   1140
tatttattgg gggagtccca gcgtggcgaa agatttttaac cctaaaagtt ttgtgaatgt   1200
gcatgatttc aacaactttg atgaagcgat tgattatatc agatatttac acgcgcacca   1260
aaacgcttat ttagacatgc tttatgaaaa ccccttaaac accattgatg ggaaagcggg   1320
tttttaccaa gatttgagtt ttgaaaagat cttagatttt ttcaaaaaca ttcttgaaaa   1380
cgatacgatt tatcattgca atgatgccca ttattctgct cttcatcgtg atttgaatga   1440
gccgttagtg tctgttgatg atttgagaag agatcatgat gatttgaggg ttaattatga   1500
tgatttgaga agagatcatg aacgcctctt atcaaaggct accctctttt tggagctatc   1560
ccaaaacacc tcttttaaaa tctatcgcaa agcttatcaa aagtcctac ccttgttgcg   1620
tgccataagg aagtgggtta aaaataagg cgtattttaa gactgatgaa gaaattgaag   1680
cgctatttta aaatgcgcta acgcttcttt tttgagcgtg gggttttttga gcatgtcctc   1740
taaagcatgg gtgcttaaaa aatgtttttgt tttaaagac acgatgcgtc caaaggattc   1800
ttctttagaa aggtttaaaa ggcgtttggg caaaatctcg ccaaatacca caatgacttt   1860
tgaagcgctg ttgtctaatt gccaggtcgg aattc                             1895
```

<210> SEQ ID NO 22
<211> LENGTH: 49
<212> TYPE: PRT
<213> ORGANISM: Artificial Sequence
<220> FEATURE:
<223> OTHER INFORMATION: Description of Artificial Sequence:H. pylori strain 955 FutA fucosyltransferase coding sequence amino acid translation peptide

<400> SEQUENCE: 22

Met Phe Lys His Ala His Ile Lys Ile Ala Phe Asn Ala Lys Glu Val

```
                1               5                  10                 15
Leu Lys Gln His Ala Thr His Cys Ile Asn Glu Pro Asp Leu Ala Leu
                    20                  25                  30

Ile Lys Pro Leu Ile Phe Lys Ile Phe Phe Val Lys Tyr Ser Phe Lys
        35                  40                  45

Gly
```

```
<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence:H. pylori
      strain 955 FutA fucosyltransferase coding sequence amino acid
      translation peptide

<400> SEQUENCE: 23

Arg Cys Ser Ser Pro Tyr
  1               5
```

```
<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence:H. pylori
      strain 955 FutA fucosyltransferase coding sequence amino acid
      translation peptide

<400> SEQUENCE: 24

Lys Ala Leu Gln Leu Lys Lys Asn Cys Leu
  1               5                  10
```

```
<210> SEQ ID NO 25
<211> LENGTH: 227
<212> TYPE: PRT
<213> ORGANISM: Artificial Sequence
<220> FEATURE:
<223> OTHER INFORMATION: Description of Artificial Sequence:H. pylori
      strain 955 FutA fucosyltransferase coding sequence amino acid
      translation peptide

<400> SEQUENCE: 25

Ile Ser Pro Pro Leu Lys Ile Ala Val Ala Asn Trp Phe Asn Gly Thr
  1               5                  10                  15

Lys Glu Phe Lys Ala Ser Val Leu Tyr Phe Ile Leu Lys Gln Arg Tyr
                    20                  25                  30

Lys Ile Ile Leu His Ser Asn Pro Asn Glu Pro Ser Asp Leu Val Phe
        35                  40                  45

Gly Asn Pro Leu Glu Gln Ala Arg Lys Ile Leu Ser Tyr Gln Asn Thr
     50                  55                  60

Lys Arg Val Phe Tyr Thr Gly Glu Asn Glu Val Pro Asn Phe Asn Leu
 65                  70                  75                  80

Phe Asp Tyr Ala Ile Gly Phe Asp Glu Leu Asp Phe Asn Asp Arg Tyr
                    85                  90                  95

Leu Arg Met Pro Leu Tyr Tyr Ala Tyr Leu His Tyr Lys Ala Met Leu
                100                 105                 110

Val Asn Asp Thr Thr Ser Pro Tyr Lys Leu Lys Ala Leu Tyr Thr Leu
            115                 120                 125

Lys Lys Pro Ser His Lys Phe Lys Glu Asn His Pro Asn Leu Cys Ala
        130                 135                 140
```

-continued

```
Leu Ile His Asn Glu Ser Asp Pro Trp Lys Arg Gly Phe Ala Ser Phe
145                 150                 155                 160

Val Ala Ser Asn Pro Asn Ala Pro Ile Arg Asn Ala Phe Tyr Asp Ala
                165                 170                 175

Leu Asn Ala Ile Glu Pro Val Ala Ser Gly Gly Ser Val Lys Asn Thr
            180                 185                 190

Leu Gly Tyr Lys Val Lys Asn Lys Asn Glu Phe Leu Ser Gln Tyr Lys
        195                 200                 205

Phe Asn Leu Cys Phe Glu Asn Ser Gln Gly Tyr Gly Tyr Val Thr Glu
    210                 215                 220

Lys Ile Pro
225

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence:H. pylori
      strain 955 FutA fucosyltransferase coding sequence amino acid
      translation peptide

<400> SEQUENCE: 26

Cys Val Phe Gln Pro His Tyr Pro Tyr Leu Leu Gly Glu Ser Gln Arg
1               5                   10                  15

Gly Glu Arg Phe
            20

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence:H. pylori
      strain 955 FutA fucosyltransferase coding sequence amino acid
      translation peptide

<400> SEQUENCE: 27

Lys Phe Cys Glu Cys Ala
1               5

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence:H. pylori
      strain 955 FutA fucosyltransferase coding sequence amino acid
      translation peptide

<400> SEQUENCE: 28

Phe Gln Gln Leu
1

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence:H. pylori
      strain 955 FutA fucosyltransferase coding sequence amino acid
      translation peptide

<400> SEQUENCE: 29

Leu Tyr Gln Ile Phe Thr Arg Ala Pro Lys Arg Leu Phe Arg His Ala
```

-continued

```
                1               5              10              15
Leu
```

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence:H. pylori
      strain 955 FutA fucosyltransferase coding sequence amino acid
      translation peptide

<400> SEQUENCE: 30

```
Lys Pro Leu Lys His His
 1               5
```

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence:H. pylori
      strain 955 FutA fucosyltransferase coding sequence amino acid
      translation peptide

<400> SEQUENCE: 31

```
Trp Glu Ser Gly Phe Leu Pro Arg Phe Glu Phe
 1               5                  10
```

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence:H. pylori
      strain 955 FutA fucosyltransferase coding sequence amino acid
      translation peptide

<400> SEQUENCE: 32

```
Lys Asp Leu Arg Phe Phe Gln Lys His Ser
 1               5                  10
```

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence:H. pylori
      strain 955 FutA fucosyltransferase coding sequence amino acid
      translation peptide

<400> SEQUENCE: 33

```
Lys Arg Tyr Asp Leu Ser Leu Gln
 1               5
```

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence:H. pylori
      strain 955 FutA fucosyltransferase coding sequence amino acid
      translation peptide

<400> SEQUENCE: 34

```
Cys Pro Leu Phe Cys Ser Ser Ser
 1               5
```

```
<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence:H. pylori
      strain 955 FutA fucosyltransferase coding sequence amino acid
      translation peptide

<400> SEQUENCE: 35

Ala Val Ser Val Cys
 1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence:H. pylori
      strain 955 FutA fucosyltransferase coding sequence amino acid
      translation peptide

<400> SEQUENCE: 36

Phe Glu Lys Arg Ser
 1               5

<210> SEQ ID NO 37
<211> LENGTH: 18
<212> TYPE: PRT
<213> ORGANISM: Artificial Sequence
<220> FEATURE:
<223> OTHER INFORMATION: Description of Artificial Sequence:H. pylori
      strain 955 FutA fucosyltransferase coding sequence amino acid
      translation peptide

<400> SEQUENCE: 37

Thr Pro Leu Ile Lys Gly Tyr Pro Ser Phe Gly Ala Ile Pro Lys His
 1               5                  10                  15

Leu Phe

<210> SEQ ID NO 38
<211> LENGTH: 20
<212> TYPE: PRT
<213> ORGANISM: Artificial Sequence
<220> FEATURE:
<223> OTHER INFORMATION: Description of Artificial Sequence:H. pylori
      strain 955 FutA fucosyltransferase coding sequence amino acid
      translation peptide

<400> SEQUENCE: 38

Asn Leu Ser Gln Ser Leu Ser Lys Val Leu Thr Leu Val Ala Cys His
 1               5                  10                  15

Lys Glu Val Gly
             20

<210> SEQ ID NO 39
<211> LENGTH: 19
<212> TYPE: PRT
<213> ORGANISM: Artificial Sequence
<220> FEATURE:
<223> OTHER INFORMATION: Description of Artificial Sequence:H. pylori
      strain 955 FutA fucosyltransferase coding sequence amino acid
      translation peptide

<400> SEQUENCE: 39

Lys Ile Arg Arg Ile Leu Arg Leu Met Lys Lys Leu Lys Arg Tyr Phe
 1               5                  10                  15
```

```
Lys Met Arg

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence:H. pylori
      strain 955 FutA fucosyltransferase coding sequence amino acid
      translation peptide

<400> SEQUENCE: 40

Arg Phe Phe Phe Glu Arg Gly Val Phe Glu His Val Leu
 1               5                  10

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence:H. pylori
      strain 955 FutA fucosyltransferase coding sequence amino acid
      translation peptide

<400> SEQUENCE: 41

Ser Met Gly Ala
 1

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence:H. pylori
      strain 955 FutA fucosyltransferase coding sequence amino acid
      translation peptide

<400> SEQUENCE: 42

Lys Met Phe Cys Phe
 1               5

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence:H. pylori
      strain 955 FutA fucosyltransferase coding sequence amino acid
      translation peptide

<400> SEQUENCE: 43

Arg His Asp Ala Ser Lys Gly Phe Phe Phe Arg Lys Val
 1               5                  10

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence:H. pylori
      strain 955 FutA fucosyltransferase coding sequence amino acid
      translation peptide

<400> SEQUENCE: 44

Lys Ala Phe Gly Gln Asn Leu Ala Lys Tyr His Asn Asp Phe
 1               5                  10
```

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence:H. pylori
strain 955 FutA fucosyltransferase coding sequence amino acid
translation peptide

<400> SEQUENCE: 45

Ser Ala Val Val
 1

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence:H. pylori
strain 955 FutA fucosyltransferase coding sequence amino acid
translation peptide

<400> SEQUENCE: 46

Leu Pro Gly Arg Asn
 1               5

<210> SEQ ID NO 47
<211> LENGTH: 1742
<212> TYPE: DNA
<213> ORGANISM: Helicobacter pylori
<220> FEATURE:
<223> OTHER INFORMATION: H. pylori strain 1218 FutA fucosyltransferase

<400> SEQUENCE: 47

| | | | | | |
|---|---|---|---|---|---|
| ggatcctctg | gcttgcacag | ctatgccgca | ggcgatccct | tgcctatccc | tactttctta | 60 |
| taccttttg | gtagcgatac | ctttcgctct | cgtgatcttg | gcttatttca | aacgccattt | 120 |
| gagtttgcct | aaattggttt | aaaggataac | catgttccaa | cccctattag | acgcttatat | 180 |
| agaaagcgct | tccattgaaa | aaattacctc | taaatctccc | ccccccctaa | aaatcgctgt | 240 |
| ggcgaattgg | tggggagatg | aagaggttga | agaatttaaa | agaacattc | tttattttat | 300 |
| tctcagtcag | cattacacaa | tcaccctcca | ccaaaacccc | aacgaaccct | ccgatctcgt | 360 |
| ctttggcagt | cctattggat | cagccagaaa | atcttatcc | tatcaaaacg | caaaagagt | 420 |
| gttttacacc | ggtgaaaacg | aatcgcctaa | tttcaacctc | tttgattacg | ccataggctt | 480 |
| tgatgaatgg | attttagaga | tcgttattta | agaatgcctt | tatattatga | tagactacac | 540 |
| cataaagccg | agagcgtgaa | tgacaccact | tcgccttaca | aactcaaacc | tgacagcctt | 600 |
| tatgctttaa | aaaaccctc | ccatcatttt | aaagaaaacc | accccaattt | atgcgcagta | 660 |
| gtgaacaatg | agagcgatcc | tttgaaaaga | gggtttgcga | gttttgtagc | gagcaaccct | 720 |
| aacgctccta | aaaggaatgc | tttctatgac | gctttaaatt | ctatagagcc | agttattggg | 780 |
| ggagggagcg | tgaaaaacac | tttaggctat | aacattaaaa | acaagagcga | gtttttaagc | 840 |
| caatacaaat | tcaatctgtg | ttttgaaaac | tcacaaggct | atggctatgt | aactgaaaaa | 900 |
| atcattgacg | cttactttag | ccataccatt | cctatttatt | gggggagtcc | tagcgtggca | 960 |
| caagatttta | accctaagag | ttttgtgaat | gtttgtgatt | ttaaagattt | tgatgaagcg | 1020 |
| attgatcatg | tgcgatactt | gcacacgcac | ccaaacgctt | atttagacat | gctttatgaa | 1080 |
| aacccttttaa | acaccttga | tgggaaagct | tactttccaa | aatttgagtt | ttaaaaaaat | 1140 |
| cctagatttt | tttaaaacga | tcttagaaaa | cgacacgatt | tatcacgata | acccttttat | 1200 |

```
ttttatcgt gatttgaatg agccgttaat atctattgat gatttgaggg ttaattatga    1260
tgatttgagg gttaattatg atgatttgag ggttaattat gatgatttga gggttaatta    1320
tgatgatttg agggttaatt atgatgattt gagggttaat tatgatgatt tgagggttaa    1380
ttatgatgat ttgagggtta attatgatga tttgagggtt aattgtgatg atttgagggt    1440
taattatgat gatttgaggg ttaattatga gcggctctta caaaacgcct cgcctttatt    1500
agaactctct caaaacacca cttttaaaat ctatcgcaaa gcttatcaaa aatccttacc    1560
tttgttgcgt gcggcgagaa agttgattaa aaaattgggt ttgtaaaatt ggggtaatc     1620 aaacccttg cgctatcatc gcagacgcca cctttctaaa accagcgata ttagccccta     1680
aaacaaaatt agtagggtct ttaaactctt tagcggtttg agagacattc ttataagaat    1740
tc                                                                   1742
```

<210> SEQ ID NO 48
<211> LENGTH: 119
<212> TYPE: PRT
<213> ORGANISM: Artificial Sequence
<220> FEATURE:
<223> OTHER INFORMATION: Description of Artificial Sequence:H. pylori
      strain 1218 FutA fucosyltransferase coding sequence amino acid
      translation peptide

<400> SEQUENCE: 48

Met Phe Gln Pro Leu Leu Asp Ala Tyr Ile Glu Ser Ala Ser Ile Glu
1               5                   10                  15

Lys Ile Thr Ser Lys Ser Pro Pro Leu Lys Ile Ala Val Ala Asn
            20                  25                  30

Trp Trp Gly Asp Glu Glu Val Glu Glu Phe Lys Lys Asn Ile Leu Tyr
        35                  40                  45

Phe Ile Leu Ser Gln His Tyr Thr Ile Thr Leu His Gln Asn Pro Asn
    50                  55                  60

Glu Pro Ser Asp Leu Val Phe Gly Ser Pro Ile Gly Ser Ala Arg Lys
65                  70                  75                  80

Ile Leu Ser Tyr Gln Asn Ala Lys Arg Val Phe Tyr Thr Gly Glu Asn
                85                  90                  95

Glu Ser Pro Asn Phe Asn Leu Phe Asp Tyr Ala Ile Gly Phe Asp Glu
            100                 105                 110

Trp Ile Leu Glu Ile Val Ile
        115

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence:H. pylori
      strain 1218 FutA fucosyltransferase coding sequence amino acid
      translation peptide

<400> SEQUENCE: 49

Glu Cys Leu Tyr Ile Met Ile Asp Tyr Thr Ile Lys Pro Arg Ala
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Description of Artificial Sequence:H. pylori
      strain 1218 FutA fucosyltransferase coding sequence amino acid

```
                                      translation peptide

<400> SEQUENCE: 50

Met Thr Pro Leu Arg Leu Thr Asn Ser Asn Leu Thr Ala Phe Met Leu
 1               5                  10                  15

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence:H. pylori
      strain 1218 FutA fucosyltransferase coding sequence amino acid
      translation peptide

<400> SEQUENCE: 51

Lys Asn Pro Pro Ile Ile Leu Lys Lys Thr Thr Pro Ile Tyr Ala Gln
 1               5                  10                  15

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence:H. pylori
      strain 1218 FutA fucosyltransferase coding sequence amino acid
      translation peptide

<400> SEQUENCE: 52

Thr Met Arg Ala Ile Leu
 1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence:H. pylori
      strain 1218 FutA fucosyltransferase coding sequence amino acid
      translation peptide

<400> SEQUENCE: 53

Lys Glu Gly Leu Arg Val Leu
 1               5

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence:H. pylori
      strain 1218 FutA fucosyltransferase coding sequence amino acid
      translation peptide

<400> SEQUENCE: 54

Arg Ala Thr Leu Thr Leu Leu Lys Gly Met Leu Ser Met Thr Leu
 1               5                  10                  15

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence:H. pylori
      strain 1218 FutA fucosyltransferase coding sequence amino acid
      translation peptide

<400> SEQUENCE: 55
```

-continued

```
Ser Gln Leu Gly Glu Gly Ala
 1               5
```

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence:H. pylori
      strain 1218 FutA fucosyltransferase coding sequence amino acid
      translation peptide

<400> SEQUENCE: 56

```
Ala Ile Thr Leu Lys Thr Arg Ala Ser Phe
 1               5                  10
```

<210> SEQ ID NO 57
<211> LENGTH: 17
<212> TYPE: PRT
<213> ORGANISM: Artificial Sequence
<220> FEATURE:
<223> OTHER INFORMATION: Description of Artificial Sequence:H. pylori
      strain 1218 FutA fucosyltransferase coding sequence amino acid
      translation peptide

<400> SEQUENCE: 57

```
Ala Asn Thr Asn Ser Ile Cys Val Leu Lys Thr His Lys Ala Met Ala
 1               5                  10                  15

Met
```

<210> SEQ ID NO 58
<211> LENGTH: 31
<212> TYPE: PRT
<213> ORGANISM: Artificial Sequence
<220> FEATURE:
<223> OTHER INFORMATION: Description of Artificial Sequence:H. pylori
      strain 1218 FutA fucosyltransferase coding sequence amino acid
      translation peptide

<400> SEQUENCE: 58

```
Leu Lys Lys Ser Leu Thr Leu Thr Leu Ala Ile Pro Phe Leu Phe Ile
 1               5                  10                  15

Gly Gly Val Leu Ala Trp His Lys Ile Leu Thr Leu Arg Val Leu
                20                  25                  30
```

<210> SEQ ID NO 59
<211> LENGTH: 25
<212> TYPE: PRT
<213> ORGANISM: Artificial Sequence
<220> FEATURE:
<223> OTHER INFORMATION: Description of Artificial Sequence:H. pylori
      strain 1218 FutA fucosyltransferase coding sequence amino acid
      translation peptide

<400> SEQUENCE: 59

```
Met Phe Val Ile Leu Lys Ile Leu Met Lys Arg Leu Ile Met Cys Asp
 1               5                  10                  15

Thr Cys Thr Arg Thr Gln Thr Leu Ile
                20                  25
```

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence:H. pylori
      strain 1218 FutA fucosyltransferase coding sequence amino acid -continued translation peptide

<400> SEQUENCE: 60

Thr Cys Phe Met Lys Thr Leu
1               5

<210> SEQ ID NO 61
<211> LENGTH: 171
<212> TYPE: PRT
<213> ORGANISM: Artificial Sequence
<220> FEATURE:
<223> OTHER INFORMATION: Description of Artificial Sequence:H. pylori
      strain 1218 FutA fucosyltransferase coding sequence amino acid
      translation peptide

<400> SEQUENCE: 61

Thr Pro Leu Met Gly Lys Leu Thr Phe Gln Asn Leu Ser Phe Lys Lys
1               5                   10                  15

Ile Leu Asp Phe Phe Lys Thr Ile Leu Glu Asn Asp Thr Ile Tyr His
            20                  25                  30

Asp Asn Pro Phe Ile Phe Tyr Arg Asp Leu Asn Glu Pro Leu Ile Ser
        35                  40                  45

Ile Asp Asp Leu Arg Val Asn Tyr Asp Asp Leu Arg Val Asn Tyr Asp
    50                  55                  60

Asp Leu Arg Val Asn Tyr Asp Asp Leu Arg Val Asn Tyr Asp Asp Leu
65                  70                  75                  80

Arg Val Asn Tyr Asp Asp Leu Arg Val Asn Tyr Asp Asp Leu Arg Val
                85                  90                  95

Asn Tyr Asp Asp Leu Arg Val Asn Tyr Asp Asp Leu Arg Val Asn Cys
            100                 105                 110

Asp Asp Leu Arg Val Asn Tyr Asp Asp Leu Arg Val Asn Tyr Glu Arg
        115                 120                 125

Leu Leu Gln Asn Ala Ser Pro Leu Leu Glu Leu Ser Gln Asn Thr Thr
    130                 135                 140

Phe Lys Ile Tyr Arg Lys Ala Tyr Gln Lys Ser Leu Pro Leu Leu Arg
145                 150                 155                 160

Ala Ala Arg Lys Leu Ile Lys Lys Leu Gly Leu
                165                 170

<210> SEQ ID NO 62
<211> LENGTH: 20
<212> TYPE: PRT
<213> ORGANISM: Artificial Sequence
<220> FEATURE:
<223> OTHER INFORMATION: Description of Artificial Sequence:H. pylori
      strain 1218 FutA fucosyltransferase coding sequence amino acid
      translation peptide

<400> SEQUENCE: 62

Ser Asn Pro Leu Arg Tyr His Arg Arg His Leu Ser Lys Thr Ser
1               5                   10                  15

Asp Ile Ser Pro
            20

<210> SEQ ID NO 63
<211> LENGTH: 35
<212> TYPE: PRT
<213> ORGANISM: Artificial Sequence
<220> FEATURE:
<223> OTHER INFORMATION: Description of Artificial Sequence:H. pylori
      strain 1218 FutA fucosyltransferase coding sequence amino acid
      translation peptide

<400> SEQUENCE: 63

Asn Lys Ile Ser Arg Val Phe Lys Leu Phe Ser Gly Leu Arg Asp Ile
 1               5                  10                  15

Leu Ile Arg Ile Arg Tyr Gln Ala Tyr Arg Tyr Arg Pro Arg Gly
            20                  25                  30

Gly Ala Arg
        35

<210> SEQ ID NO 64
<211> LENGTH: 231
<212> TYPE: PRT
<213> ORGANISM: Helicobacter pylori
<220> FEATURE:
<223> OTHER INFORMATION: H. pylori strain 1182 FutB fucosyltransferase
      catalytic domain conserved region positions 23-305

<400> SEQUENCE: 64

Pro Pro Pro Leu Lys Ile Ala Val Ala Asn Trp Trp Gly Asp Glu Glu
 1               5                  10                  15

Val Glu Glu Phe Lys Lys Asn Ile Leu Tyr Phe Ile Leu Ser Gln His
            20                  25                  30

Tyr Thr Ile Thr Leu His Gln Asn Pro Asn Glu Pro Ser Asp Leu Val
        35                  40                  45

Phe Gly Ser Pro Ile Gly Ser Ala Arg Lys Ile Leu Ser Tyr Gln Asn
    50                  55                  60

Ala Lys Arg Val Phe Tyr Thr Gly Glu Asn Glu Ser Pro Asn Phe Asn
65                  70                  75                  80

Leu Phe Asp Tyr Ala Ile Gly Phe Asp Glu Leu Asp Phe Arg Asp Arg
                85                  90                  95

Tyr Leu Arg Met Pro Leu Tyr Tyr Asp Arg Leu His His Lys Ala Glu
            100                 105                 110

Ser Val Asn Asp Thr Thr Ser Pro Tyr Lys Leu Lys Pro Asp Ser Leu
        115                 120                 125

Tyr Ala Leu Lys Lys Pro Ser His His Phe Lys Glu Asn His Pro Asn
    130                 135                 140

Leu Cys Ala Val Val Asn Asn Glu Ser Asp Pro Leu Lys Arg Gly Phe
145                 150                 155                 160

Ala Ser Phe Val Ala Ser Asn Pro Asn Ala Pro Lys Arg Asn Ala Phe
                165                 170                 175

Tyr Asp Val Leu Asn Ser Ile Glu Pro Val Ile Gly Gly Gly Ser Val
            180                 185                 190

Lys Asn Thr Leu Gly Tyr Asn Ile Lys Asn Lys Ser Glu Phe Leu Ser
        195                 200                 205

Gln Tyr Lys Phe Asn Leu Cys Phe Glu Asn Ser Gln Gly Tyr Gly Tyr
    210                 215                 220

Val Thr Glu Lys Ile Ile Asp
225                 230

<210> SEQ ID NO 65
<211> LENGTH: 291
<212> TYPE: PRT
<213> ORGANISM: Artificial Sequence
<220> FEATURE:
<223> OTHER INFORMATION: Description of Artificial Sequence:
      glycosyltransferase family 10 fucosyltransferase consensus
      sequence pfam00852 positions 11-301

<400> SEQUENCE: 65

Thr Val Pro Leu Leu Leu Ala Ile Tyr Thr Trp Trp Ser Leu Ile Glu
1               5                   10                  15

Tyr Lys Glu Trp Lys Lys Ser Pro Ile Tyr Phe Ile Gly Ser Gln Ala
            20                  25                  30

Pro Gln Pro Pro Leu Arg Ile Leu Leu Trp Thr Trp Pro Phe Asn Gly
        35                  40                  45

Asn Pro Leu Ala Leu Ser Asp Cys Pro Leu Ser Tyr Gln Asn Thr Ala
    50                  55                  60

Arg Cys Arg Leu Thr Ala Asn Arg Ser Pro Leu Glu Ser Ala Asp Ala
65                  70                  75                  80

Val Leu Phe His His Arg Asp Leu Ser Lys Gly Phe Pro Asp Leu Pro
                85                  90                  95

Pro Ser Pro Arg Pro Pro Gly Gln Pro Trp Val Trp Ala Ser Met Glu
            100                 105                 110

Ser Pro Ser Asn Ser Gly Leu Asn Asp Leu Arg Asp Gly Tyr Phe Asn
            115                 120                 125

Trp Thr Leu Ser Tyr Arg Ala Asp Ser Asp Ala Phe His Pro Tyr Gly
        130                 135                 140

Tyr Leu Glu Pro Arg Leu Ser Gln Val Val Asn Ala Pro Leu Leu Ser
145                 150                 155                 160

Ala Lys Arg Lys Gly Ala Ala Trp Val Val Ser Asn Cys Asn Thr Arg
                165                 170                 175

Ser Lys Arg Glu Arg Phe Tyr Lys Gln Leu Asn Lys His Leu Gln Val
            180                 185                 190

Asp Val Gly Gly Arg Val Ala Asn Pro Leu Pro Leu Lys Val Gly Cys
            195                 200                 205

Leu Val Glu Thr Leu Ser Gln Tyr Lys Phe Tyr Leu Ala Phe Glu Asn
    210                 215                 220

Ser Gln His Tyr Asp Tyr Val Thr Glu Lys Leu Trp Lys Asn Ala Leu
225                 230                 235                 240

Gln Ala Gly Thr Ile Pro Val Val Leu Gly Pro Arg Ala Val Tyr Glu
                245                 250                 255

Asp Phe Val Pro Pro Lys Ser Phe Ile His Val Asp Asp Phe Lys Ser
            260                 265                 270

Pro Lys Glu Leu Ala Asp Tyr Leu Leu Tyr Leu Asp Thr Asn Pro Thr
        275                 280                 285

Ala Tyr Ser
    290

<210> SEQ ID NO 66
<211> LENGTH: 391
<212> TYPE: PRT
<213> ORGANISM: Helicobacter pylori
<220> FEATURE:
<223> OTHER INFORMATION: H. pylori strain 1111 FutA fucosyltransferase
      catalytic domain conserved region positions 27-417

<400> SEQUENCE: 66

Ile Ala Val Ala Asn Trp Trp Gly Asp Glu Glu Ile Lys Lys Phe Lys
1               5                   10                  15

Lys Ser Val Leu Tyr Phe Ile Leu Ser Gln His Tyr Thr Ile Thr Leu
            20                  25                  30

His Arg Asn Pro Asp Lys Pro Ala Asp Ile Val Phe Gly Asn Pro Leu
        35                  40                  45

Gly Ser Ala Arg Lys Ile Leu Ser Tyr Gln Asn Ala Lys Arg Val Phe

-continued

```
                50                    55                    60
Tyr Thr Gly Glu Asn Glu Val Pro Asn Phe Asn Leu Phe Asp Tyr Ala
 65                   70                    75                    80

Ile Gly Phe Asp Glu Leu Asp Phe Arg Asp Tyr Leu Arg Met Pro
                 85                    90                    95

Leu Tyr Tyr Ala Tyr Leu His Tyr Lys Ala Glu Leu Val Asn Asp Thr
                100                   105                   110

Thr Ser Pro Tyr Lys Leu Gln Pro Asp Ser Leu Tyr Ala Leu Lys Lys
                115                   120                   125

Pro Ser His His Phe Lys Glu Asn His Pro Asn Leu Cys Ala Val Val
130                   135                   140

Asn Asn Glu Ser Asp Pro Leu Lys Arg Gly Phe Ala Ser Phe Val Ala
145                   150                   155                   160

Ser Asn Pro Asn Ala Pro Arg Arg Asn Ala Phe Tyr Glu Ala Leu Asn
                165                   170                   175

Ala Ile Glu Pro Val Ala Gly Gly Ser Val Lys Asn Thr Leu Gly
                180                   185                   190

Tyr Asn Val Lys Asn Lys Ser Glu Phe Leu Ser Gln Tyr Lys Phe Asn
                195                   200                   205

Leu Cys Phe Glu Asn Thr Gln Gly Tyr Gly Tyr Val Thr Glu Lys Ile
    210                   215                   220

Ile Asp Ala Tyr Phe Ser His Thr Ile Pro Ile Tyr Trp Gly Ser Pro
225                   230                   235                   240

Ser Val Ala Lys Asp Phe Asn Pro Lys Ser Phe Val Asn Val His Asp
                245                   250                   255

Phe Asn Asn Phe Asp Glu Ala Ile Asp Tyr Ile Arg Tyr Leu His Thr
                260                   265                   270

His Pro Asn Ala Tyr Leu Asp Met His Tyr Glu Asn Pro Leu Asn Thr
                275                   280                   285

Ile Asp Gly Lys Ala Tyr Phe Tyr Gln Asn Leu Ser Phe Lys Lys Ile
290                   295                   300

Leu Asp Phe Phe Lys Thr Ile Leu Glu Asn Asp Thr Ile Tyr His Asp
305                   310                   315                   320

Asn Pro Phe Ile Phe Tyr Arg Asp Leu Asn Glu Pro Ser Val Ser Ile
                325                   330                   335

Asp Gly Leu Arg Val Asn Tyr Asp Asp Leu Arg Val Asn Tyr Asp Asp
                340                   345                   350

Leu Arg Val Asn Tyr Asp Asp Leu Arg Val Asn Tyr Glu Arg Leu Leu
                355                   360                   365

Gln Asn Ala Ser Pro Leu Leu Glu Leu Ser Gln Asn Thr Thr Phe Lys
370                   375                   380

Ile Tyr Arg Lys Ala Tyr Gln
385                   390

<210> SEQ ID NO 67
<211> LENGTH: 336
<212> TYPE: PRT
<213> ORGANISM: Artificial Sequence
<220> FEATURE:
<223> OTHER INFORMATION: Description of Artificial Sequence:
      glycosyltransferase family 10 fucosyltransferase consensus
      sequence pfam00852 positions 16-351

<400> SEQUENCE: 67

Leu Ala Ile Tyr Thr Trp Trp Ser Leu Ile Glu Tyr Lys Glu Trp Lys
  1               5                  10                  15
```

Lys Ser Pro Ile Tyr Phe Ile Gly Ser Gln Ala Pro Gln Pro Pro Leu
                20                  25                  30

Arg Ile Leu Leu Trp Thr Trp Pro Phe Asn Gly Asn Pro Leu Ala Leu
            35                  40                  45

Ser Asp Cys Pro Leu Ser Tyr Gln Asn Thr Ala Arg Cys Arg Leu Thr
        50                  55                  60

Ala Asn Arg Ser Pro Leu Glu Ser Ala Asp Ala Val Leu Phe His His
65                  70                  75                  80

Arg Asp Leu Ser Lys Gly Phe Pro Asp Leu Pro Pro Ser Pro Arg Pro
                85                  90                  95

Pro Gly Gln Pro Trp Val Trp Ala Ser Met Glu Ser Pro Ser Asn Ser
            100                 105                 110

Gly Leu Asn Asp Leu Arg Asp Gly Tyr Phe Asn Trp Thr Leu Ser Tyr
        115                 120                 125

Arg Ala Asp Ser Asp Ala Phe His Pro Tyr Gly Tyr Leu Glu Pro Arg
130                 135                 140

Leu Ser Gln Val Val Asn Ala Pro Leu Leu Ser Ala Lys Arg Lys Gly
145                 150                 155                 160

Ala Ala Trp Val Val Ser Asn Cys Asn Thr Arg Ser Lys Arg Glu Arg
                165                 170                 175

Phe Tyr Lys Gln Leu Asn Lys His Leu Gln Val Asp Val Gly Gly Arg
            180                 185                 190

Val Ala Asn Pro Leu Pro Leu Lys Val Gly Cys Leu Val Glu Thr Leu
        195                 200                 205

Ser Gln Tyr Lys Phe Tyr Leu Ala Phe Glu Asn Ser Gln His Tyr Asp
210                 215                 220

Tyr Val Thr Glu Lys Leu Trp Lys Asn Ala Leu Gln Ala Gly Thr Ile
225                 230                 235                 240

Pro Val Val Leu Gly Pro Arg Ala Val Tyr Glu Asp Phe Val Pro Pro
                245                 250                 255

Lys Ser Phe Ile His Val Asp Asp Phe Lys Ser Pro Lys Glu Leu Ala
            260                 265                 270

Asp Tyr Leu Leu Tyr Leu Asp Thr Asn Pro Thr Ala Tyr Ser Glu Tyr
        275                 280                 285

Phe Glu Trp Arg Tyr Asp Leu Arg Val Arg Leu Phe Ser Trp Asp Ala
290                 295                 300

Leu Arg Tyr Asp Glu Gly Phe Cys Arg Val Cys Arg Leu Leu Gln Asn
305                 310                 315                 320

Ala Pro Asp Arg Tyr Lys Thr Tyr Pro Asn Ile Ala Lys Trp Phe Gln
                325                 330                 335

<210> SEQ ID NO 68
<211> LENGTH: 377
<212> TYPE: PRT
<213> ORGANISM: Helicobacter pylori
<220> FEATURE:
<223> OTHER INFORMATION: H. pylori strain 1218 FutB fucosyltransferase
      catalytic domain conserved region positions 23-399

<400> SEQUENCE: 68

Pro Pro Pro Leu Lys Ile Ala Val Ala Asn Trp Trp Gly Asp Glu Glu
1               5                   10                  15

Val Glu Glu Phe Lys Lys Asn Ile Leu Tyr Phe Ile Leu Ser Gln His
                20                  25                  30

Tyr Thr Ile Thr Leu His Gln Asn Pro Asn Glu Pro Ser Asp Leu Val

```
                35                  40                  45
Phe Gly Ser Pro Ile Gly Ser Ala Arg Lys Ile Leu Ser Tyr Gln Asn
         50                  55                  60

Ala Lys Arg Val Phe Tyr Thr Gly Glu Asn Glu Ser Pro Asn Phe Asn
 65                  70                  75                  80

Leu Phe Asp Tyr Ala Ile Gly Phe Asp Glu Leu Asp Phe Arg Asp Arg
                 85                  90                  95

Tyr Leu Arg Met Pro Leu Tyr Tyr Asp Arg Leu His His Lys Ala Glu
            100                 105                 110

Ser Val Asn Asp Thr Thr Ser Pro Tyr Lys Leu Lys Pro Asp Ser Leu
        115                 120                 125

Tyr Ala Leu Lys Lys Pro Ser His His Phe Lys Glu Asn His Pro Asn
    130                 135                 140

Leu Cys Ala Val Val Asn Asn Glu Ser Asp Pro Leu Lys Arg Gly Phe
145                 150                 155                 160

Ala Ser Phe Val Ala Ser Asn Pro Asn Ala Pro Lys Arg Asn Ala Phe
                165                 170                 175

Tyr Asp Ala Leu Asn Ser Ile Glu Pro Val Ile Gly Gly Ser Val
            180                 185                 190

Lys Asn Thr Leu Gly Tyr Asn Ile Lys Asn Lys Ser Glu Phe Leu Ser
            195                 200                 205

Gln Tyr Lys Phe Asn Leu Cys Phe Glu Asn Ser Gln Gly Tyr Gly Tyr
        210                 215                 220

Val Thr Glu Lys Ile Ile Asp Ala Tyr Phe Ser His Thr Ile Pro Ile
225                 230                 235                 240

Tyr Trp Gly Ser Pro Ser Val Ala Gln Asp Phe Asn Pro Lys Ser Phe
                245                 250                 255

Val Asn Val Cys Asp Phe Lys Asp Phe Asp Glu Ala Ile Asp His Val
                260                 265                 270

Arg Tyr Leu His Thr His Pro Asn Ala Tyr Leu Asp Met Leu Tyr Glu
            275                 280                 285

Asn Pro Leu Asn Thr Leu Asp Gly Lys Ala Tyr Phe Tyr Gln Asn Leu
        290                 295                 300

Ser Phe Lys Lys Ile Leu Asp Phe Phe Lys Thr Ile Leu Glu Asn Asp
305                 310                 315                 320

Thr Ile Tyr His Asp Asn Pro Phe Ile Phe Tyr Arg Asp Leu Asn Glu
                325                 330                 335

Pro Leu Ile Ser Ile Asp Asp Leu Arg Val Asn Tyr Asp Asp Leu Arg
            340                 345                 350

Val Asn Tyr Asp Asp Leu Arg Val Asn Tyr Asp Asp Leu Arg Val Asn
        355                 360                 365

Tyr Asp Asp Leu Arg Val Asn Tyr Asp
    370                 375

<210> SEQ ID NO 69
<211> LENGTH: 341
<212> TYPE: PRT
<213> ORGANISM: Artificial Sequence
<220> FEATURE:
<223> OTHER INFORMATION: Description of Artificial Sequence:
      glycosyltransferase family 10 fucosyltransferase consensus
      sequence pfam00852 positions 11-351

<400> SEQUENCE: 69

Thr Val Pro Leu Leu Ala Ile Tyr Thr Trp Trp Ser Leu Ile Glu
 1               5                  10                  15
```

```
Tyr Lys Glu Trp Lys Lys Ser Pro Ile Tyr Phe Ile Gly Ser Gln Ala
             20                  25                  30

Pro Gln Pro Pro Leu Arg Ile Leu Leu Trp Thr Trp Pro Phe Asn Gly
         35                  40                  45

Asn Pro Leu Ala Leu Ser Asp Cys Pro Leu Ser Tyr Gln Asn Thr Ala
     50                  55                  60

Arg Cys Arg Leu Thr Ala Asn Arg Ser Pro Leu Glu Ser Ala Asp Ala
 65                  70                  75                  80

Val Leu Phe His His Arg Asp Leu Ser Lys Gly Phe Pro Asp Leu Pro
                 85                  90                  95

Pro Ser Pro Arg Pro Gly Gln Pro Trp Val Trp Ala Ser Met Glu
            100                 105                 110

Ser Pro Ser Asn Ser Gly Leu Asn Asp Leu Arg Asp Gly Tyr Phe Asn
            115                 120                 125

Trp Thr Leu Ser Tyr Arg Ala Asp Ser Asp Ala Phe His Pro Tyr Gly
        130                 135                 140

Tyr Leu Glu Pro Arg Leu Ser Gln Val Val Asn Ala Pro Leu Leu Ser
145                 150                 155                 160

Ala Lys Arg Lys Gly Ala Ala Trp Val Val Ser Asn Cys Asn Thr Arg
                165                 170                 175

Ser Lys Arg Glu Arg Phe Tyr Lys Gln Leu Asn Lys His Leu Gln Val
            180                 185                 190

Asp Val Gly Gly Arg Val Ala Asn Pro Leu Pro Leu Lys Val Gly Cys
        195                 200                 205

Leu Val Glu Thr Leu Ser Gln Tyr Lys Phe Tyr Leu Ala Phe Glu Asn
    210                 215                 220

Ser Gln His Tyr Asp Tyr Val Thr Glu Lys Leu Trp Lys Asn Ala Leu
225                 230                 235                 240

Gln Ala Gly Thr Ile Pro Val Val Leu Gly Pro Arg Ala Val Tyr Glu
                245                 250                 255

Asp Phe Val Pro Pro Lys Ser Phe Ile His Val Asp Asp Phe Lys Ser
            260                 265                 270

Pro Lys Glu Leu Ala Asp Tyr Leu Leu Tyr Leu Asp Thr Asn Pro Thr
        275                 280                 285

Ala Tyr Ser Glu Tyr Phe Glu Trp Arg Tyr Asp Leu Arg Val Arg Leu
    290                 295                 300

Phe Ser Trp Asp Ala Leu Arg Tyr Asp Glu Gly Phe Cys Arg Val Cys
305                 310                 315                 320

Arg Leu Leu Gln Asn Ala Pro Asp Arg Tyr Lys Thr Tyr Pro Asn Ile
                325                 330                 335

Ala Lys Trp Phe Gln
            340

<210> SEQ ID NO 70
<211> LENGTH: 256
<212> TYPE: PRT
<213> ORGANISM: Helicobacter pylori
<220> FEATURE:
<223> OTHER INFORMATION: H. pylori strain 19C2 FutB fucosyltransferase
      catalytic domain conserved region positions 22-277

<400> SEQUENCE: 70

Pro Pro Leu Asn Ile Ala Leu Ala Asn Trp Trp Pro Leu Asp Lys Arg
  1               5                  10                  15

Glu Ser Lys Gly Phe Arg Lys Lys Phe Ile Leu His Phe Ile Leu Ser
```

```
                    20                  25                  30
Gln His Tyr Thr Ile Ala Leu His Arg Asn Pro Asp Lys Pro Ala Asp
            35                  40                  45

Ile Val Phe Gly Asn Pro Leu Gly Ser Ala Arg Lys Ile Leu Ser Tyr
    50                  55                  60

Gln Asn Ala Lys Arg Val Phe Tyr Thr Gly Glu Asn Glu Val Pro Asn
65                  70                  75                  80

Phe Asn Leu Phe Asp Tyr Ala Ile Gly Phe Asp Glu Leu Asp Phe Arg
                85                  90                  95

Asp Arg Tyr Leu Arg Met Pro Leu Tyr Tyr Asp Arg Leu His His Lys
            100                 105                 110

Ala Glu Ser Val Asn Asp Thr Thr Ala Pro Tyr Lys Ile Lys Ser Asp
            115                 120                 125

Ser Leu Tyr Ala Leu Lys Lys Pro Ser His His Phe Lys Glu Asn His
    130                 135                 140

Pro His Leu Cys Ala Leu Ile Asn Asn Glu Ile Asp Pro Leu Lys Arg
145                 150                 155                 160

Gly Phe Ala Ser Phe Val Ala Ser Asn Pro Asn Ala Pro Ile Arg Asn
                165                 170                 175

Ala Phe Tyr Glu Ala Leu Asn Ser Ile Glu Pro Val Thr Gly Gly Gly
            180                 185                 190

Ser Val Arg Asn Thr Leu Gly Tyr Asn Val Lys Asn Lys Asn Glu Phe
    195                 200                 205

Leu Ser Gln Tyr Lys Phe Asn Leu Cys Phe Glu Asn Thr Gln Gly Tyr
    210                 215                 220

Gly Tyr Val Thr Glu Lys Ile Ile Asp Ala Tyr Phe Ser His Thr Ile
225                 230                 235                 240

Pro Ile Tyr Trp Gly Gly Val Pro Ser Val Ala Lys Asp Phe Asn Pro
                245                 250                 255

<210> SEQ ID NO 71
<211> LENGTH: 259
<212> TYPE: PRT
<213> ORGANISM: Artificial Sequence
<220> FEATURE:
<223> OTHER INFORMATION: Description of Artificial Sequence:
      glycosyltransferase family 10 fucosyltransferase consensus
      sequence pfam00852 positions 12-270

<400> SEQUENCE: 71

Val Pro Leu Leu Leu Ala Ile Tyr Thr Trp Trp Ser Leu Ile Glu Tyr
1               5                   10                  15

Lys Glu Trp Lys Lys Ser Pro Ile Tyr Phe Ile Gly Ser Gln Ala Pro
            20                  25                  30

Gln Pro Pro Leu Arg Ile Leu Leu Trp Thr Trp Pro Phe Asn Gly Asn
            35                  40                  45

Pro Leu Ala Leu Ser Asp Cys Pro Leu Ser Tyr Gln Asn Thr Ala Arg
    50                  55                  60

Cys Arg Leu Thr Ala Asn Arg Ser Pro Leu Glu Ser Ala Asp Ala Val
65                  70                  75                  80

Leu Phe His His Arg Asp Leu Ser Lys Gly Phe Pro Asp Leu Pro Pro
                85                  90                  95

Ser Pro Arg Pro Pro Gly Gln Pro Trp Val Trp Ala Ser Met Glu Ser
            100                 105                 110

Pro Ser Asn Ser Gly Leu Asn Asp Leu Arg Asp Gly Tyr Phe Asn Trp
    115                 120                 125
```

```
Thr Leu Ser Tyr Arg Ala Asp Ser Asp Ala Phe His Pro Tyr Gly Tyr
        130                 135                 140

Leu Glu Pro Arg Leu Ser Gln Val Val Asn Ala Pro Leu Leu Ser Ala
145                 150                 155                 160

Lys Arg Lys Gly Ala Ala Trp Val Val Ser Asn Cys Asn Thr Arg Ser
                165                 170                 175

Lys Arg Glu Arg Phe Tyr Lys Gln Leu Asn Lys His Leu Gln Val Asp
            180                 185                 190

Val Gly Gly Arg Val Ala Asn Pro Leu Pro Leu Lys Val Gly Cys Leu
        195                 200                 205

Val Glu Thr Leu Ser Gln Tyr Lys Phe Tyr Leu Ala Phe Glu Asn Ser
    210                 215                 220

Gln His Tyr Asp Tyr Val Thr Glu Lys Leu Trp Lys Asn Ala Leu Gln
225                 230                 235                 240

Ala Gly Thr Ile Pro Val Val Leu Gly Pro Arg Ala Val Tyr Glu Asp
                245                 250                 255

Phe Val Pro

<210> SEQ ID NO 72
<211> LENGTH: 245
<212> TYPE: PRT
<213> ORGANISM: Helicobacter pylori
<220> FEATURE:
<223> OTHER INFORMATION: H. pylori strain 1111 FutA fucosyltransferase
      positions 1-245 (1111FutA.pep)

<400> SEQUENCE: 72

Met Phe Gln Pro Leu Leu Asp Ala Phe Ile Glu Ser Ala Pro Leu Lys
1               5                   10                  15

Lys Trp Pro Leu Asn Leu Pro Pro Leu Lys Ile Ala Val Ala Asn Trp
                20                  25                  30

Trp Gly Asp Glu Glu Ile Lys Lys Phe Lys Lys Ser Val Leu Tyr Phe
            35                  40                  45

Ile Leu Ser Gln His Tyr Thr Ile Thr Leu His Arg Asn Pro Asp Lys
    50                  55                  60

Pro Ala Asp Ile Val Phe Gly Asn Pro Leu Gly Ser Ala Arg Lys Ile
65                  70                  75                  80

Leu Ser Tyr Gln Asn Ala Lys Arg Val Phe Tyr Thr Gly Glu Asn Glu
                85                  90                  95

Val Pro Asn Phe Asn Leu Phe Asp Tyr Ala Ile Gly Phe Asp Glu Leu
                100                 105                 110

Asp Phe Arg Asp Arg Tyr Leu Arg Met Pro Leu Tyr Tyr Ala Tyr Leu
            115                 120                 125

His Tyr Lys Ala Glu Leu Val Asn Asp Thr Thr Ser Pro Tyr Lys Leu
        130                 135                 140

Gln Pro Asp Ser Leu Tyr Ala Leu Lys Lys Pro Ser His His Phe Lys
145                 150                 155                 160

Glu Asn His Pro Asn Leu Cys Ala Val Val Asn Asn Glu Ser Asp Pro
                165                 170                 175

Leu Lys Arg Gly Phe Ala Ser Phe Val Ala Ser Asn Pro Asn Ala Pro
            180                 185                 190

Arg Arg Asn Ala Phe Tyr Glu Ala Leu Asn Ala Ile Glu Pro Val Ala
        195                 200                 205

Gly Gly Gly Ser Val Lys Asn Thr Leu Gly Tyr Asn Val Lys Asn Lys
    210                 215                 220
```

Ser Glu Phe Leu Ser Gln Tyr Lys Phe Asn Leu Cys Phe Glu Asn Thr
225                 230                 235                 240

Gln Gly Tyr Gly Tyr
            245

<210> SEQ ID NO 73
<211> LENGTH: 247
<212> TYPE: PRT
<213> ORGANISM: Helicobacter pylori
<220> FEATURE:
<223> OTHER INFORMATION: H. pylori strain 26695 FutA fucosyltransferase
      positions 1-247 (26695A.pep)

<400> SEQUENCE: 73

Met Phe Gln Pro Leu Leu Asp Ala Phe Ile Glu Ser Ala Ser Ile Glu
1               5                   10                  15

Lys Met Ala Ser Lys Ser Pro Pro Pro Leu Lys Ile Ala Val Ala
            20                  25                  30

Asn Trp Trp Gly Asp Glu Glu Ile Lys Glu Phe Lys Lys Ser Val Leu
            35                  40                  45

Tyr Phe Ile Leu Ser Gln Arg Tyr Ala Ile Thr Leu His Gln Asn Pro
    50                  55                  60

Asn Glu Phe Ser Asp Leu Val Phe Ser Asn Pro Leu Gly Ala Ala Arg
65                  70                  75                  80

Lys Ile Leu Ser Tyr Gln Asn Thr Lys Arg Val Phe Tyr Thr Gly Glu
                85                  90                  95

Asn Glu Ser Pro Asn Phe Asn Leu Phe Asp Tyr Ala Ile Gly Phe Asp
            100                 105                 110

Glu Leu Asp Phe Asn Asp Arg Tyr Leu Arg Met Pro Leu Tyr Tyr Ala
        115                 120                 125

His Leu His Tyr Lys Ala Glu Leu Val Asn Asp Thr Thr Ala Pro Tyr
    130                 135                 140

Lys Leu Lys Asp Asn Ser Leu Tyr Ala Leu Lys Lys Pro Ser His His
145                 150                 155                 160

Phe Lys Glu Asn His Pro Asn Leu Cys Ala Val Val Asn Asp Glu Ser
                165                 170                 175

Asp Leu Leu Lys Arg Gly Phe Ala Ser Phe Val Ala Ser Asn Ala Asn
            180                 185                 190

Ala Pro Met Arg Asn Ala Phe Tyr Asp Ala Leu Asn Ser Ile Glu Pro
        195                 200                 205

Val Thr Gly Gly Gly Ser Val Arg Asn Thr Leu Gly Tyr Lys Val Gly
    210                 215                 220

Asn Lys Ser Glu Phe Leu Ser Gln Tyr Lys Phe Asn Leu Cys Phe Glu
225                 230                 235                 240

Asn Ser Gln Gly Tyr Gly Tyr
            245

<210> SEQ ID NO 74
<211> LENGTH: 246
<212> TYPE: PRT
<213> ORGANISM: Helicobacter pylori
<220> FEATURE:
<223> OTHER INFORMATION: H. pylori strain 1182 FutB fucosyltransferase
      positions 1-246 (1182B.pep)

<400> SEQUENCE: 74

Met Phe Gln Pro Leu Leu Asp Ala Tyr Ile Glu Ser Ala Ser Ile Glu
1               5                   10                  15

```
Lys Ile Thr Ser Lys Ser Pro Pro Leu Lys Ile Ala Val Ala Asn
            20                  25                  30

Trp Trp Gly Asp Glu Glu Val Glu Glu Phe Lys Lys Asn Ile Leu Tyr
        35                  40                  45

Phe Ile Leu Ser Gln His Tyr Thr Ile Thr Leu His Gln Asn Pro Asn
    50                  55                  60

Glu Pro Ser Asp Leu Val Phe Gly Ser Pro Ile Gly Ser Ala Arg Lys
65                  70                  75                  80

Ile Leu Ser Tyr Gln Asn Ala Lys Arg Val Phe Tyr Thr Gly Glu Asn
                85                  90                  95

Glu Ser Pro Asn Phe Asn Leu Phe Asp Tyr Ala Ile Gly Phe Asp Glu
            100                 105                 110

Leu Asp Phe Arg Asp Arg Tyr Leu Arg Met Pro Leu Tyr Tyr Asp Arg
        115                 120                 125

Leu His His Lys Ala Glu Ser Val Asn Asp Thr Thr Ser Pro Tyr Lys
    130                 135                 140

Leu Lys Pro Asp Ser Leu Tyr Ala Leu Lys Lys Pro Ser His His Phe
145                 150                 155                 160

Lys Glu Asn His Pro Asn Leu Cys Ala Val Val Asn Asn Glu Ser Asp
                165                 170                 175

Pro Leu Lys Arg Gly Phe Ala Ser Phe Val Ala Ser Asn Pro Asn Ala
            180                 185                 190

Pro Lys Arg Asn Ala Phe Tyr Asp Val Leu Asn Ser Ile Glu Pro Val
        195                 200                 205

Ile Gly Gly Gly Ser Val Lys Asn Thr Leu Gly Tyr Asn Ile Lys Asn
    210                 215                 220

Lys Ser Glu Phe Leu Ser Gln Tyr Lys Phe Asn Leu Cys Phe Glu Asn
225                 230                 235                 240

Ser Gln Gly Tyr Gly Tyr
                245

<210> SEQ ID NO 75
<211> LENGTH: 246
<212> TYPE: PRT
<213> ORGANISM: Helicobacter pylori
<220> FEATURE:
<223> OTHER INFORMATION: H. pylori strain 1218 FutB fucosyltransferase
      positions 1-246 (1218B.pep)

<400> SEQUENCE: 75

Met Phe Gln Pro Leu Leu Asp Ala Tyr Ile Glu Ser Ala Ser Ile Glu
1               5                   10                  15

Lys Ile Thr Ser Lys Ser Pro Pro Leu Lys Ile Ala Val Ala Asn
            20                  25                  30

Trp Trp Gly Asp Glu Glu Val Glu Glu Phe Lys Lys Asn Ile Leu Tyr
        35                  40                  45

Phe Ile Leu Ser Gln His Tyr Thr Ile Thr Leu His Gln Asn Pro Asn
    50                  55                  60

Glu Pro Ser Asp Leu Val Phe Gly Ser Pro Ile Gly Ser Ala Arg Lys
65                  70                  75                  80

Ile Leu Ser Tyr Gln Asn Ala Lys Arg Val Phe Tyr Thr Gly Glu Asn
                85                  90                  95

Glu Ser Pro Asn Phe Asn Leu Phe Asp Tyr Ala Ile Gly Phe Asp Glu
            100                 105                 110

Leu Asp Phe Arg Asp Arg Tyr Leu Arg Met Pro Leu Tyr Tyr Asp Arg
```

```
                115                 120                 125
Leu His His Lys Ala Glu Ser Val Asn Asp Thr Thr Ser Pro Tyr Lys
        130                 135                 140

Leu Lys Pro Asp Ser Leu Tyr Ala Leu Lys Lys Pro Ser His His Phe
145                 150                 155                 160

Lys Glu Asn His Pro Asn Leu Cys Ala Val Val Asn Asn Glu Ser Asp
                165                 170                 175

Pro Leu Lys Arg Gly Phe Ala Ser Phe Val Ala Ser Asn Pro Asn Ala
            180                 185                 190

Pro Lys Arg Asn Ala Phe Tyr Asp Ala Leu Asn Ser Ile Glu Pro Val
            195                 200                 205

Ile Gly Gly Gly Ser Val Lys Asn Thr Leu Gly Tyr Asn Ile Lys Asn
        210                 215                 220

Lys Ser Glu Phe Leu Ser Gln Tyr Lys Phe Asn Leu Cys Phe Glu Asn
225                 230                 235                 240

Ser Gln Gly Tyr Gly Tyr
                245

<210> SEQ ID NO 76
<211> LENGTH: 247
<212> TYPE: PRT
<213> ORGANISM: Helicobacter pylori
<220> FEATURE:
<223> OTHER INFORMATION: H. pylori strain 19C2 FutB fucosyltransferase
      positions 1-247 (ORF19C2B.pep)

<400> SEQUENCE: 76

Met Phe Gln Pro Leu Leu Asp Ala Tyr Ile Asp Ser Thr Arg Leu Asp
  1               5                  10                  15

Glu Thr Asp Tyr Lys Pro Pro Leu Asn Ile Ala Leu Ala Asn Trp Trp
                20                  25                  30

Pro Leu Asp Lys Arg Glu Ser Lys Gly Phe Arg Lys Lys Phe Ile Leu
            35                  40                  45

His Phe Ile Leu Ser Gln His Tyr Thr Ile Ala Leu His Arg Asn Pro
        50                  55                  60

Asp Lys Pro Ala Asp Ile Val Phe Gly Asn Pro Leu Gly Ser Ala Arg
65                  70                  75                  80

Lys Ile Leu Ser Tyr Gln Asn Ala Lys Arg Val Phe Tyr Thr Gly Glu
                85                  90                  95

Asn Glu Val Pro Asn Phe Asn Leu Phe Asp Tyr Ala Ile Gly Phe Asp
                100                 105                 110

Glu Leu Asp Phe Arg Asp Arg Tyr Leu Arg Met Pro Leu Tyr Tyr Asp
            115                 120                 125

Arg Leu His His Lys Ala Glu Ser Val Asn Asp Thr Thr Ala Pro Tyr
        130                 135                 140

Lys Ile Lys Ser Asp Ser Leu Tyr Ala Leu Lys Lys Pro Ser His His
145                 150                 155                 160

Phe Lys Glu Asn His Pro His Leu Cys Ala Leu Ile Asn Asn Glu Ile
                165                 170                 175

Asp Pro Leu Lys Arg Gly Phe Ala Ser Phe Val Ala Ser Asn Pro Asn
            180                 185                 190

Ala Pro Ile Arg Asn Ala Phe Tyr Glu Ala Leu Asn Ser Ile Glu Pro
            195                 200                 205

Val Thr Gly Gly Gly Ser Val Arg Asn Thr Leu Gly Tyr Asn Val Lys
        210                 215                 220
```

```
Asn Lys Asn Glu Phe Leu Ser Gln Tyr Lys Phe Asn Leu Cys Phe Glu
225                 230                 235                 240

Asn Thr Gln Gly Tyr Gly Tyr
                245
```

<210> SEQ ID NO 77
<211> LENGTH: 250
<212> TYPE: PRT
<213> ORGANISM: Artificial Sequence
<220> FEATURE:
<223> OTHER INFORMATION: Description of Artificial
      Sequence:fucosyltransferase consensus sequence
<220> FEATURE:
<221> NAME/KEY: MOD_RES
<222> LOCATION: (14)
<223> OTHER INFORMATION: Xaa = Pro, Ser or Arg
<220> FEATURE:
<221> NAME/KEY: MOD_RES
<222> LOCATION: (18)
<223> OTHER INFORMATION: Xaa = Trp, Met, Ile or Thr
<220> FEATURE:
<221> NAME/KEY: MOD_RES
<222> LOCATION: (19)
<223> OTHER INFORMATION: Xaa = Pro, Met, Ala, Thr or Asp
<220> FEATURE:
<221> NAME/KEY: MOD_RES
<222> LOCATION: (22)
<223> OTHER INFORMATION: Xaa = Lys, Ser or absent
<220> FEATURE:
<221> NAME/KEY: MOD_RES
<222> LOCATION: (23)
<223> OTHER INFORMATION: Xaa = Pro or absent
<220> FEATURE:
<221> NAME/KEY: MOD_RES
<222> LOCATION: (24)
<223> OTHER INFORMATION: Xaa = Leu, Ser, Pro or absent
<220> FEATURE:
<221> NAME/KEY: MOD_RES
<222> LOCATION: (41)
<223> OTHER INFORMATION: Xaa = Lys or Glu
<220> FEATURE:
<221> NAME/KEY: MOD_RES
<222> LOCATION: (42)
<223> OTHER INFORMATION: Xaa = Lys, Glu or Ser
<220> FEATURE:
<221> NAME/KEY: MOD_RES
<222> LOCATION: (43)
<223> OTHER INFORMATION: Xaa = Lys or absent
<220> FEATURE:
<221> NAME/KEY: MOD_RES
<222> LOCATION: (44)
<223> OTHER INFORMATION: Xaa = Gly or absent
<220> FEATURE:
<221> NAME/KEY: MOD_RES
<222> LOCATION: (45)
<223> OTHER INFORMATION: Xaa = Phe or absent
<220> FEATURE:
<221> NAME/KEY: MOD_RES
<222> LOCATION: (49)
<223> OTHER INFORMATION: Xaa = Ser, Asn or Phe
<220> FEATURE:
<221> NAME/KEY: MOD_RES
<222> LOCATION: (65)
<223> OTHER INFORMATION: Xaa = Arg or Gln
<220> FEATURE:
<221> NAME/KEY: MOD_RES
<222> LOCATION: (69)
<223> OTHER INFORMATION: Xaa = Lys or Glu
<220> FEATURE:
<221> NAME/KEY: MOD_RES
<222> LOCATION: (102)
<223> OTHER INFORMATION: Xaa = Val or Ser
<220> FEATURE:
<221> NAME/KEY: MOD_RES
<222> LOCATION: (131)
<223> OTHER INFORMATION: Xaa = Ala or Asp
<220> FEATURE:

<221> NAME/KEY: MOD_RES
<222> LOCATION: (132)
<223> OTHER INFORMATION: Xaa = Tyr, His or Arg
<220> FEATURE:
<221> NAME/KEY: MOD_RES
<222> LOCATION: (139)
<223> OTHER INFORMATION: Xaa = Leu or Ser
<220> FEATURE:
<221> NAME/KEY: MOD_RES
<222> LOCATION: (151)
<223> OTHER INFORMATION: Xaa = Pro, Asp or Ser
<220> FEATURE:
<221> NAME/KEY: MOD_RES
<222> LOCATION: (198)
<223> OTHER INFORMATION: Xaa = Arg, Met, Lys or Ile
<220> FEATURE:
<221> NAME/KEY: MOD_RES
<222> LOCATION: (213)
<223> OTHER INFORMATION: Xaa = Ala, Thr or Ile

<400> SEQUENCE: 77

```
Met Phe Gln Pro Leu Leu Asp Ala Phe Ile Glu Ser Ala Xaa Ile Glu
  1               5                  10                  15

Lys Xaa Xaa Ser Lys Xaa Xaa Xaa Pro Pro Leu Lys Ile Ala Val Ala
             20                  25                  30

Asn Trp Trp Gly Asp Glu Glu Ile Xaa Xaa Xaa Xaa Xaa Phe Lys Lys
         35                  40                  45

Xaa Ile Leu Tyr Phe Ile Leu Ser Gln His Tyr Thr Ile Thr Leu His
     50                  55                  60

Xaa Asn Pro Asx Xaa Pro Ala Asp Ile Val Phe Gly Asn Pro Leu Gly
 65                  70                  75                  80

Ser Ala Arg Lys Ile Leu Ser Tyr Gln Asn Ala Lys Arg Val Phe Tyr
                 85                  90                  95

Thr Gly Glu Asn Glu Xaa Pro Asn Phe Asn Leu Phe Asp Tyr Ala Ile
            100                 105                 110

Gly Phe Asp Glu Leu Asp Phe Arg Asp Arg Tyr Leu Arg Met Pro Leu
        115                 120                 125

Tyr Tyr Xaa Xaa Leu His His Lys Ala Glu Xaa Val Asn Asp Thr Thr
    130                 135                 140

Ser Pro Tyr Lys Leu Lys Xaa Asp Ser Leu Tyr Ala Leu Lys Lys Pro
145                 150                 155                 160

Ser His His Phe Lys Glu Asn His Pro Asn Leu Cys Ala Val Val Asn
                165                 170                 175

Asn Glu Ser Asp Pro Leu Lys Arg Gly Phe Ala Ser Phe Val Ala Ser
            180                 185                 190

Asn Pro Asn Ala Pro Xaa Arg Asn Ala Phe Tyr Asp Ala Leu Asn Ser
        195                 200                 205

Ile Glu Pro Val Xaa Gly Gly Gly Ser Val Lys Asn Thr Leu Gly Tyr
    210                 215                 220

Asn Val Lys Asn Lys Ser Glu Phe Leu Ser Gln Tyr Lys Phe Asn Leu
225                 230                 235                 240

Cys Phe Glu Asn Ser Gln Gly Tyr Gly Tyr
                245                 250
```

<210> SEQ ID NO 78
<211> LENGTH: 333
<212> TYPE: DNA
<213> ORGANISM: Helicobacter pylori
<220> FEATURE:
<223> OTHER INFORMATION: H. pylori strain 915 FutA fucosyltransferase
      (915A.cod(MWG))

-continued

```
<400> SEQUENCE: 78
atgttccaac ccctattaga tgcctttata gaaagcgctt ccattgaaaa aatggcctct      60
aaatctcccc ccctaaaaat cgctgtggcg aattggtggg gagatgaaga aattaaaaaa     120
tttaaaaaga gcgttctttta ttttatccta agccagcatt acacaatcac tttacaccga    180
aaccctgata aacctgcgga catcgtcttt ggtaaccccc ttggatcagc cagaaaaatc     240
ttatcctatc aaaacgcaaa aagggtgttt tacaccggtg aaaatgaagt ccctaacttc     300
aacctctttg attacgccat aggctttga tga                                    333

<210> SEQ ID NO 79
<211> LENGTH: 1483
<212> TYPE: DNA
<213> ORGANISM: Artificial Sequence
<220> FEATURE:
<223> OTHER INFORMATION: Description of Artificial
      Sequence:fucosyltransferase consensus sequence
<220> FEATURE:
<221> NAME/KEY: modified_base
<222> LOCATION: (77)..(79)
<223> OTHER INFORMATION: n = c or absent
<220> FEATURE:
<221> NAME/KEY: modified_base
<222> LOCATION: (106)..(107)
<223> OTHER INFORMATION: n = c or absent
<220> FEATURE:
<221> NAME/KEY: modified_base
<222> LOCATION: (108)..(110)
<223> OTHER INFORMATION: n = t or absent
<220> FEATURE:
<221> NAME/KEY: modified_base
<222> LOCATION: (119)
<223> OTHER INFORMATION: n = g or absent
<220> FEATURE:
<221> NAME/KEY: modified_base
<222> LOCATION: (152)
<223> OTHER INFORMATION: n = t or absent
<220> FEATURE:
<221> NAME/KEY: modified_base
<222> LOCATION: (153)
<223> OTHER INFORMATION: n = a or absent
<220> FEATURE:
<221> NAME/KEY: modified_base
<222> LOCATION: (154)
<223> OTHER INFORMATION: n = c or absent
<220> FEATURE:
<221> NAME/KEY: modified_base
<222> LOCATION: (343)
<223> OTHER INFORMATION: n = t or absent
<220> FEATURE:
<221> NAME/KEY: modified_base
<222> LOCATION: (809)..(810)
<223> OTHER INFORMATION: n = g or absent
<220> FEATURE:
<221> NAME/KEY: modified_base
<222> LOCATION: (816)
<223> OTHER INFORMATION: n = c or absent
<220> FEATURE:
<221> NAME/KEY: modified_base
<222> LOCATION: (1063)..(1064)
<223> OTHER INFORMATION: n = a or absent
<220> FEATURE:
<221> NAME/KEY: modified_base
<222> LOCATION: (1065)
<223> OTHER INFORMATION: n = c or absent
<220> FEATURE:
<221> NAME/KEY: modified_base
<222> LOCATION: (1066)
<223> OTHER INFORMATION: n = a or absent
<220> FEATURE:
<221> NAME/KEY: modified_base
<222> LOCATION: (1067)
<223> OTHER INFORMATION: n = t or absent
<220> FEATURE:
```

<221> NAME/KEY: modified_base
<222> LOCATION: (1068)
<223> OTHER INFORMATION: n = c or absent
<220> FEATURE:
<221> NAME/KEY: modified_base
<222> LOCATION: (1118)
<223> OTHER INFORMATION: n = g or absent
<220> FEATURE:
<221> NAME/KEY: modified_base
<222> LOCATION: (1119)
<223> OTHER INFORMATION: n = a or absent
<220> FEATURE:
<221> NAME/KEY: modified_base
<222> LOCATION: (1120)
<223> OTHER INFORMATION: n = t or absent

<400> SEQUENCE: 79

| | | | | | |
|---|---|---|---|---|---|
| atgttccaac | ccctattaga | cgcctttata | gaaagcgctt | ccattgaaaa | aatbgcctct | 60 |
| aaatctcccc | ccccmynnnt | aaaaatcgct | gtggcgaatt | ggtggnnnnn | ggagatgana | 120 |
| gaaattaaag | aatttaaaaa | garcdttctt | tnnnatttta | tyctaagyca | gcattacaca | 180 |
| atcacyctcc | accraaaccc | yratraacct | kcvgaymtcg | tctttggyaa | yccycttgga | 240 |
| tcagccagaa | aaatcttatc | ctatcaaaac | gcaaaaagrg | tgttttacac | cggtgaaaac | 300 |
| gaakyvccta | atttcaacct | ctttgattac | gccataggct | ttngatgaat | tggayttag | 360 |
| agatcgttat | ttragaatgc | cttrtatta | tgmyhrwytr | cacyataaag | ccgagmkygt | 420 |
| kaatgacacc | actkcgcctt | acaaactcaa | abctgacagc | ctttatgctt | taaaaaaacc | 480 |
| ctcccatcat | tttaaagaaa | accaccchaa | tttrtgcgca | gtagtgaaya | atgagagcga | 540 |
| tcctttgaaa | agagggtttg | cgagytttgt | mgcragcaac | cctaacgctc | ctadaaggaa | 600 |
| ygctttytat | gasgctttaa | attctatwga | gccagttayt | gggggaggga | gcgtgaraaa | 660 |
| cactttaggc | tataabrtya | aaaacaarag | cgagttttta | agccaataca | arttcaatct | 720 |
| gtgttttgaa | aacwcdcaag | gctatggcta | tgtaactgaa | aaaatcattg | acgcttaytt | 780 |
| yagccatacc | attcctattt | attgggggnn | agtccnyagc | gtggcrmaag | attttaaccc | 840 |
| taaragtttt | gtgaatgtby | rtgatttyaa | mrayttgat | gaagcgattg | ayyatrtsmr | 900 |
| atacytgcac | acgcacccaa | acgcttattt | agacatgcwy | tatgaaaacc | ctttaaacac | 960 |
| ymttgatggg | aaagcttact | tttaccaara | tttgagtttt | aaaaaaatcc | tagatttttt | 1020 |
| taaaacgaty | ttagaaaacg | ayacgatyta | tcacrawwwc | ycnnnnnntt | tyatktkbka | 1080 |
| kyrygatytg | matragcckt | yartatcyat | tgatgrtnnn | ttgagggtta | attatgatga | 1140 |
| tttgagggtt | aattatgays | rkytkwkrsw | waaykmtkmk | smtttrwkrg | wwmwytmtsa | 1200 |
| dvryhybwbd | bwwaahdhyk | mksvywwrdb | dkwwywhwmw | bmhdwbhybw | bkktkmrhdh | 1260 |
| bkwkvrhwwr | dbkkwtmaww | awkhbkdkyy | kwdrktkmrt | kvyrwwrrkw | krwgggttaa | 1320 |
| wwakkawgat | ttgagggtta | attatgagcg | gctcttacaa | aacgcctcgc | ctttattaga | 1380 |
| actctctcaa | aacaccactt | ttaaaatcta | tcgcaaagct | tatcaaaaat | ccttacctt | 1440 |
| gttgcgtgcg | gcgagaaagt | tgattaaaaa | attgggtttg | taa | | 1483 |

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence:"FLAG tag" epitope tag recognized by anti-LAG antibody

<400> SEQUENCE: 80

-continued

```
Asp Tyr Lys Asp Asp Asp Asp Lys
 1               5

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence:
      polyhistidine metal chelate affinity purification tag,
      hexahistidine affinity tag

<400> SEQUENCE: 81

His His His His His His
 1               5
```